United States Patent
Betzold

(10) Patent No.: US 6,594,526 B2
(45) Date of Patent: Jul. 15, 2003

(54) PACING THERAPY ARCHITECTURE FLOW

(75) Inventor: Robert A. Betzold, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/750,632

(22) Filed: Dec. 28, 2000

(65) Prior Publication Data

US 2002/0193841 A1 Dec. 19, 2002

(51) Int. Cl.$^7$ ................................................ A61N 1/08
(52) U.S. Cl. ......................................................... 607/59
(58) Field of Search .................. 607/1–114; 604/890.1, 604/891.1, 892.1

(56) References Cited

U.S. PATENT DOCUMENTS

| | | | |
|---|---|---|---|
| 4,211,235 A | 7/1980 | Keller, Jr. et al. | 128/419 PG |
| 4,357,943 A | 11/1982 | Thompson et al. | 128/419 PG |
| 4,476,868 A | 10/1984 | Thompson | 128/419 PG |
| 4,539,992 A | 9/1985 | Calfee et al. | 128/419 PG |
| 4,550,732 A | 11/1985 | Batty, Jr. et al. | 128/419 PG |
| 4,556,063 A | 12/1985 | Thompson et al. | 128/419 PT |
| 4,571,589 A | 2/1986 | Slocum et al. | 340/870.32 |
| 4,676,248 A | 6/1987 | Berntson | 128/419 PG |
| 5,052,388 A | 10/1991 | Sivula et al. | 128/419 PG |
| 5,127,404 A | 7/1992 | Wyborny et al. | 128/419 P |
| 5,345,362 A | 9/1994 | Winkler | 361/681 |

*Primary Examiner*—Scott M. Getzow
(74) *Attorney, Agent, or Firm*—Girma Wolde-Michael

(57) ABSTRACT

A device is provided, the device comprising an implantable medical device and a controller controlling the implantable medical device, the controller having a plurality of modular features and having a firmware architecture allowing modular feature design and implementation, the firmware architecture coordinating between and among the plurality of modular features to reduce feature-to-feature interactions. The device also comprises the controller having a converter enabling efficient conversion between at least one identifiable first modular feature working in a rate domain and at least one identifiable second modular feature working in an interval domain.

30 Claims, 52 Drawing Sheets

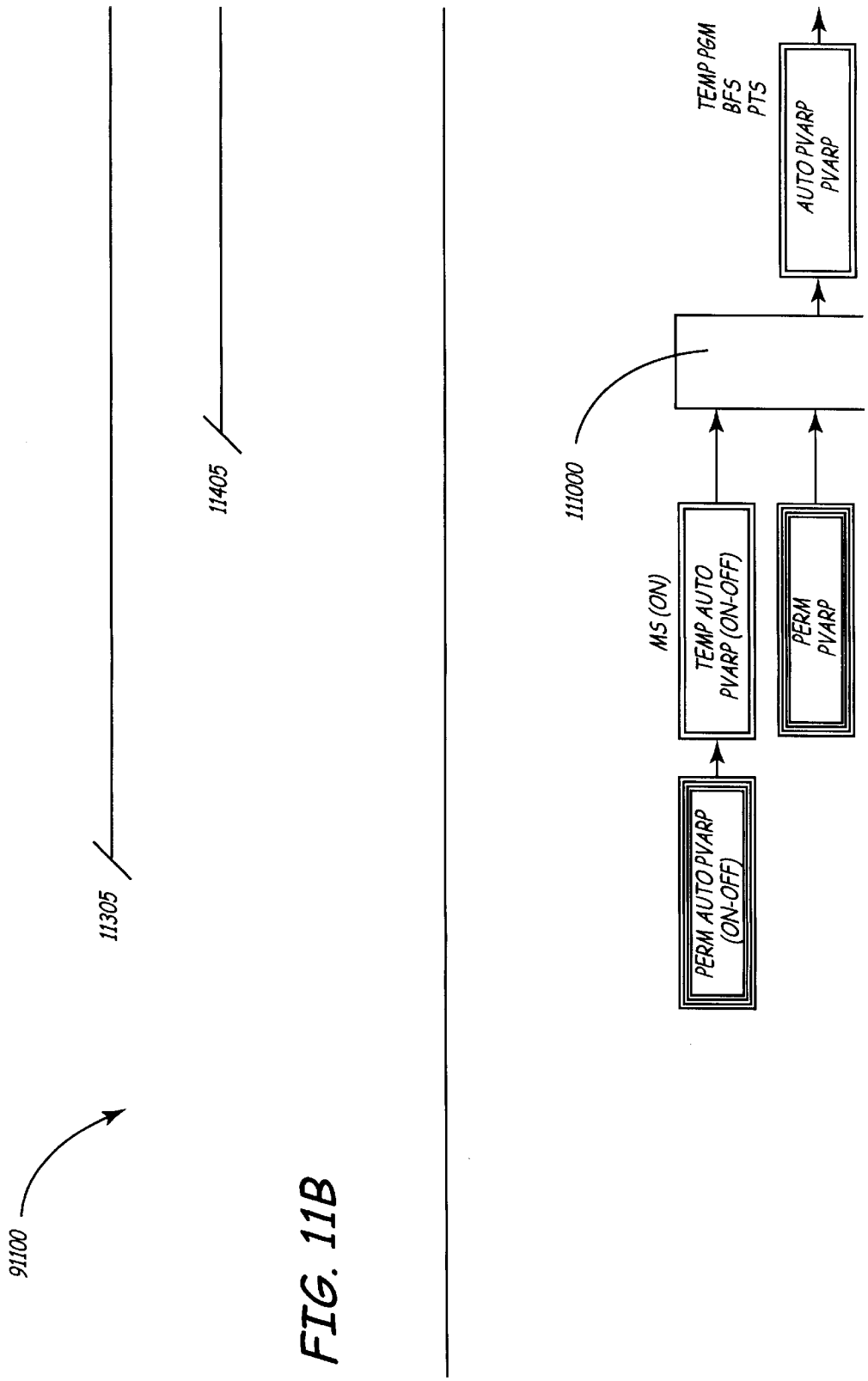

FIG. 12D
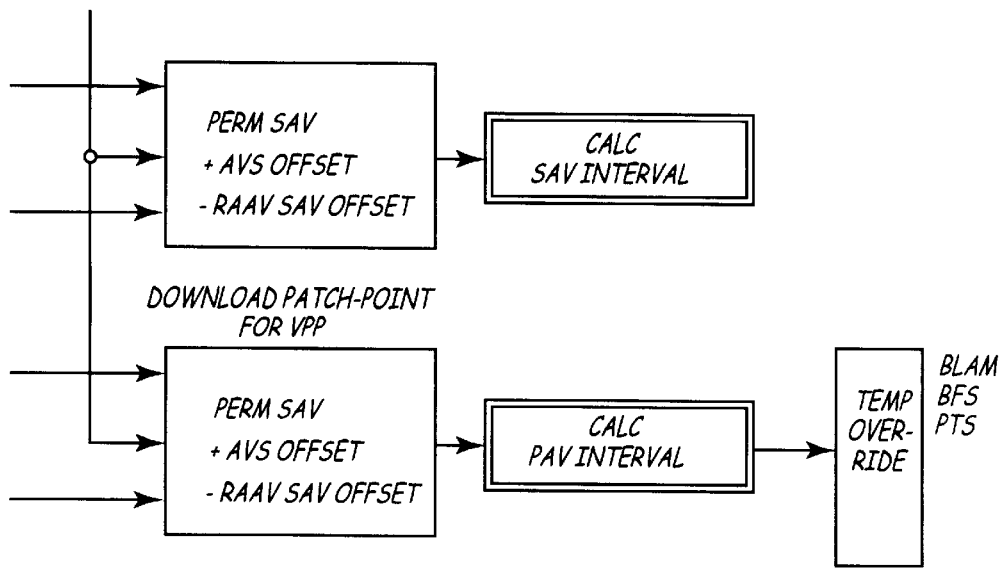
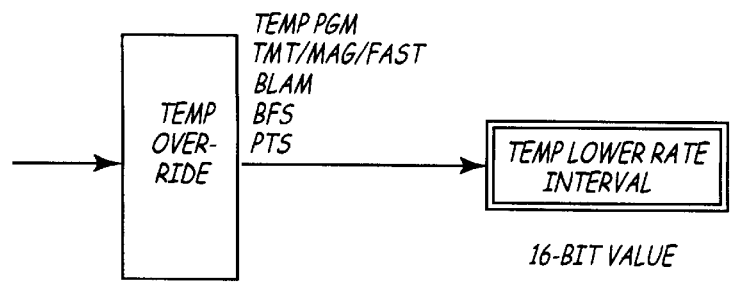

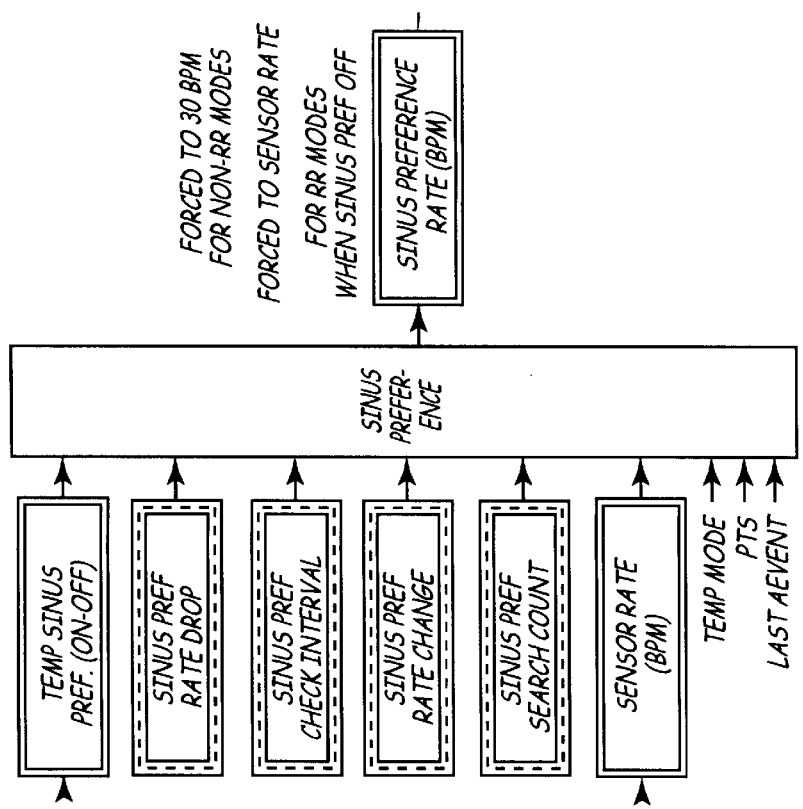
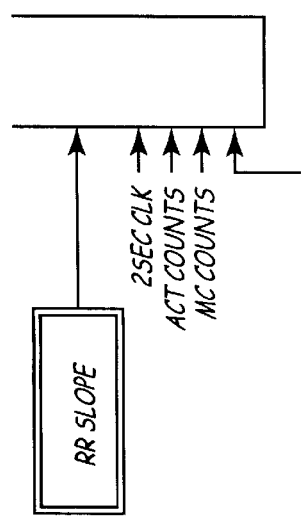
FIG. 14C

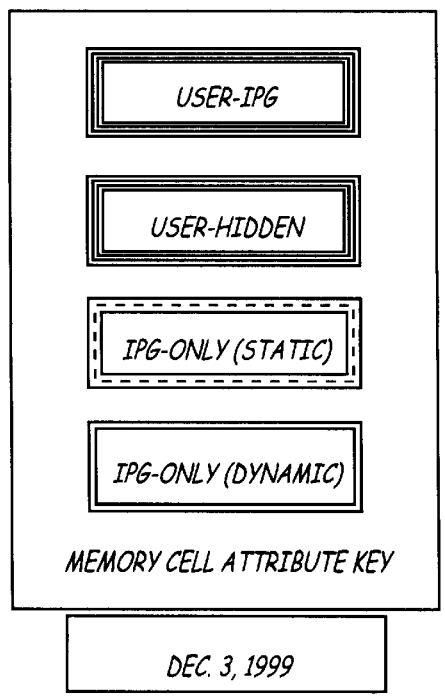
FIG. 14D
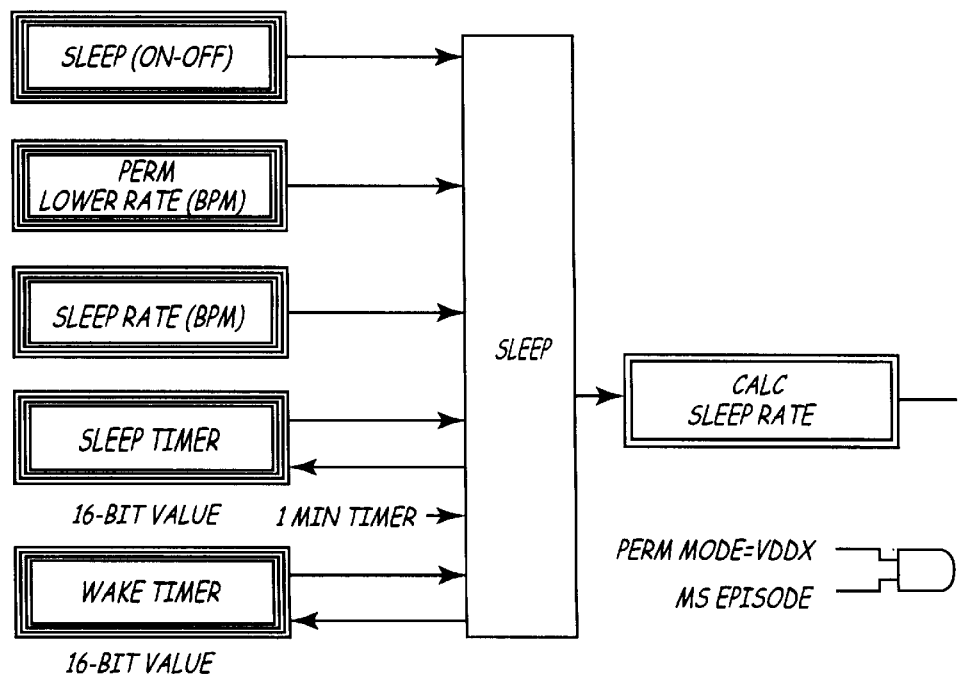

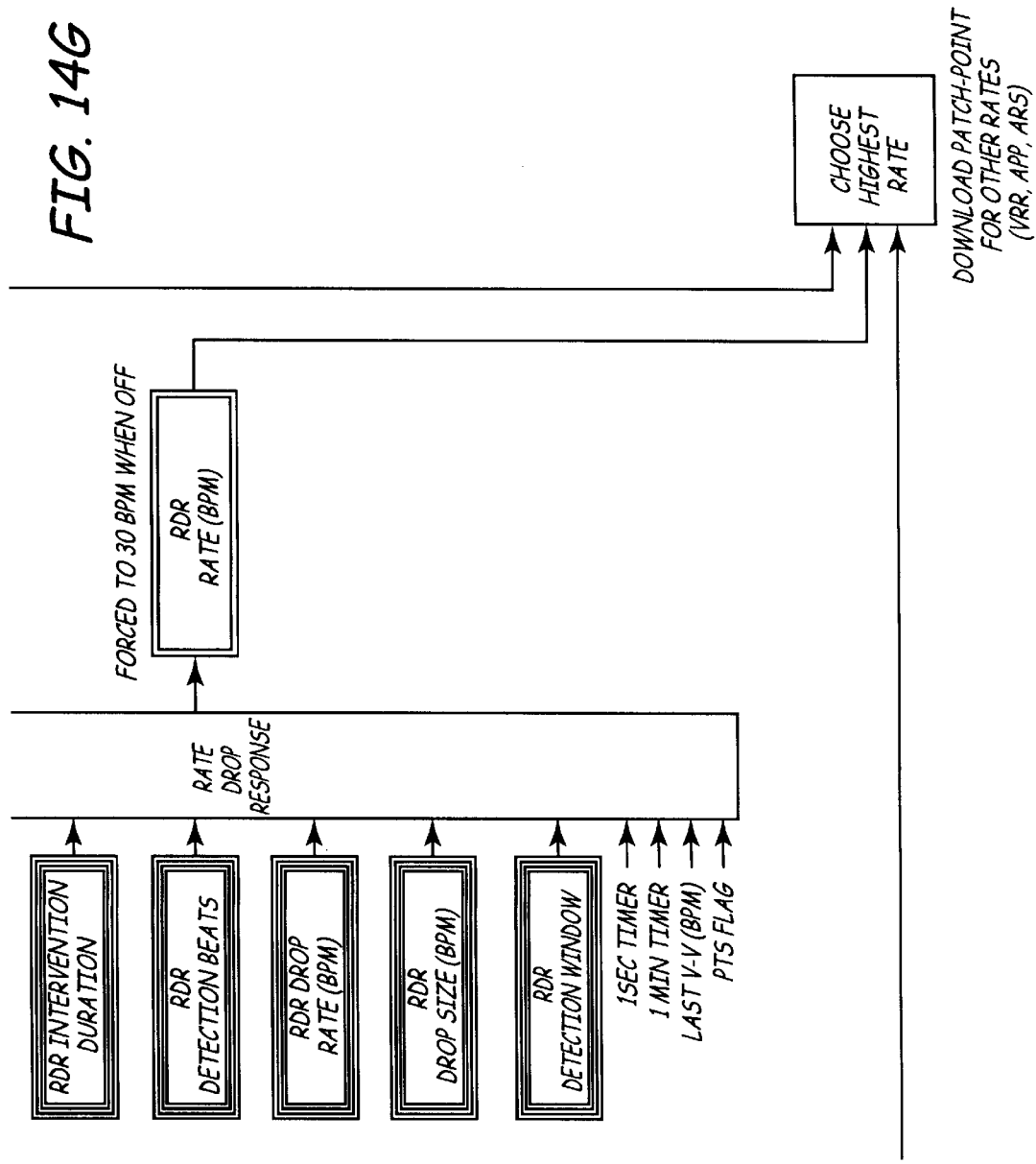

PACING THERAPY ARCHITECTURE FLOW

BACKGROUND OF THE INVENTION

1. Field of the Invention

This invention relates generally to implantable medical devices and, more particularly, to a firmware architecture permitting modular feature design for implantable medical devices.

2. Description of the Related Art

Since the introduction of the first implantable pacemakers in the 1960s, there have been considerable advances in both the fields of electronics and medicine, such that there is presently a wide assortment of commercially available body-implantable electronic medical devices. The class of implantable medical devices now includes pacemakers, implantable cardioverters, defibrillators, neural stimulators, and drug administering devices, among others. Today's state-of-the-art implantable medical devices are vastly more sophisticated and complex than earlier ones. Today's state-of-the-art implantable medical devices are capable of performing significantly more complex tasks. The therapeutic benefits of such devices have been well proven.

As the functional sophistication and complexity of implantable medical device systems have increased over the years, it has become increasingly useful to include a system for facilitating communication between one implanted device and another implanted or external device, for example, a programming console, monitoring system, or the like. Shortly after the introduction of the earliest pacemakers, it became apparent that it would be desirable for physicians to non-invasively obtain information regarding the operational status of the implanted device, and/or to exercise at least some control over the device, e.g., to turn the device on or off or adjust the pacing rate, after implant. As new, more advanced features have been incorporated into implantable devices, it has been increasingly useful to convey correspondingly more information to/from the device relating to the selection and control of those features.

In particular, implantable pacemaker therapies have grown in number and complexity. In conventional devices this growth in the number and complexity of the various implantable pacemaker therapies has led to numerous feature interactions. These feature-to-feature interactions may adversely affect the efficacy of various of the implantable pacemaker therapies.

For example, in conventional implantable pacemakers, various therapy algorithms write to the same memory location associated with a temporary parameter related to the beat-to-beat control of the implantable pacemaker. These temporary parameters may include Temporary Lower Rate Interval (TEMP LR INT), Temporary Pacing Atrial Ventricle Interval (TEMP PAV INT), Temporary Sensing Atrial Ventricle Interval (TEMP SAV INT), Temporary Post-Ventricular Atrial Refractory Period (TEMP PVARP), and the like. In conventional implantable pacemakers, the last algorithm to write to the memory location "won" (controlled the setting of the parameter value). Because of this, feature interactions are difficult to manage in conventional implantable pacemakers. Typically, multiple therapy features, such as Mode Switch (MS) and Rate Drop Response (RDR), are not able to operate at the same time. To resolve adverse feature-to-feature interactions, specific features are typically forced "off" (either by the programmer or within the conventional implantable pacemaker) when another feature is turned "on." Additionally, these complex feature interactions, particularly in brady and tachy devices, lead to slow and difficult development of feature addition, modification and/or removal, because the features are not modular and cannot easily be added, modified and/or removed from a conventional implantable pacemakers during development.

The present invention is directed to overcoming, or at least reducing the effects of, one or more of the problems set forth above.

SUMMARY OF THE INVENTION

In one aspect of the present invention, a device is provided, the device comprising an implantable medical device and a controller controlling the implantable medical device, the controller having a plurality of modular features and having a firmware architecture allowing modular feature design and implementation, the firmware architecture coordinating between and among the plurality of modular features to reduce feature-to-feature interactions. The device also comprises the controller having a converter enabling efficient conversion between at least one identifiable first modular feature working in a rate domain and at least one identifiable second modular feature working in an interval domain.

In another aspect of the present invention, a method is provided, the method comprising controlling an implantable medical device using a controller having a plurality of modular features, the controller having a firmware architecture allowing modular feature design and implementation, and coordinating between and among the plurality of modular features to reduce feature-to-feature interactions. The method also comprises identifying at least one first modular feature working in a rate domain and at least one second modular feature working in an interval domain, enabling efficient conversion between the rate domain and the interval domain.

In yet another aspect of the present invention, a device is provided, the device comprising means for controlling an implantable medical device using a controller having a plurality of modular features, the controller having a firmware architecture allowing modular feature design and implementation, and means for coordinating between and among the plurality of modular features to reduce feature-to-feature interactions. The device also comprises means for identifying at least one first modular feature working in a rate domain and at least one second modular feature working in an interval domain, enabling efficient conversion between the rate domain and the interval domain.

BRIEF DESCRIPTION OF THE DRAWINGS

The invention may be understood by reference to the following description taken in conjunction with the accompanying drawings, in which the leftmost significant digit(s) in the reference numerals denote(s) the first figure in which the respective reference numerals appear, and in which:

FIG. 1 schematically illustrates an implantable medical device (IMD) system according to the present invention;

FIG. 2 schematically illustrates a general block diagram of electronic circuitry for the implantable medical device (IMD) system of FIG. 1;

FIG. 3 schematically illustrates a perspective view of one embodiment of the programming unit for the implantable medical device (IMD) system of FIG. 1;

FIG. 4 schematically illustrates a general block diagram of various illustrative embodiments of a device comprising an implantable medical device (IMD) and an implantable medical device (IMD) controller controlling the implantable medical device according the present invention;

FIG. 5 schematically illustrates an implantable medical device (IMD) controller having a plurality of modular features;

FIG. 6 schematically illustrates controlling an implantable medical device (IMD) using an implantable medical device (IMD) controller by adding a modular feature to lower level firmware;

FIG. 7 schematically illustrates controlling an implantable medical device (IMD) using an implantable medical device (IMD) controller by modifying a modular feature in lower level firmware;

FIG. 8 schematically illustrates controlling an implantable medical device (IMD) using an implantable medical device (IMD) controller by deleting a modular feature from lower level firmware;

FIG. 9 schematically illustrates an embodiment of a pacing therapy architecture flow according the present invention;

FIG. 10 schematically illustrates a key to attributes of memory cells comprising the embodiment of lower level firmware shown in FIGS. 9 and 11–25;

FIG. 11 schematically illustrates the rightmost portion of the embodiment of lower level firmware for the pacing therapy architecture flow shown in FIG. 9;

FIG. 12 schematically illustrates the next-to-rightmost portion of the embodiment of lower level firmware for the pacing therapy architecture flow shown in FIG. 9;

FIG. 13 schematically illustrates the next-to-leftmost portion of the embodiment of lower level firmware for the pacing therapy architecture flow shown in FIG. 9;

FIG. 14 schematically illustrates the leftmost portion of the embodiment of lower level firmware for the pacing therapy architecture flow shown in FIG. 9;

FIG. 15 schematically illustrates a sleep modular feature in the leftmost portion of the embodiment of lower level firmware shown in FIG. 14;

FIG. 16 schematically illustrates a rate drop response modular feature in the leftmost portion of the embodiment of lower level firmware shown in FIG. 14;

FIG. 17 schematically illustrates a physiological rate modular feature in the next-to-leftmost portion of the embodiment of lower level firmware shown in FIG. 13;

FIG. 18 schematically illustrates a rate response modular feature and a sinus preference modular feature in the leftmost portion of the embodiment of lower level firmware shown in FIG. 14;

FIG. 19 schematically illustrates a mode switch modular feature in the next-to-leftmost portion of the embodiment of lower level firmware shown in FIG. 13;

FIG. 20 schematically illustrates an atrial ventricular interval search modular feature in the next-to-rightmost portion of the embodiment of lower level firmware shown in FIG. 12;

FIG. 21 schematically illustrates a rate adaptive atrial ventricular modular feature in the next-to-rightmost portion of the embodiment of lower level firmware shown in FIG. 12;

FIG. 22 schematically illustrates a memory cell from the upper portion of the embodiment of lower level firmware shown in FIG. 12;

FIG. 23 schematically illustrates an adaptive (or automatic) post-ventricular atrial refractory period modular feature in the rightmost portion of the embodiment of lower level firmware shown in FIG. 11.

FIG. 24 schematically illustrates the embodiment of the pacing therapy architecture flow according the present invention shown in FIG. 9; and FIG. 25 schematically illustrates an embodiment of the pulse generator input registers (PGIRs) shown in FIG. 24.

Figure 1:
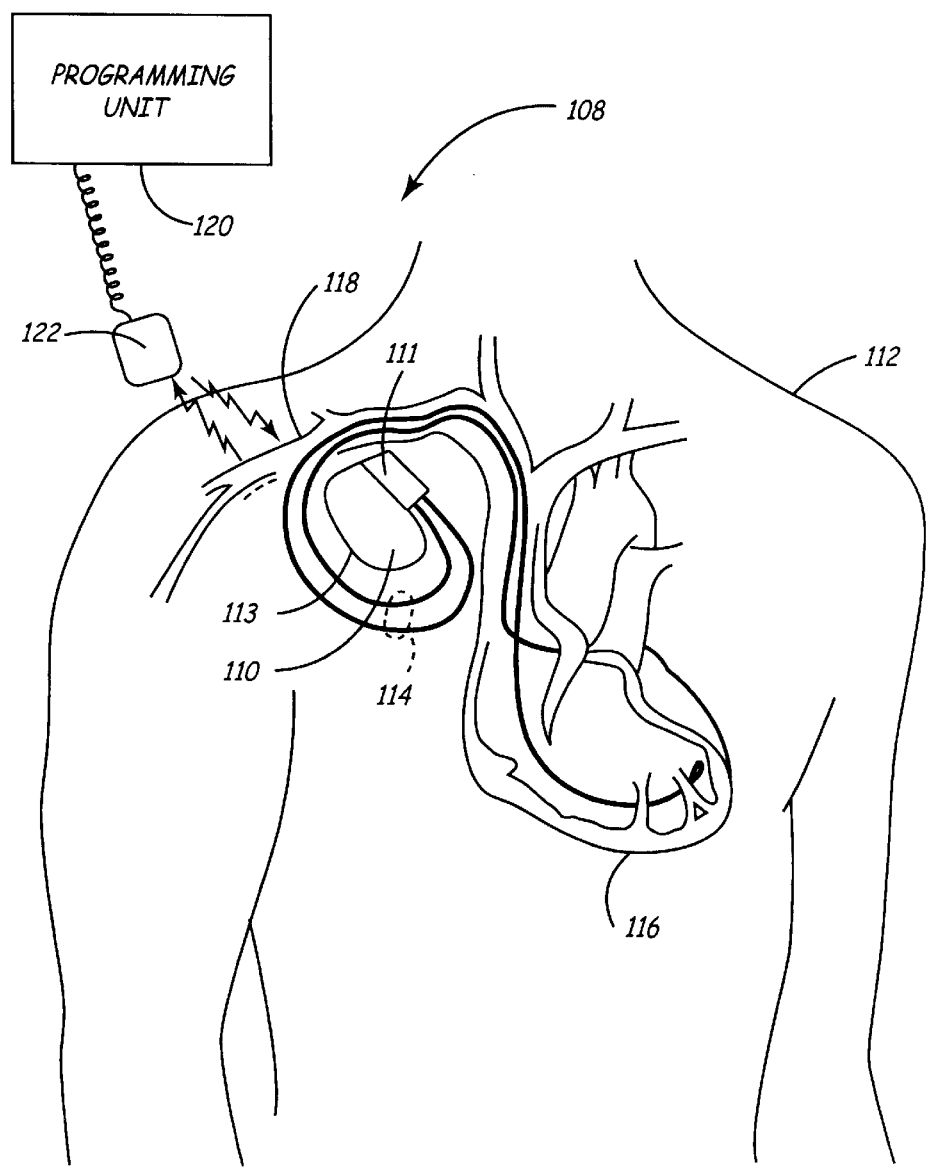
FIGS. 1–25 schematically illustrate various embodiments of a method and a device according to the present invention; and, more particularly.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Illustrative embodiments of an apparatus and a method for operation of the apparatus according to the present invention are shown in FIGS. 1–25. FIG. 1 illustrates an implantable medical device (IMD) system 108, which includes, for example, an implantable pacemaker 110 that has been implanted in a patient 112. The pacemaker 110 is housed within a hermetically sealed, biologically inert outer canister or housing 113, which may itself be conductive so as to serve as an electrode in the pacemaker's pacing/sensing circuit. One or more pacemaker leads, collectively identified with reference numeral 114 in FIG. 1 are electrically coupled to the pacemaker 110 in a conventional manner and extend into the patient's heart 116 via a vein 118. Disposed generally near a distal end of the leads 114 are one or more exposed conductive electrodes for receiving electrical cardiac signals or delivering electrical pacing stimuli to the heart 116. The leads 114 may be implanted with their distal end situated in either the atrium or ventricle of the heart 116.

Although the present invention is described herein in an embodiment that includes a pacemaker, it may be advantageously embodied in numerous other types of implantable medical device systems in which it is desirable to provide a communication link between two physically separated components and retrieve data stored therein.

FIG. 1 also depicts an external programming unit 120 for non-invasive communication with the implanted device 110 via conventional uplink and downlink communication channels, which are not described in greater detail herein so as to avoid unnecessarily obscuring the instant invention. Associated with the programming unit 120 is a programming head 122, in accordance with conventional medical device programming systems, for facilitating two-way communication between the pacemaker 110 and the programmer 120. In many known implantable device systems, the programming head 122, such as that depicted in FIG. 1, is positioned on the patient's body over the implant site of the device 110 (usually within about 2 to about 3 inches, or equivalently, about 5 to about 8 cm, of skin contact), such that one or more antennas within the head 122 can send radio frequency (RF) signals to, and receive radio frequency (RF) signals from, an antenna (not shown) disposed within the hermetic enclosure of the implanted device 110 or disposed within a connector block 111 of the device 110, in accordance with common practice in the art.

Figure 2:
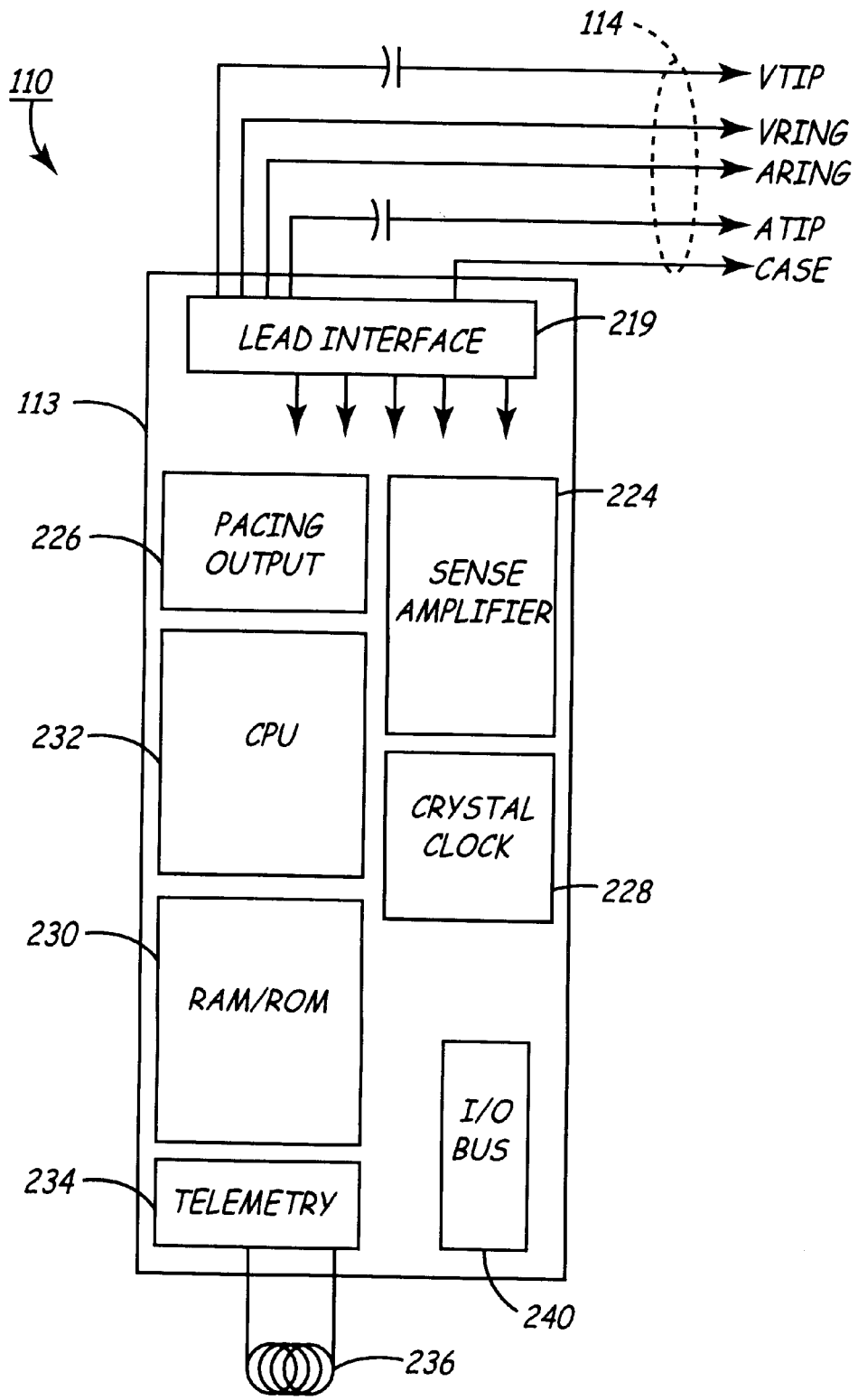

FIG. 2 provides a general block diagram of electronic circuitry that makes up the pacemaker 110. The pacemaker 110 is a device capable of performing a variety of functions, such as delivering electrical stimulation therapy to the patient 112 in accordance with the presently disclosed embodiment of the invention. FIG. 2 shows that pacemaker 110 comprises circuitry for controlling the device's pacing and sensing functions. Aspects of the pacemaker circuitry may be of conventional design, in accordance; for example, with what is disclosed in U.S. Pat. No. 5,052,388 issued to Sivula et al. and entitled "Method and Apparatus for Implementing Activity Sensing in a Pulse Generator." The '388 patent is hereby incorporated by reference herein in its entirety.

To the extent that certain components of the circuitry of the pacemaker 110 are conventional in their design and operation, such components will not be described herein in detail, as it is believed that design and implementation of such components would be a matter of routine practice to those of ordinary skill in the art. For example, the circuitry of the pacemaker 110 shown in FIG. 2 includes sense amplifier circuitry 224, stimulating pulse output circuitry 226, a crystal clock 228, a random-access memory and read-only memory (RAM/ROM) unit 230, and a pacing timing and control circuit in the form of a programmed central processing unit (CPU) 232, all of which are well-known in the art.

The pacemaker 110 also includes an internal telemetry communications circuit 234 coupled to an antenna 236 so that it is capable of communicating with the external programmer/control unit 120. Various telemetry systems for providing the uplink and downlink communication channels between the external programming unit 120 and the implanted pacemaker 110 have been shown in the art and may be employed herein without departing from the spirit and scope of the instant invention. Exemplary communication telemetry systems that may be utilized herein are disclosed, for example, in the following U.S. patents: U.S. Pat. No. 4,539,992 to Calfee et al. entitled "Method and Apparatus for Communicating With Implanted Body Function Stimulator," U.S. Pat. No. 4,550,732 to Batty Jr. et al. entitled "System and Process for Enabling a Predefined Function Within An Implanted Device," U.S. Pat. No. 4,751, 589 to Slocum et al. entitled "Biomedical Implant With High Speed, Low Power Two-Way Telemetry," U.S. Pat. No. 4,676,248 to Berntson entitled "Circuit for Controlling a Receiver in an Implanted Device," U.S. Pat. No. 5,127,404 to Wyborny et al. entitled "Telemetry Format for Implanted Medical Device," U.S. Pat. No. 4,211, 235 to Keller, Jr. et al. entitled "Programmer for Implanted Device," the above-referenced Markowitz '382 patent and U.S. Pat. No. 4,556, 063 to Thompson et al. entitled "Telemetry System for a Medical Device." The Wyborny et al. '404 patent and the Thompson et al. '063 patent are hereby incorporated by reference herein in their respective entireties.

With continued reference to FIG. 2, the pacemaker 110 is coupled to one or more leads 114 which, when implanted, extend transvenously between the implant site of the pacemaker 110 and the patient's heart 116, as previously noted with reference to FIG. 1. Physically, the connections between the leads 114 and the various internal components of the pacemaker 110 are facilitated by a conventional connector block assembly 111, shown in FIG. 1 but not shown in FIG. 2. Electrically, the coupling of the leads 114 and the internal electrical components of the pacemaker 110 may be facilitated by a lead interface circuit 219, which functions, in a multiplexer-like manner, to selectively and dynamically establish necessary connections between various conductors in the leads 114, including, for example, atrial tip and ring electrode conductors ATIP and ARING and ventricular tip and ring electrode conductors VTIP and VRING, and individual electrical components of the pacemaker 110, as would be familiar to those of ordinary skill in the art. For the sake of clarity, the specific connections between the leads 114 and the various components of the pacemaker 110 are not shown in FIG. 2, although it will be clear to those of ordinary skill in the art that, for example, the leads 114 will necessarily be coupled, either directly or indirectly, to sense amplifier circuitry 224 and stimulating pulse output circuitry 226, in accordance with common practice, such that cardiac electrical signals may be conveyed to the sense amplifier circuitry 224, and such that stimulating pulses may be delivered to cardiac tissue, via the leads 114.

It will be appreciated that the signals received over the leads 114 by the sense amplifier circuitry 224 may be collected and stored in the RAM/ROM unit 230 by the CPU 232 acting under control of software also stored in the RAM/ROM unit 230. Additional data, such as the timing of signals delivered by the stimulating pulse output circuitry 226 may also be stored in the RAM/ROM unit 230. This stored data may be later retrieved and delivered to the programming unit 120 via the telemetry communications circuit 234.

As previously noted, the circuitry of the pacemaker 110 includes the central processing unit (CPU) 232 which may be an off-the-shelf programmable microprocessor or microcontroller, but in the presently illustrated embodiment of the invention is a custom integrated circuit. Although specific connections between the CPU 232 and other components of the pacemaker circuitry are not shown in FIG. 2, it will be apparent to those of ordinary skill in the art that the CPU 232 functions to control the timed operation of the stimulating pulse output circuit 226 and the sense amplifier circuit 224 under control of a program of instructions stored in the RAM/ROM unit 230. The crystal clock 228 in the presently illustrated embodiment is a crystal controlled oscillator that provides a main timing clock signal. Again, the lines over which such clock signals are provided to the various components of the pacemaker 110 (e.g., the CPU 232) are omitted from FIG. 2 for the sake of clarity. It is believed that those of ordinary skill in the art will be familiar with such an operative arrangement.

It is to be understood that the various components of the pacemaker 110 depicted in FIG. 2 are powered by means of a battery (not shown), which is contained within the hermetic enclosure of the pacemaker 110, in accordance with common practice in the art. For the sake of clarity in the drawings, the battery and the connections between it and the other components of the pacemaker 110 are not shown.

Stimulating pulse output circuitry 226, which functions to generate cardiac stimuli under control of signals issued by the CPU 232, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits, which would be suitable for the purposes of practicing the present invention.

The sense amplifier circuitry 224, may be, for example, of the type disclosed in U.S. Pat. No. 4,357,943 to Thompson, entitled "Demand Cardiac Pacemaker Having Reduced Polarity Disparity," which patent is hereby incorporated by reference herein in its entirety. Generally, the sense amplifier circuitry 224 functions to receive electrical cardiac signals from the leads 114 and to process such signals to derive event signals reflecting the occurrence of specific cardiac electrical events, including atrial contractions (P-waves) and ventricular contractions (R-waves). These event-indicating signals are provided to the CPU 232 for use by the CPU 232 in controlling the synchronous stimulating operations of the pacemaker 110 in accordance with common practice in the art. In addition, these event-indicating signals, as discussed above, may be communicated, via the uplink communication channel, to the external programming unit 120 for storage and visual display to a physician or clinician.

Those of ordinary skill in the art will appreciate that the pacemaker 110 may include numerous other components and subsystems, for example, activity sensors and associated circuitry. The presence or absence of such additional components in the pacemaker 110, however, is not believed to be directly pertinent to the present invention, which relates generally to the firmware architecture of a portion of the RAM/ROM unit 230, permitting modular feature design for the pacemaker 110, and to the method of operation of this firmware architecture.

Figure 3:
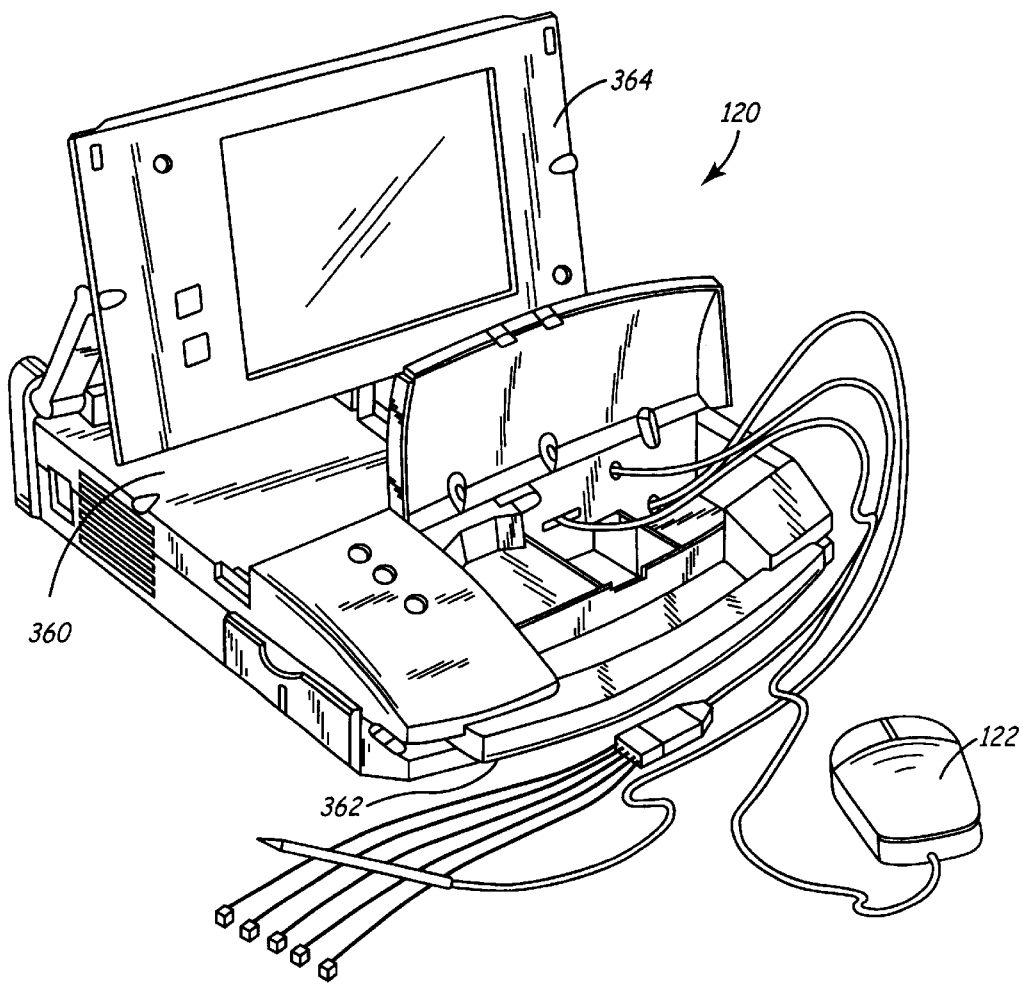

FIG. 3 shows a perspective view of one embodiment of the programming unit 120 in accordance with the presently disclosed embodiment of the invention. Internally, the programmer 120 includes a processing unit (not shown), which in accordance with the presently disclosed embodiment of the invention is a personal computer-type motherboard, for example, a computer motherboard including an Intel 80×86 microprocessor or the like and related circuitry such as digital memory.

Referring to FIG. 3, the programming unit 120 comprises an outer housing 360, which is preferably made of thermal plastic or another suitably rugged yet relatively lightweight material. A carrying handle, designated generally as 362 in FIG. 3, is integrally formed into the front of the housing 360. With the handle 362, the programming unit 120 can be carried like a briefcase.

An articulating display screen 364 is disposed on an upper surface of the housing 60. The display screen 364 folds down into a closed position (not shown) when the programming unit 120 is not in use, thereby reducing the size of the programming unit 120 and protecting the display surface of the display 364 during transportation and storage thereof.

A floppy disk drive is disposed within the housing 360 and is accessible via a disk insertion slot (not shown). A hard disk drive is also disposed within the housing 360, and it is contemplated that a hard disk drive activity indicator (e.g., an LED, not shown) could be provided to give a visible indication of hard disk activation.

As would be appreciated by those of ordinary skill in the art, it is often desirable to provide a means for the programming unit 120 to adapt its mode of operation depending upon the type of implanted device to be programmed. Accordingly, it may be desirable to have an expansion cartridge containing EPROMS or the like for storing program information to control the programming unit 120 to operate in a particular manner corresponding to a given type of implantable device.

In accordance with the presently illustrated embodiment of the invention, the programming unit 120 is equipped with an internal printer (not shown) so that a hard copy of a patient's electrocardiogram (ECG) or of graphics displayed on the programmer's display screen 364 can be generated. Several types of printers, such as the AR-100 printer available from General Scanning Co., are known and commercially available.

In the perspective view of FIG. 3, the programming unit 120 is shown with the articulating display screen 364 having been lifted up into one of a plurality of possible open positions such that the display area thereof is visible to a user situated in front of the programming unit 120. The articulating display screen 364 is preferably of the LCD or electro-luminescent type, characterized by being relatively thin as compared, for example, a cathode ray tube (CRT) or the like.

The display screen 364 is operatively coupled to computer circuitry disposed within the housing 360, and is adapted to provide a visual display of graphics and/or data under control of the internal computer.

One embodiment of the programming unit 120 described herein with reference to FIG. 3 is described in more detail in U.S. Pat. No. 5,345,362 issued to Thomas J. Winkler, entitled "Portable Computer Apparatus With Articulating Display Panel," which patent is hereby incorporated herein by reference in its entirety. Also, the Medtronic Model 9760 or 9790 programmers are other implantable device programming units with which the present invention may be advantageously practiced.

Figure 4:
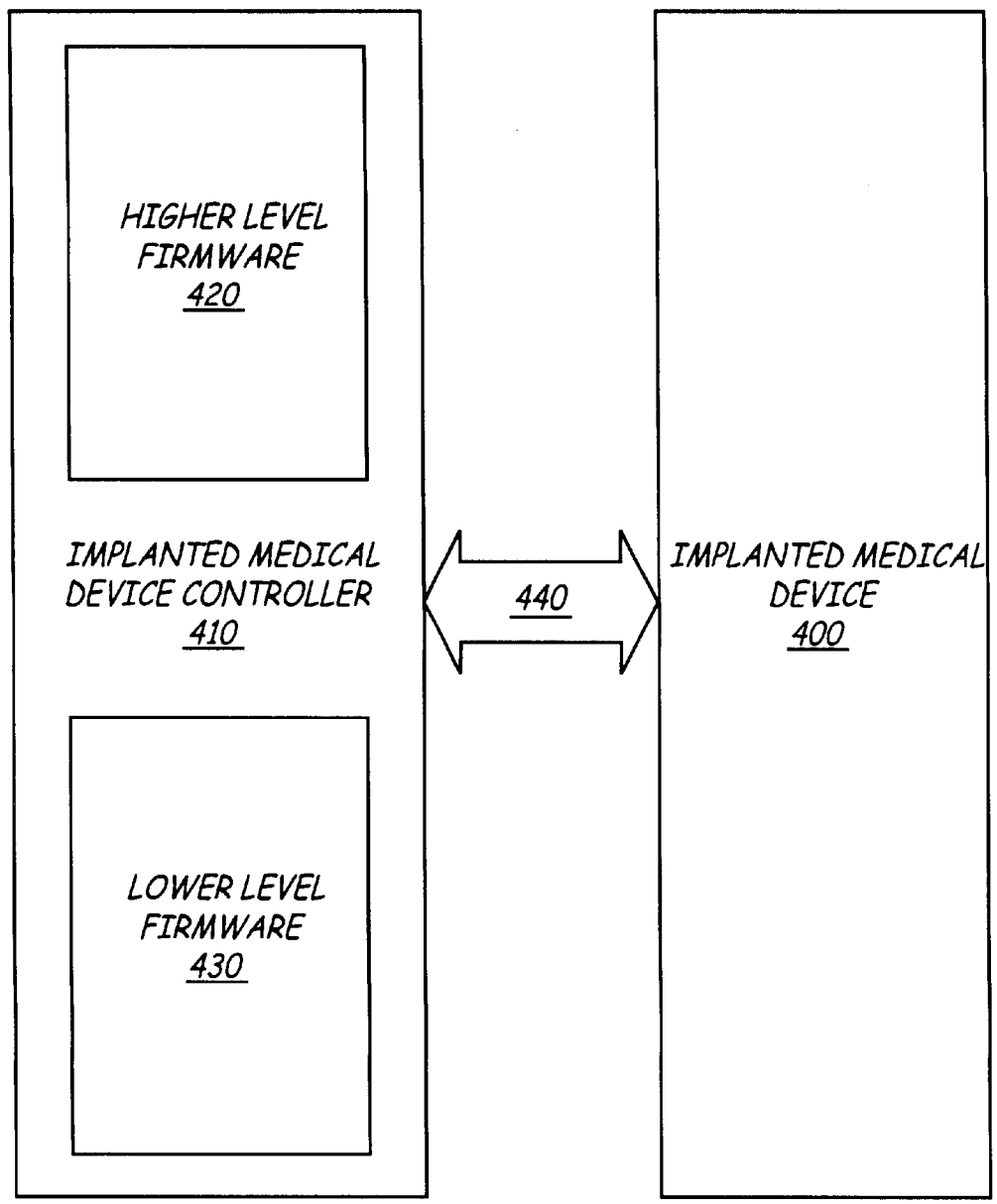

Turning to FIG. 4, a general block diagram of various illustrative embodiments of a device according the present invention is shown, comprising an implantable medical device (IMD) 400 and an implantable medical device (IMD) controller 410 controlling the implantable medical device 400. The implantable medical device (IMD) 400 may comprise an implantable pulse generator (IPG) for an implantable pacemaker, such as an implantable anti-brady pacemaker and/or an implantable anti-tachy pacemaker. The implantable medical device (IMD) controller 410 may have higher level firmware 420 and lower level firmware 430. The implantable medical device (IMD) 400 and the implantable medical device (IMD) controller 410 may communicate via coupler 440.

Figure 5:
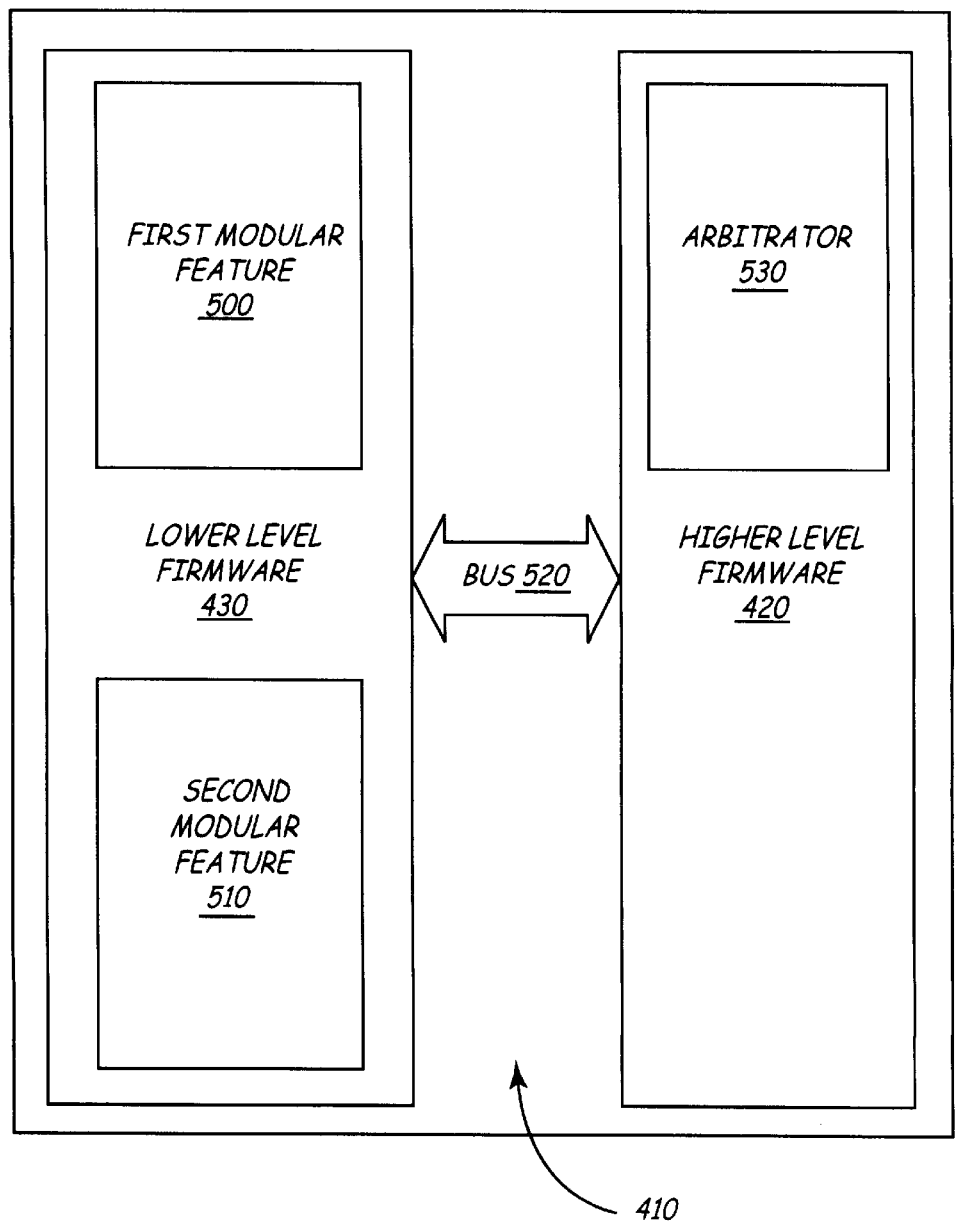

As shown in FIG. 5, the implantable medical device (IMD) controller 410 may have a plurality of modular features, such as first modular feature 500 and second modular feature 510. The implantable medical device (IMD) controller 410 may have a firmware architecture, described in more detail below, allowing modular feature design and implementation. The firmware architecture of the implantable medical device (IMD) controller 410 may coordinate between and among the plurality of modular features, such as the first modular feature 500 and the second modular feature 510, to reduce feature-to-feature interactions. The implantable medical device (IMD) controller 410 may also have a converter (not shown) enabling efficient conversion between at least one identifiable first modular feature, for example, the first modular feature 500, working in a rate domain (beats per minute or BPM), and at least one identifiable second modular feature, for example, the second modular feature 510, working in an interval domain (usually in milliseconds or msec). The converter may be included in the higher level firmware 420 and/or the lower level firmware 430. Alternatively, and/or additionally, the converter may be included elsewhere in the implantable medical device (IMD) controller 410.

Figure 6:
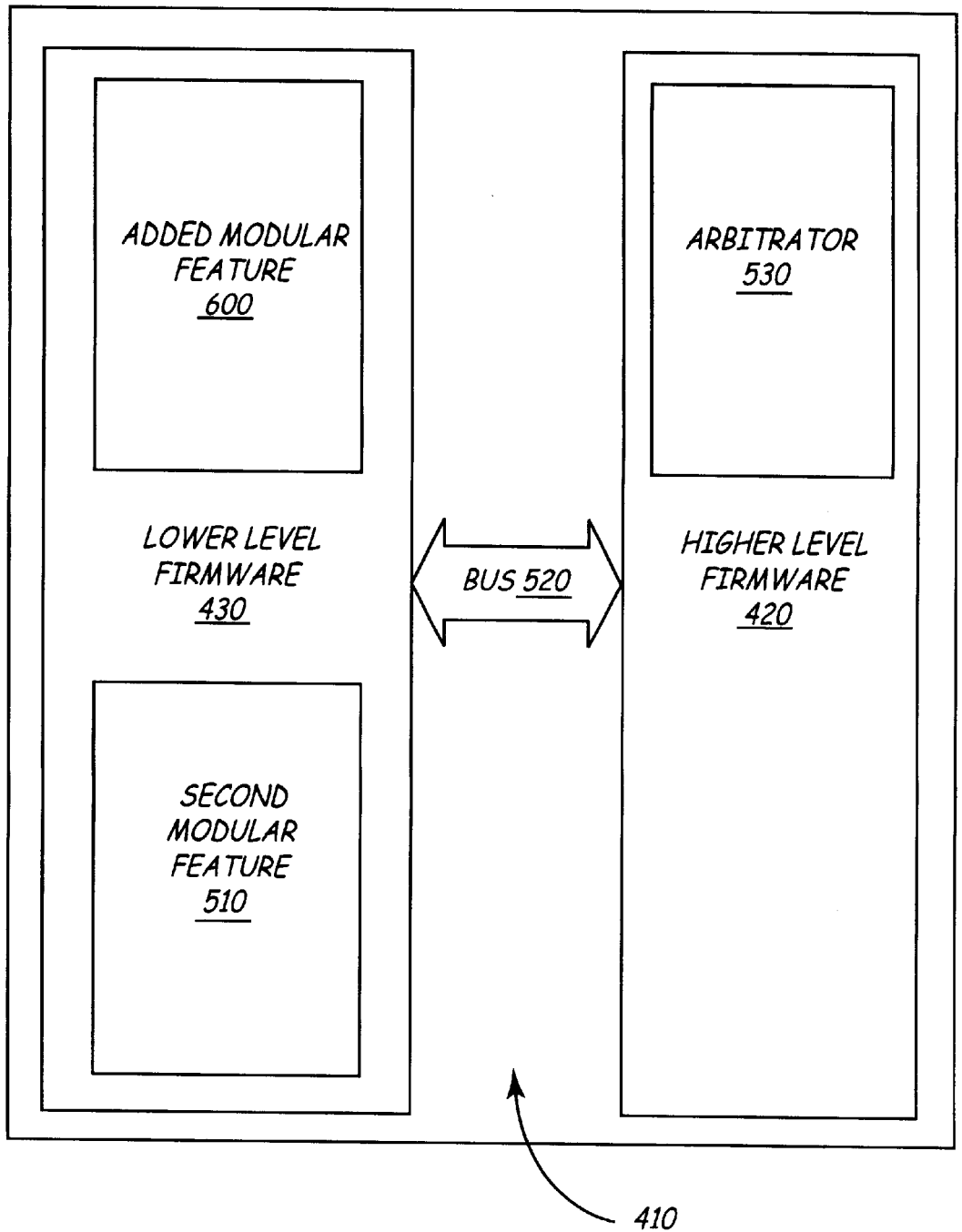
Figure 7:
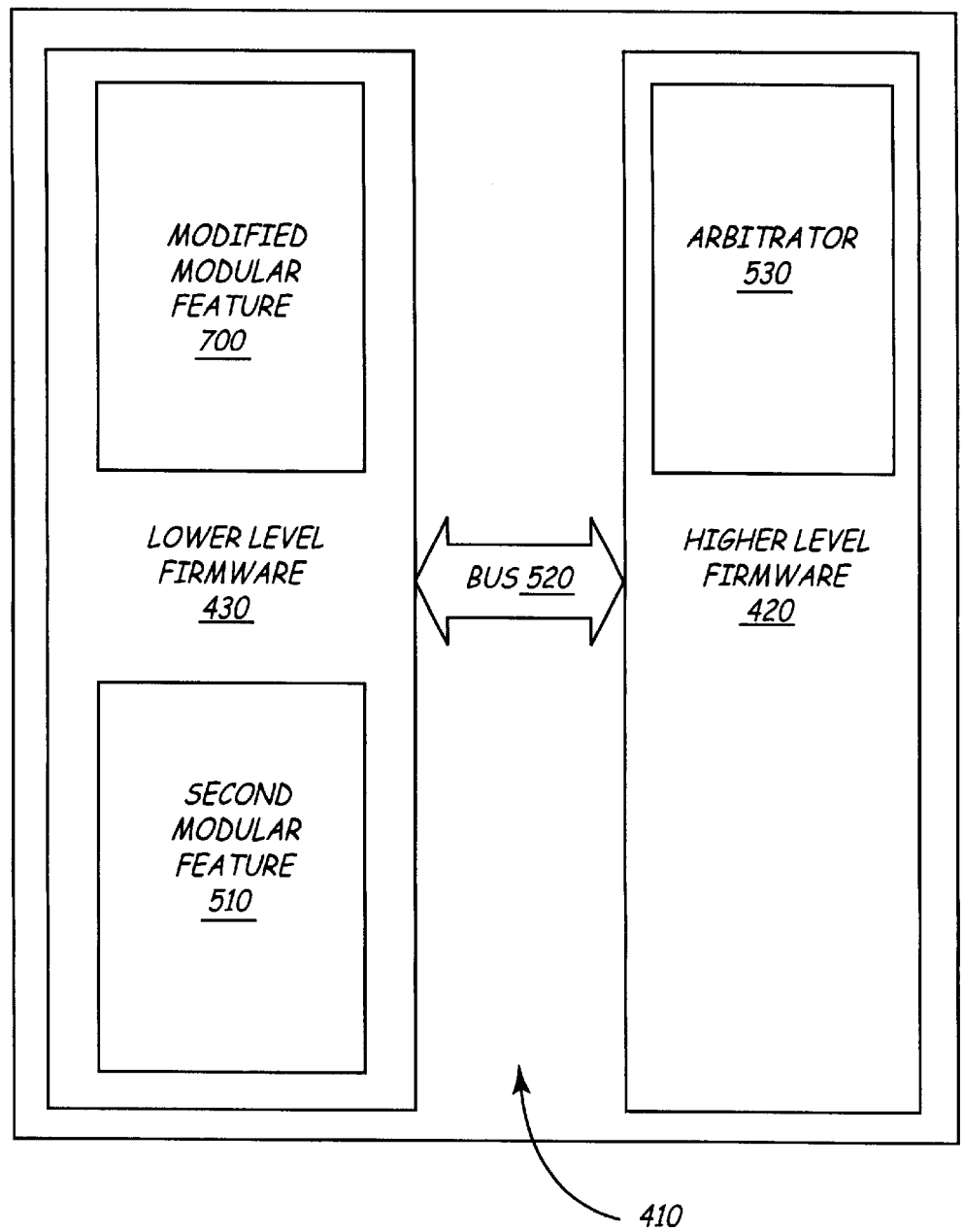
Figure 8:
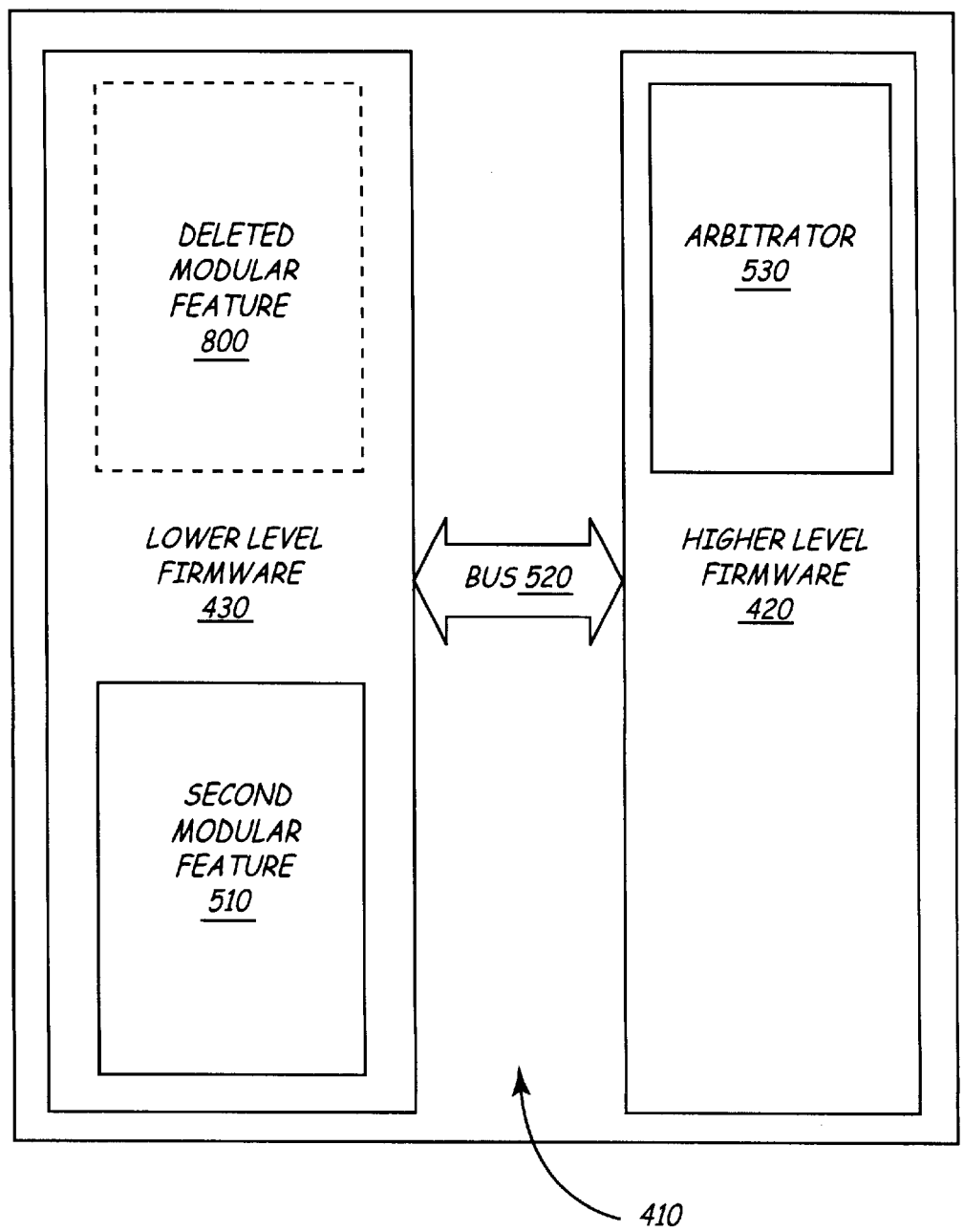

As shown in FIGS. 6–8, controlling the implantable medical device (IMD) 400 using the implantable medical device (IMD) controller 410 may comprise at least one of adding a modular feature to the firmware, modifying a modular feature of the firmware and deleting a modular feature from the firmware. As shown in FIG. 6, for example, controlling the implantable medical device (IMD) 400 using the implantable medical device (IMD) controller 410 may comprise adding a modular feature, such as added modular feature 600, to the lower level firmware 430. As shown in FIG. 7, for example, controlling the implantable medical device (IMD) 400 using the implantable medical device (IMD) controller 410 may comprise modifying a modular feature, such as modified modular feature 700, in the lower level firmware 430. As shown in FIG. 8, for example, controlling the implantable medical device (IMD) 400 using the implantable medical device (IMD) controller 410 may comprise deleting a modular feature, such as deleted modular feature 800 (shown in phantom), from the lower level firmware 430.

The implantable medical device (IMD) controller 410 firmware architecture, described in more detail below, allows modular feature design and implementation. In various illustrative embodiments, the firmware architecture itself, with the higher level firmware 420 communicating with and/or directing the lower level firmware 430 via bus 520, coordinates between and among the plurality of modular features, such as the first modular feature 500 and the second modular feature 510, to reduce feature-to-feature interactions. For example, the firmware architecture may coordinate between and among the first modular feature 500 and the second modular feature 510 to reduce feature-to-feature interactions by testing the first modular feature 500 and/or the second modular feature 510 to debug the first modular feature 500 and/or the second modular feature 510.

Figure 9:
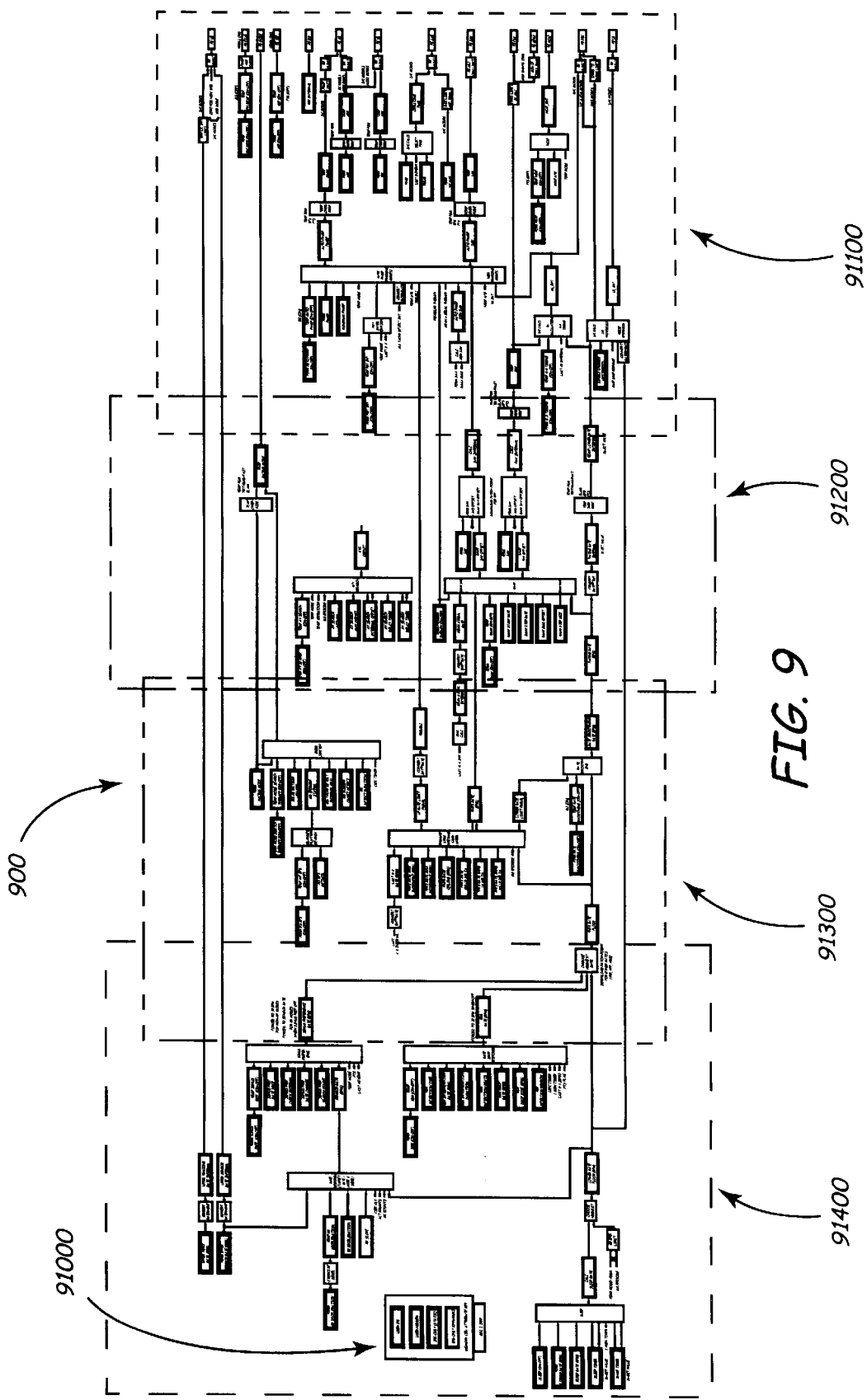
Figure 10:
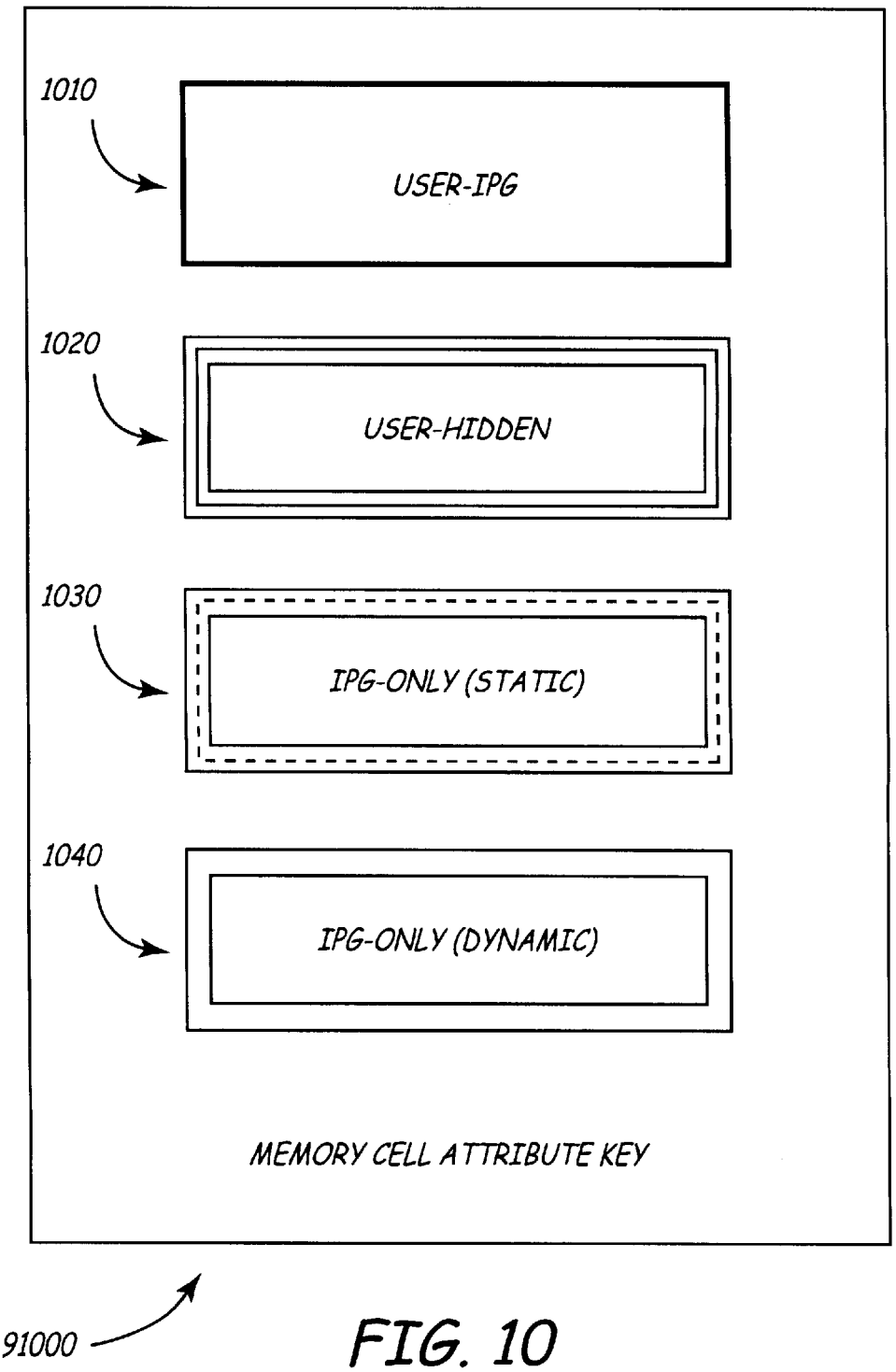
Figure 11A:
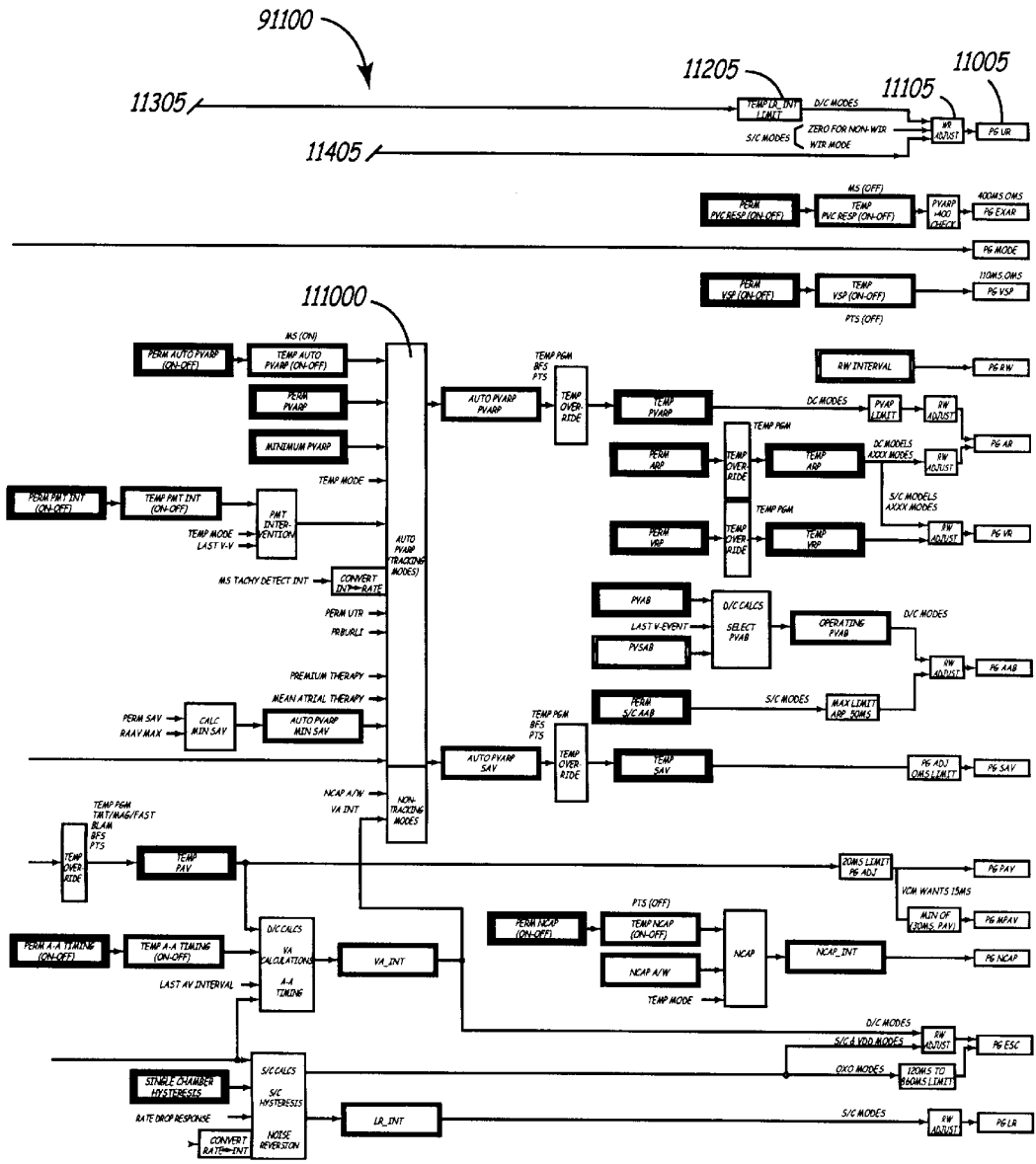
Figure 11C:
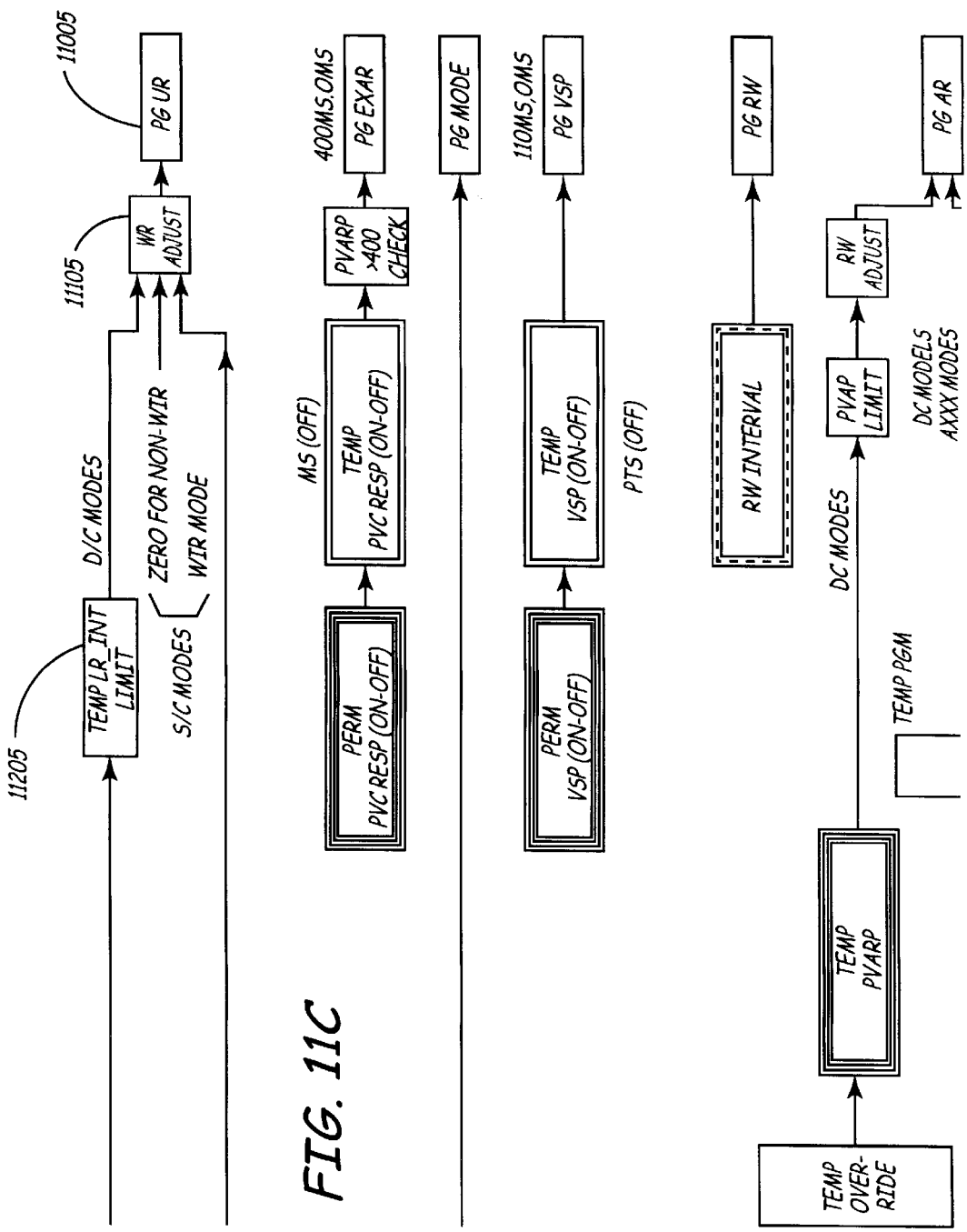
Figure 11D:
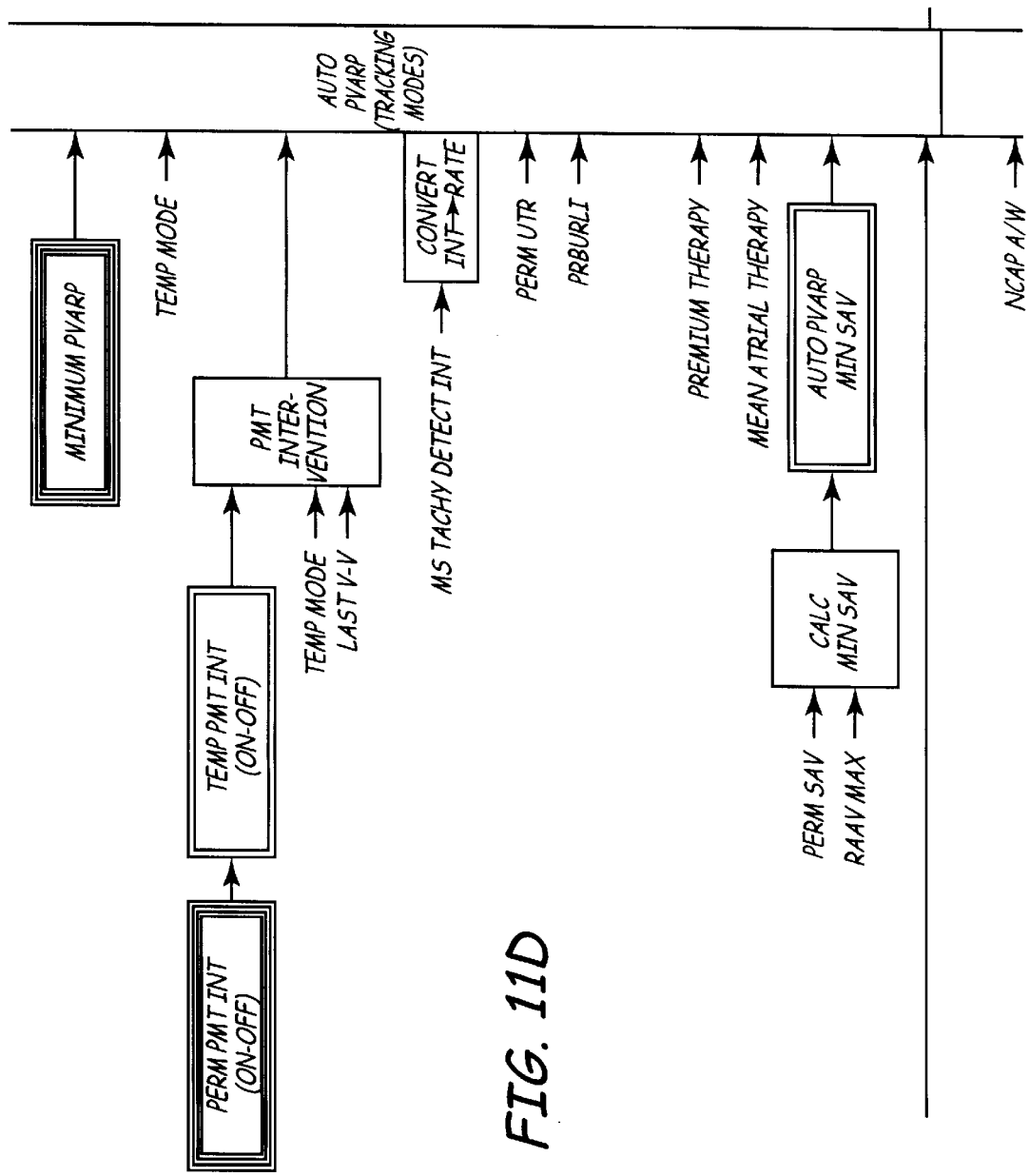
Figure 11E:
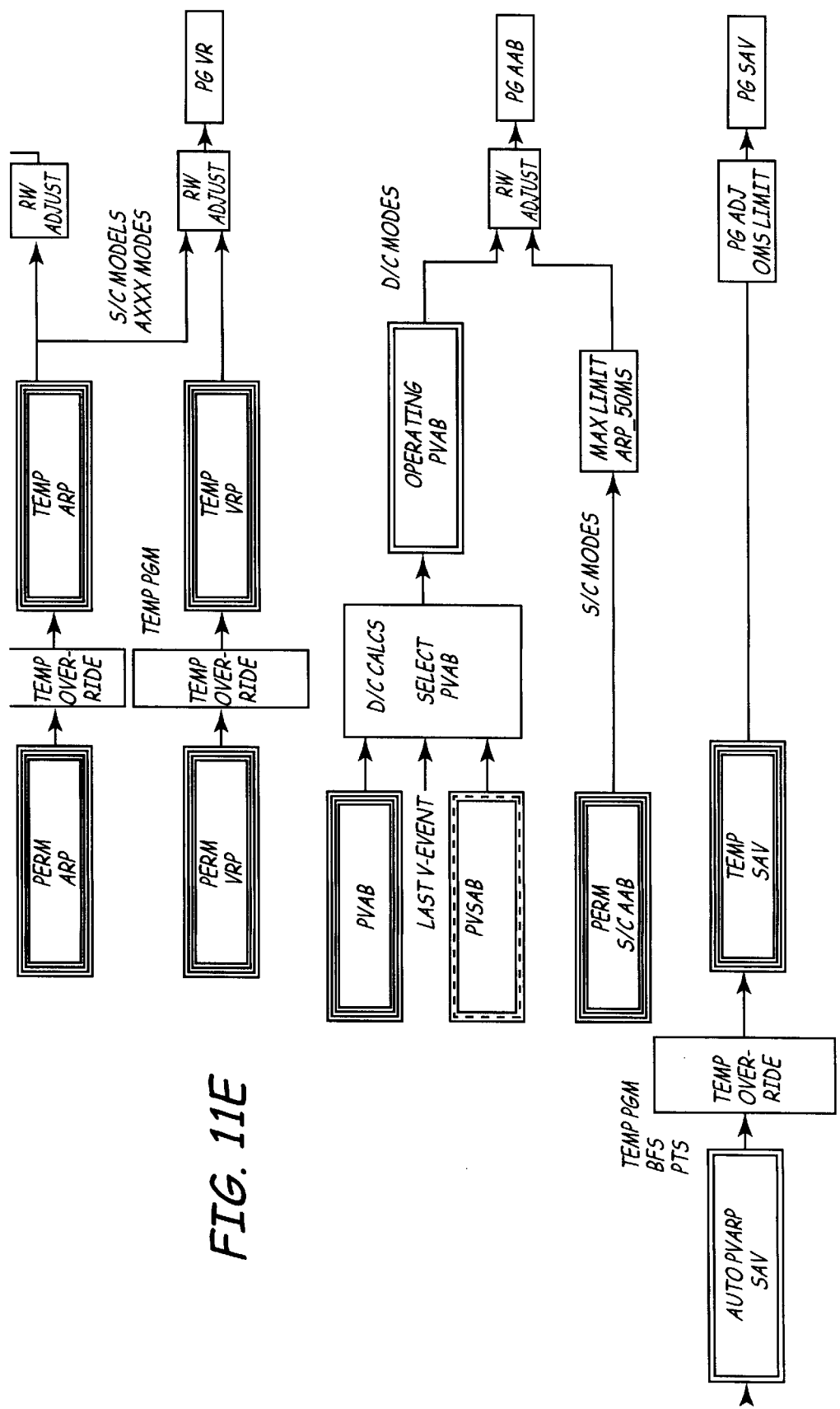
Figure 11F:
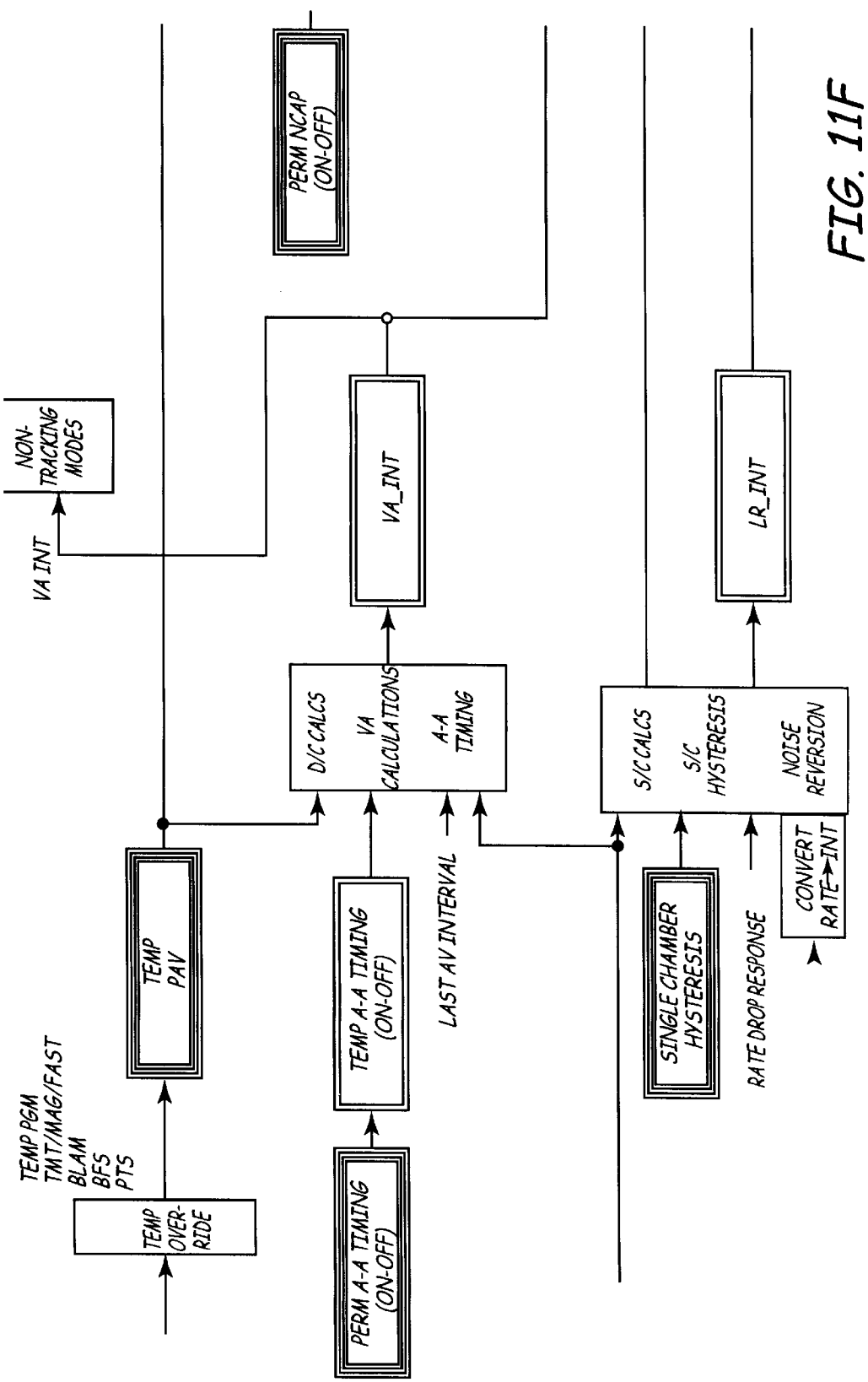
Figure 116:
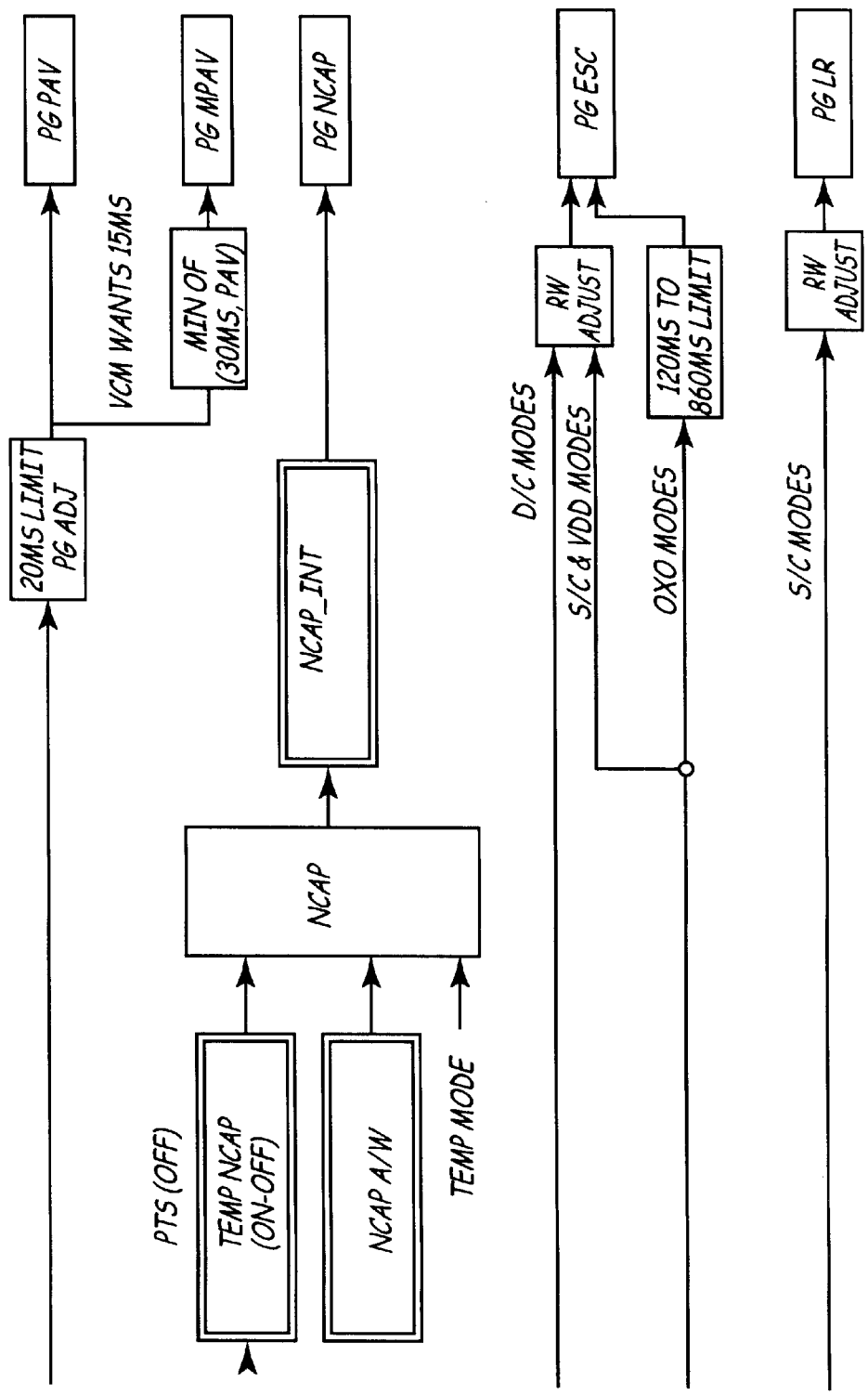

As shown in FIG. 9, a flow diagram 900 for one embodiment of lower level firmware (similar to the lower level firmware 430) for an implantable pacemaker controller (similar to the implantable medical device (IMD) controller 410) is schematically illustrated. FIG. 10 schematically illustrates a key 1000 to attributes of memory cells comprising this embodiment of lower level firmware. Memory cells similar to memory cell 1010 are available to be set and/or determined by a user, whereas memory cells similar to memory cell 1020 are hidden from the user and, thus, not available to be set and/or determined by the user. Memory cells similar to memory cell 1030 are static and unchanged, whereas memory cells similar to memory cell 1040 are dynamic and changeable.

Figure 24:
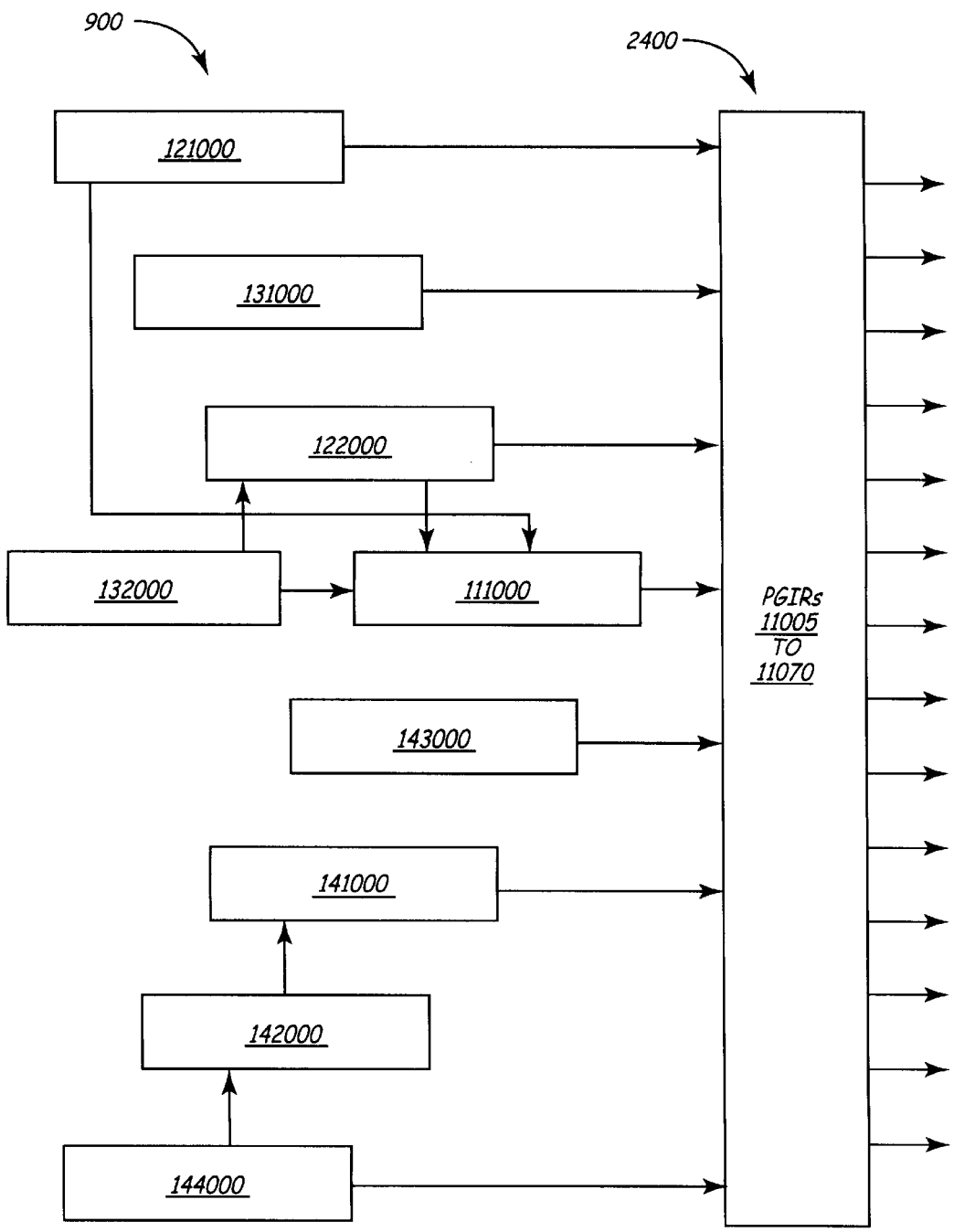
Figure 25:
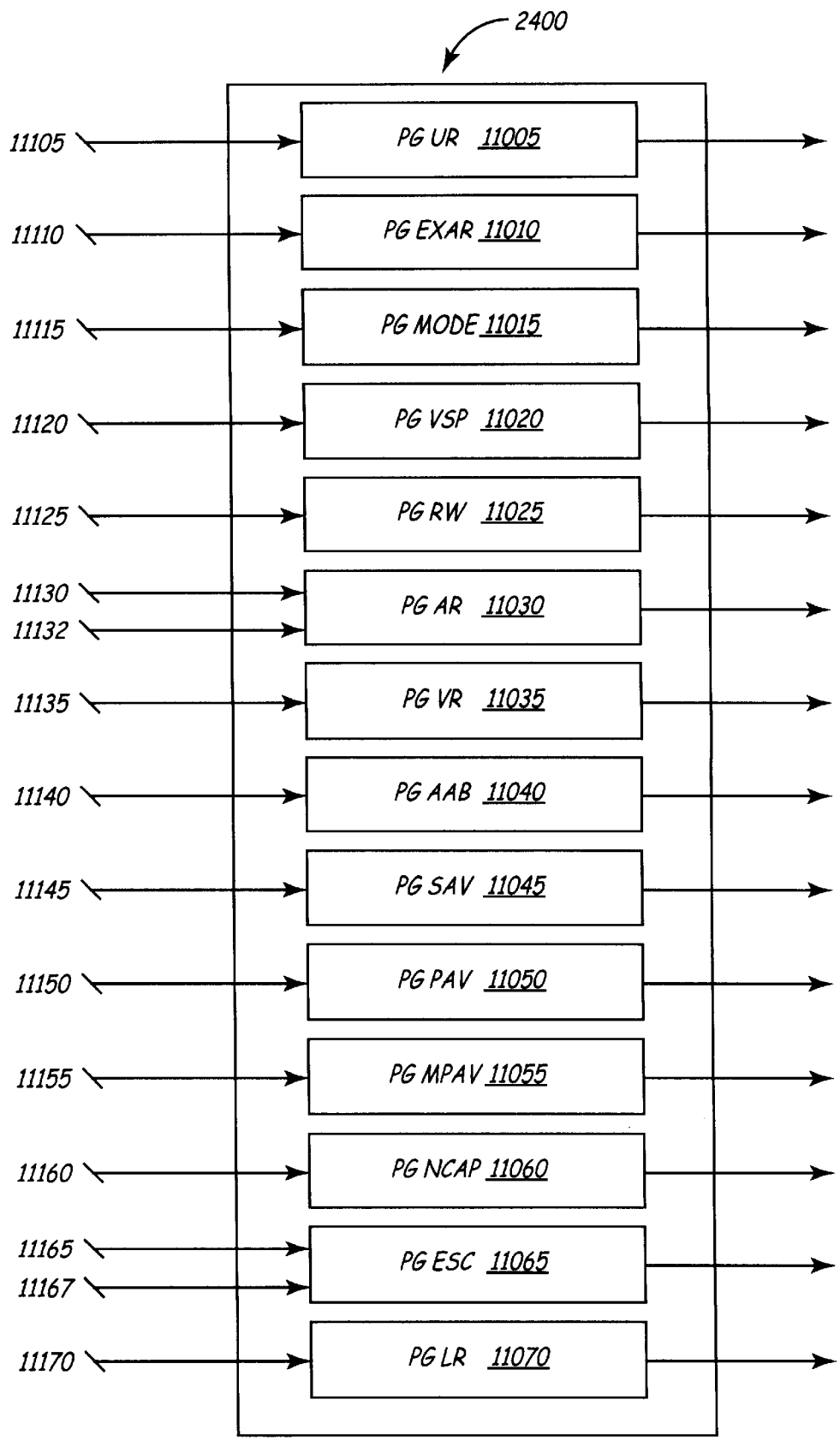

As shown in FIGS. 24 and 25, at the right of the flow diagram 900, as indicated by box 2400, and also shown (unlabeled) in phantom box 91100 of FIG. 9, a number of pulse generator input registers (PGIRs) 11005–11070 (FIGS. 11 and 25) pass on and/or update the values that are input therein every beat. The values passed on and/or updated on a beat-to-beat basis by the pulse generator input registers (PGIRs) 11005–11070 are input to an implantable pulse generator (IPG).

The implantable pulse generator (IPG), an example of a device similar to the implantable medical device (IMD) 400, may be for an implantable pacemaker, such as an implantable anti-brady pacemaker and/or an implantable anti-tachy pacemaker (not shown). The lower part of the flow diagram 900 illustrates modular features that involve determining the proper pacing rate. Other parts of the flow diagram 900 show modular features such as Adaptive Atrial Ventricular (Adaptive AV) 122000 (FIG. 12), Adaptive Post-Ventricular Atrial Refractory Period (Adaptive PVARP) 111000 (FIG. 11) and Mode Switch (MS) 131000 (FIG. 13). The Mode Switch (MS) 131000, for example, involves switching from a mode of tracking atrial contractions to a mode on not tracking atrial contractions, because of Atrial Fibrillation (AF) or Atrial flutter (Afl), and the like).

Modular features on the left side of the flow diagram 900 operate in the "rate domain," where calculations are performed in units of beats per minute (bpm). Using 8-bit values for these calculations can provide a resolution of 1 beat per minute (1 bpm) steps over a range from 0 bpm to 255 bpm ($2^8$=256), which is acceptable for brady and tachy therapy applications. In alternative illustrative embodiments, 16-bit values for calculations may be used that can provide a resolution of 1 operation per minute (1 oppm) steps over a range from 0 oppm to 65535 oppm ($2^{16}$=65536), which is acceptable for certain types of neurological therapy applications. Pacing rate modular features such as Atrial Pacing Preference (APP), Atrial Rate Stabilization (ARS) and Ventricular Rate Stabilization (VRS) can easily be added to the left side of the flow diagram 900 and be part of the pacing rate decision process.

Some modular features output a desired pacing rate, and a higher level firmware "arbitrator" (such as firmware arbitrator 530 disposed in the higher level firmware 420, as shown in FIG. 5) may decide to use the desired pacing rate output by the modular feature or use another value from a different modular feature. In the simplest form, the highest pacing rate is chosen by the higher level firmware arbitrator. In a more complex form, a higher pacing rate may lose priority to some modular feature that has a lower pacing rate. Some modular features output an offset value, and a higher level firmware operation may combine some or all of the offset values, for example, as in Atrial Ventricular (AV) adaptation. Some modular features may pass through one or more parameter values, either unmodified or modified, for example, as in the Sensing Atrial Ventricular (SAV) parameter value passing through the Auto Post-Ventricular Atrial Refractory Period (PVARP) 111000 (FIG. 11) algorithm.

During temporary operation, key pacing therapy parameters, such as Mode, Escape Interval, Pacing Atrial Ventricular (PAV) interval, Sensing Atrial Ventricular (SAV) interval, Post-Ventricular Atrial Refractory Period (PVARP), and the like, are held at static values and are not modified by modular features in the therapy flow. Consequently, modular features do not have to be disabled during temporary operations.

Each modular feature, such as the first modular feature 500 and the second modular feature 510, may be a firmware subroutine, for example, in the lower level firmware 430. Each modular feature firmware subroutine may be called by the higher level firmware 420. When each modular feature is called by the higher level firmware 420, the modular feature first checks to see if that particular modular feature is programmed to be "on," and then checks for mode pertinency. That particular modular feature algorithm continues to run if, and only if, all the checks pass (that particular modular feature is programmed to be "on" and is pertinent). Otherwise, that particular modular feature outputs a characteristic default value, such as the relevant rate or offset value, and/or an unmodified value, and ends.

As shown in FIGS. 9, 11 and 25, the pulse generator input registers (PGIRs) 11005–11070 at the right of the flow diagram 900, in the box 2400 in FIGS. 24 and 25, are described in more detail as follows. The pulse generator input register 11005 (PG UR) inputs the upper rate (UR) pacing interval value to the implantable pulse generator (IPG). The pulse generator input register 11005 (PG UR) receives input from line 11105. The pulse generator input register 11010 (PG EXAR) inputs the extreme atrial refractory (EXAR) values (for example, 400 ms and 0 ms) to the implantable pulse generator (IPG). The pulse generator input register 11010 (PG EXAR) receives input from line 11110. The pulse generator input register 11015 (PG MODE) inputs the mode (MODE) value to the implantable pulse generator (IPG). The pulse generator input register 11015 (PG MODE) receives input from line 11115. The pulse generator input register 11020 (PG VSP) inputs the ventricular safety period (VSP) values (for example, 110 ms and 0 ms) to the implantable pulse generator (IPG). The pulse generator input register 11020 (PG VSP) receives input from line 11120. The pulse generator input register 11025 (PG RW) inputs the register write (RW) value (a period of time for loading the pacing engine) to the implantable pulse generator (IPG). The pulse generator input register 11025 (PG RW) receives input from line 11125.

The pulse generator input register 11030 (PG AR) inputs the atrial refractory period (AR) value to the implantable pulse generator (IPG). The pulse generator input register 11030 (PG AR) receives input from lines 11130 and 11132. The pulse generator input register 11035 (PG VR) inputs the ventricular refractory period (VR) value to the implantable pulse generator (IPG). The pulse generator input register 11035 (PG VR) receives input from line 11135. The pulse generator input register 11040 (PG AAB) inputs the adaptive atrial blanking period (AAB) value to the implantable pulse generator (IPG). The pulse generator input register 11040 (PG AAB) receives input from line 11140. The pulse generator input register 11045 (PG SAV) inputs the sensing atrial ventricular interval (SAV) value to the implantable pulse generator (IPG). The pulse generator input register 11045 (PG SAV) receives input from line 11145. The pulse generator input register 11050 (PG PAV) inputs the pacing atrial ventricular interval (PAV) value to the implantable pulse generator (IPG). The pulse generator input register 11050 (PG PAV) receives input from line 11150.

The pulse generator input register 11055 (PG MPAV) inputs the minimum pacing atrial ventricular interval (MPAV) value to the implantable pulse generator (IPG). The pulse generator input register 11055 (PG MPAV) receives input from line 11155. The pulse generator input register 11060 (PG NCAP) inputs the non-competitive atrial pacing interval (NCAP) value to the implantable pulse generator (IPG). The pulse generator input register 11060 (PG NCAP) receives input from line 11160. The pulse generator input register 11065 (PG ESC) inputs the escape interval (ESC) value to the implantable pulse generator (IPG). The pulse generator input register 11065 (PG ESC) receives input from lines 11165 and 11167. Finally, the pulse generator input register 11070 (PG LR) inputs the lower rate (LR) pacing interval value the implantable pulse generator (IPG). The pulse generator input register 11070 (PG LR) receives input from line 11170.

Figure 12A:
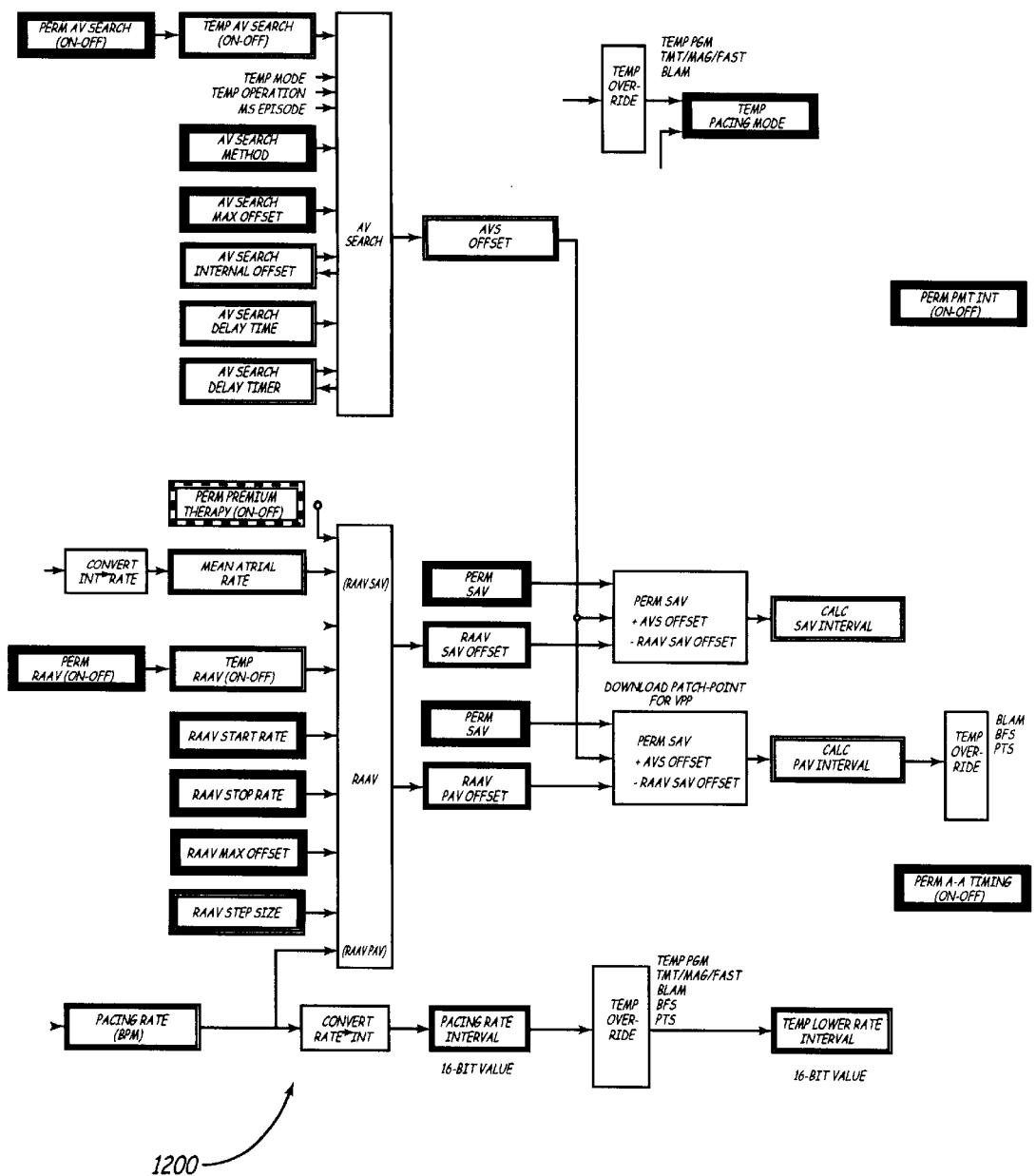
Figure 12B:
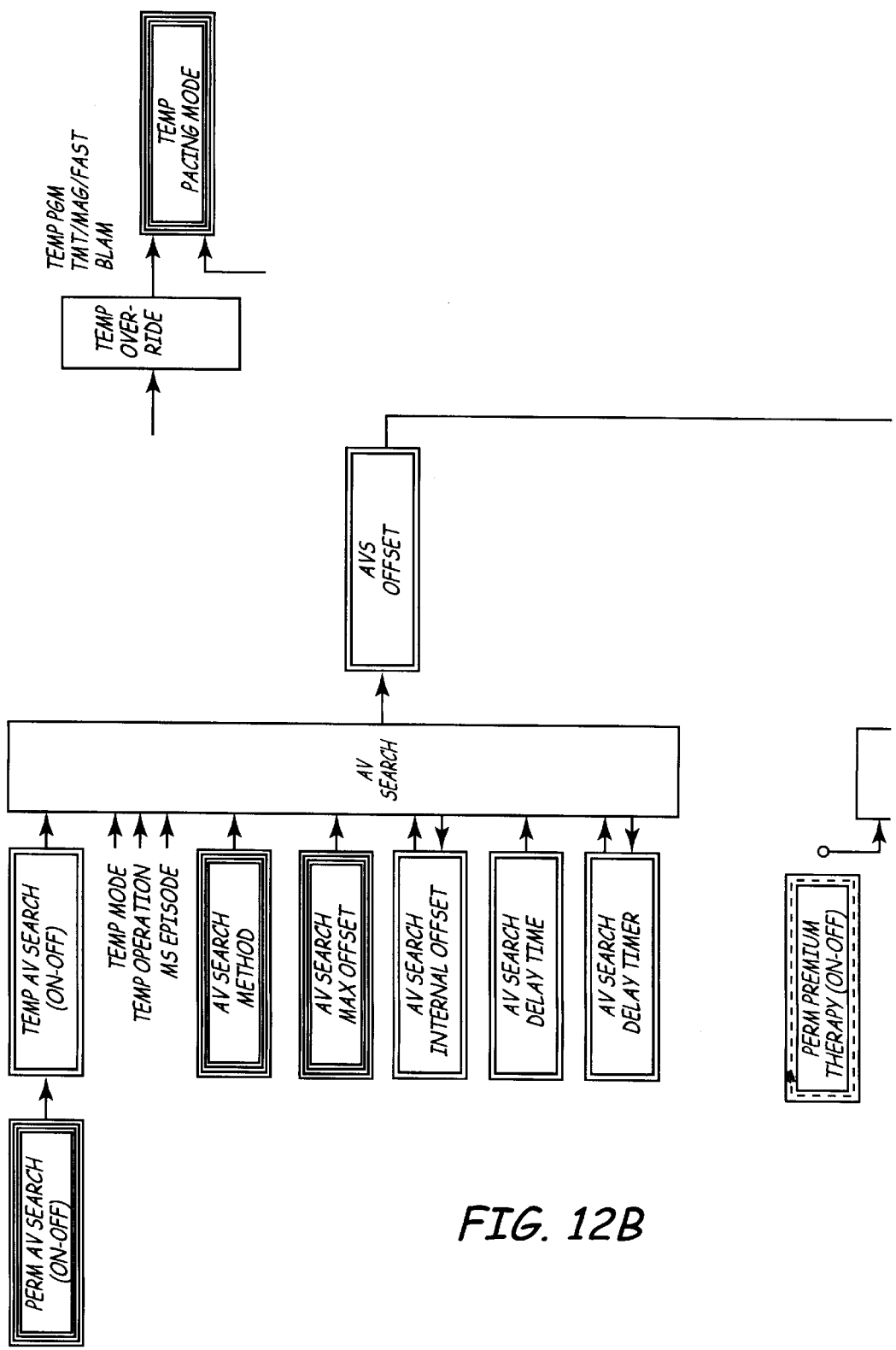
Figure 12C:
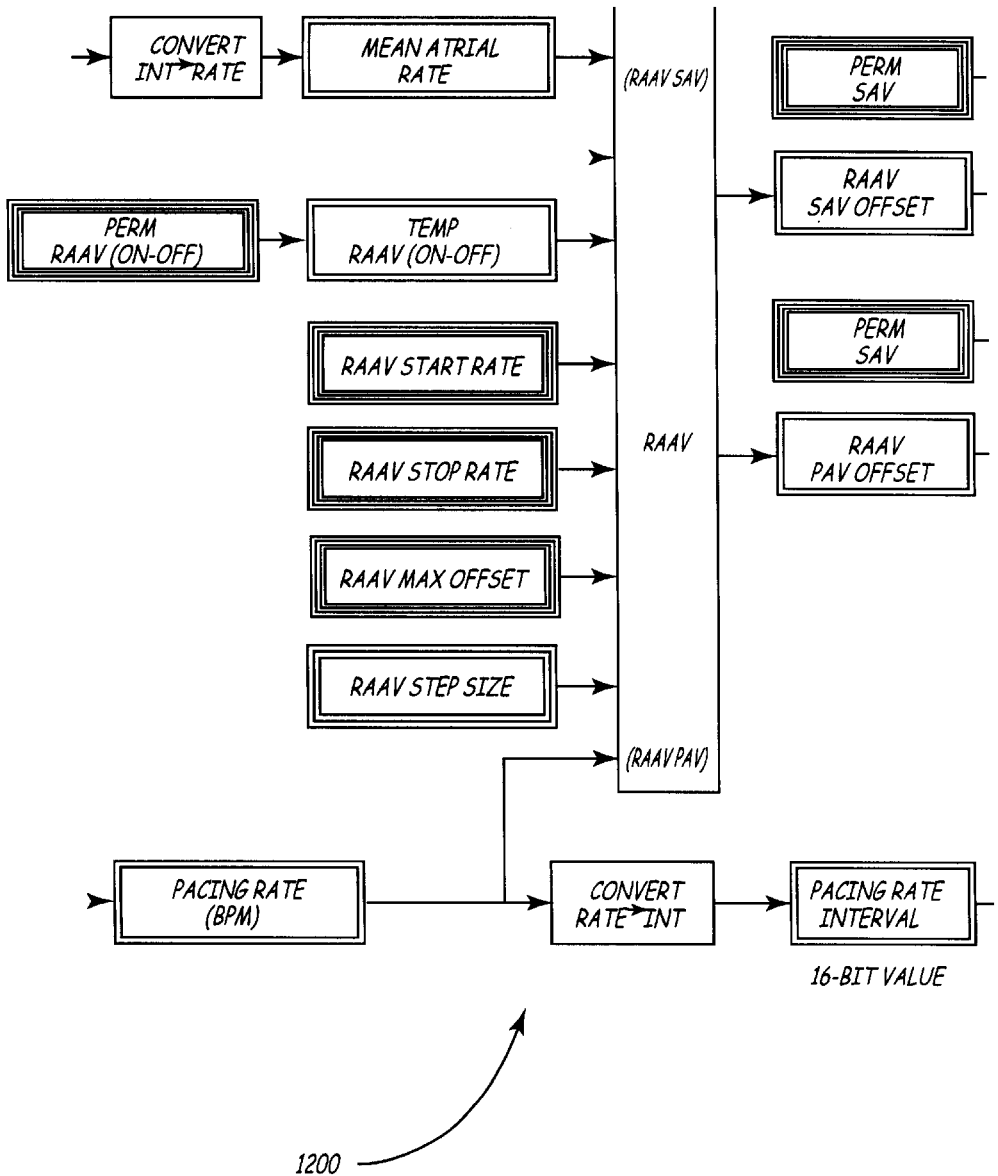
Figure 13A:
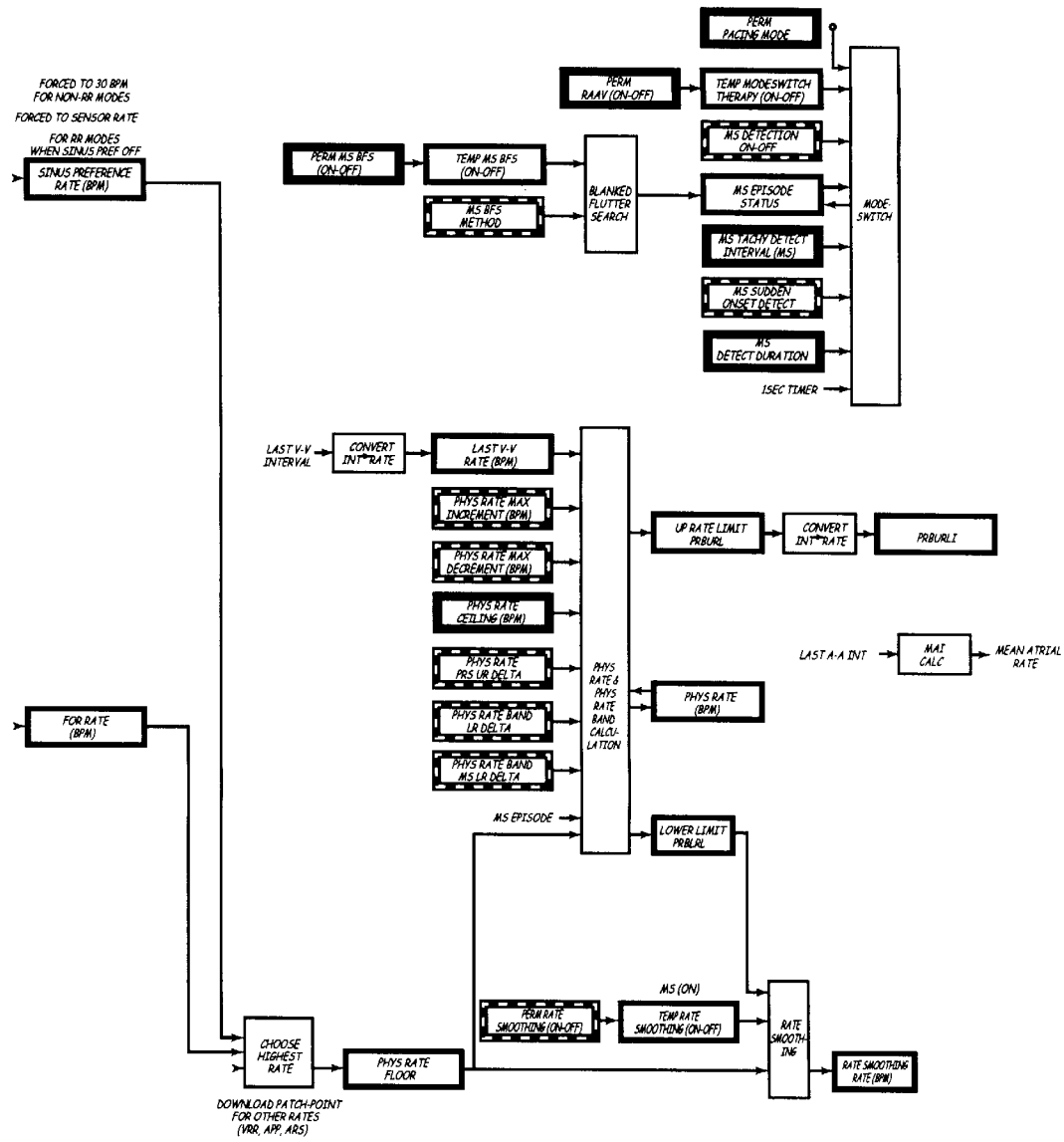
Figure 13B:
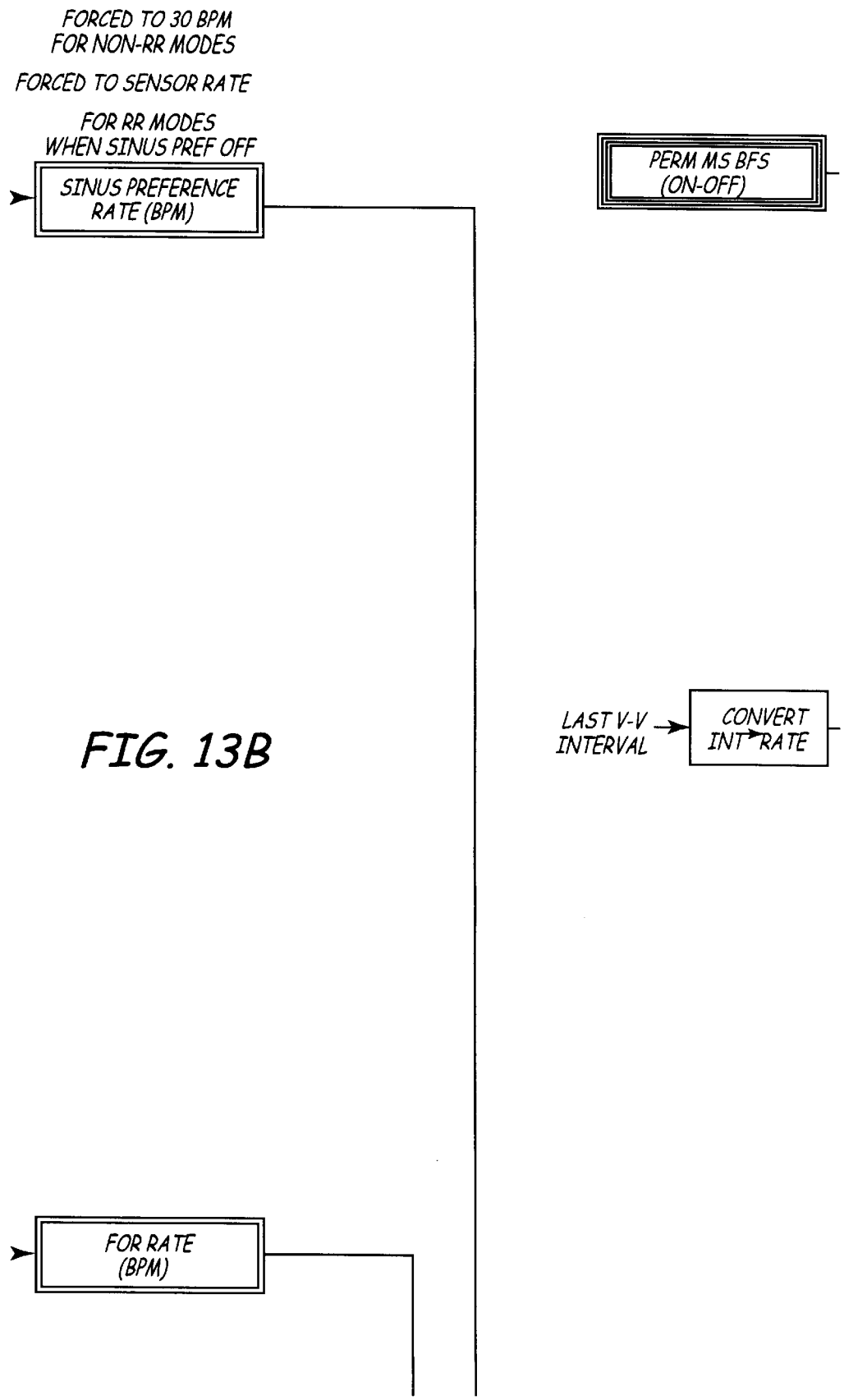
Figure 13C:
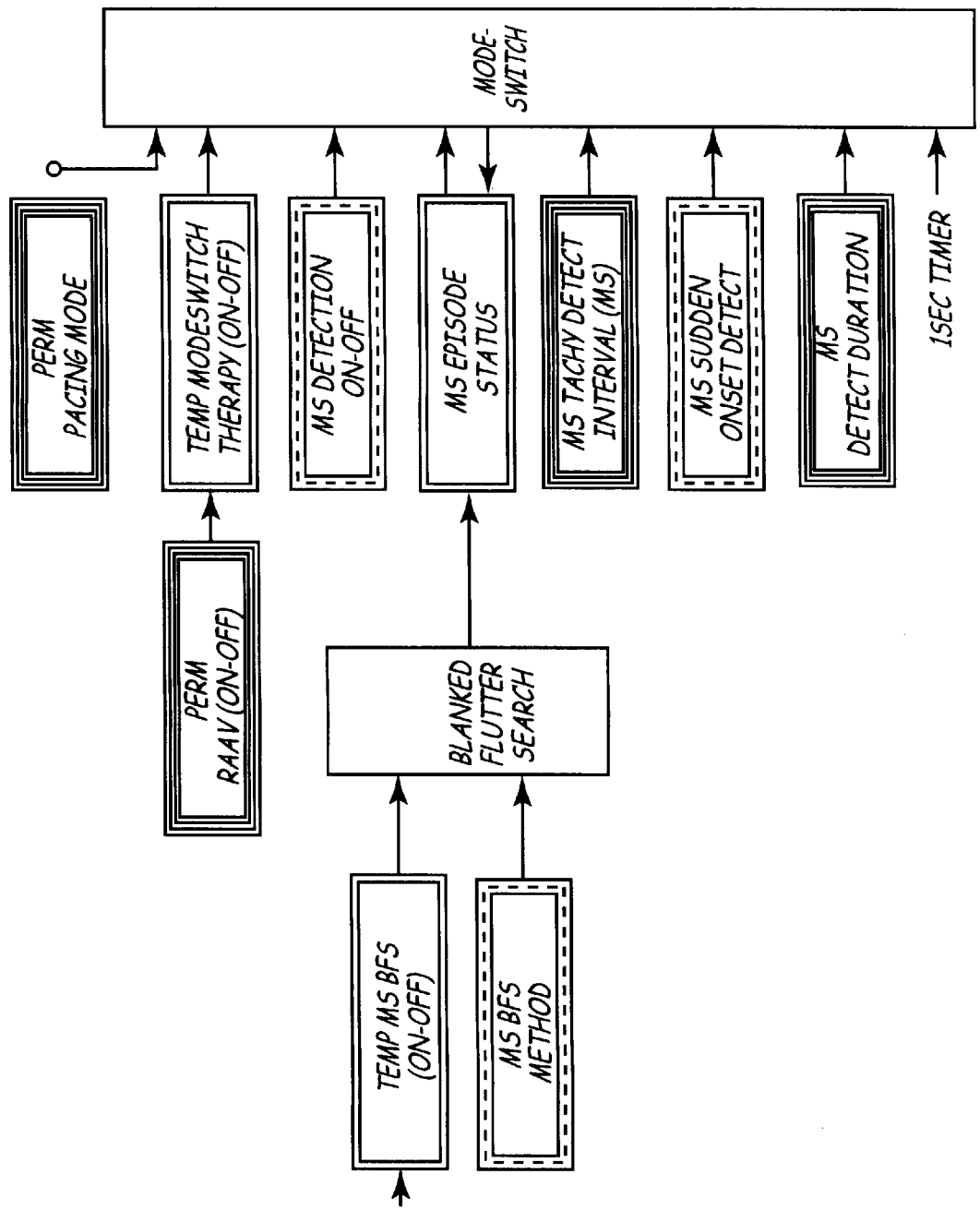
Figure 13D:
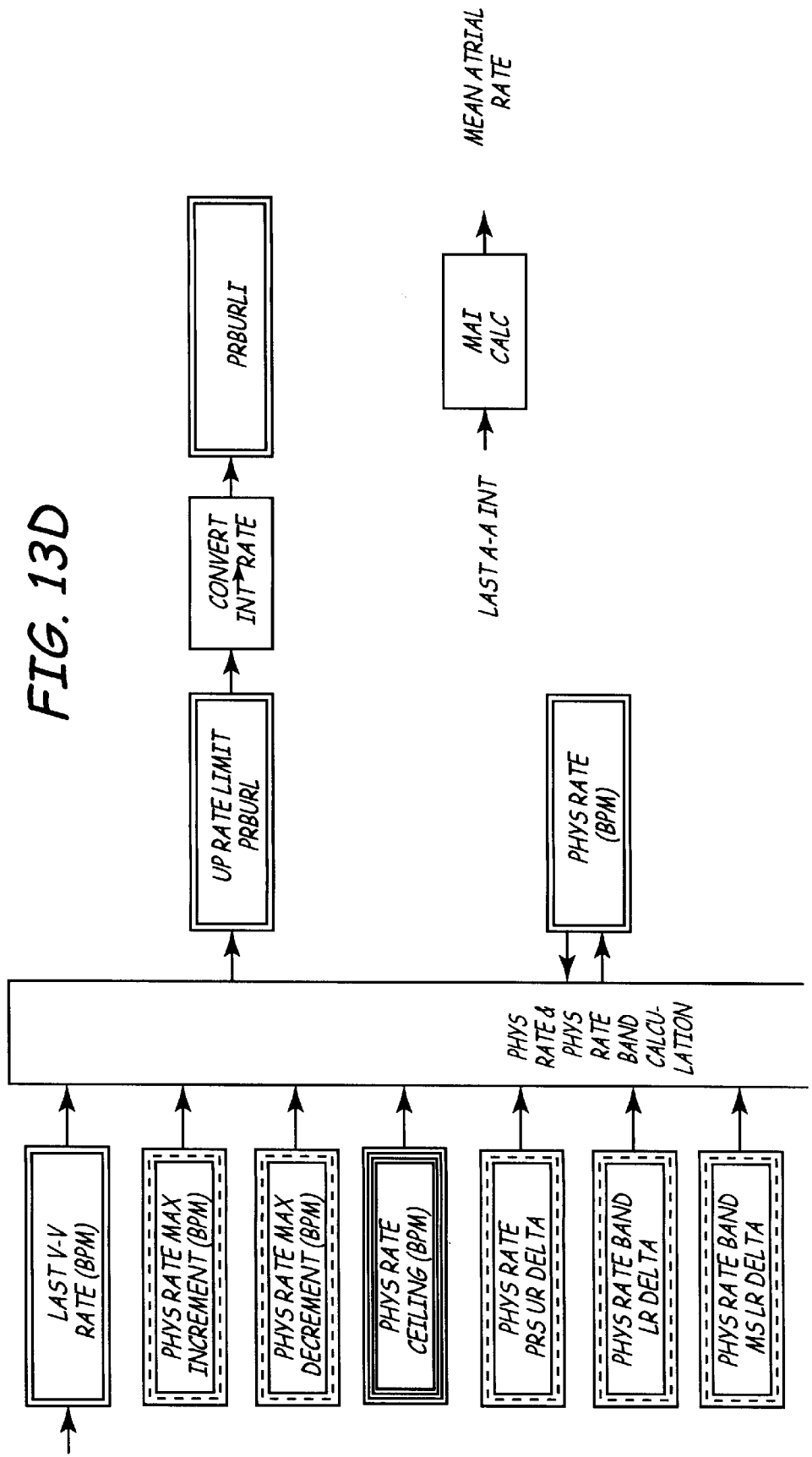
Figure 13E:
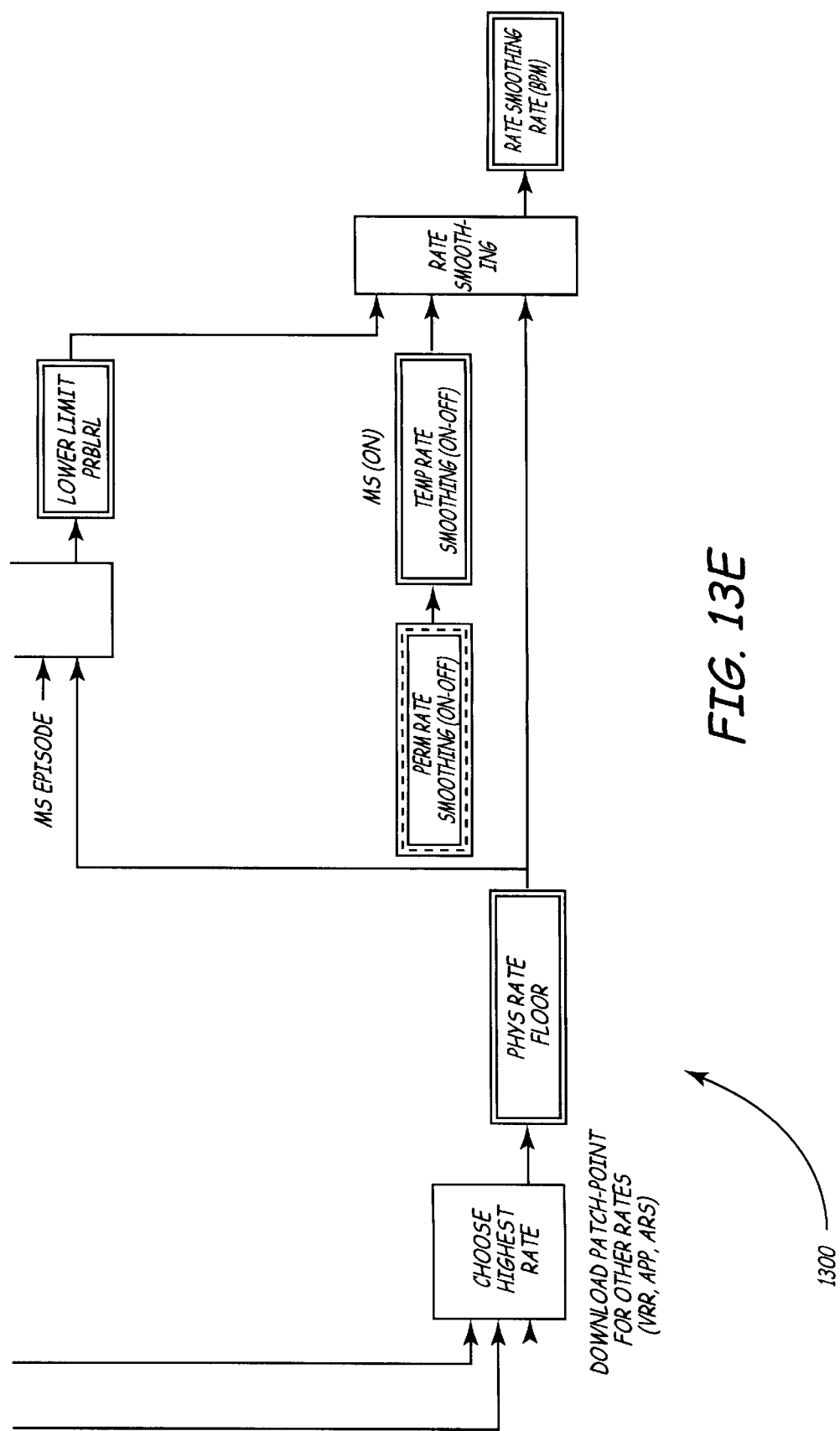
Figure 14A:
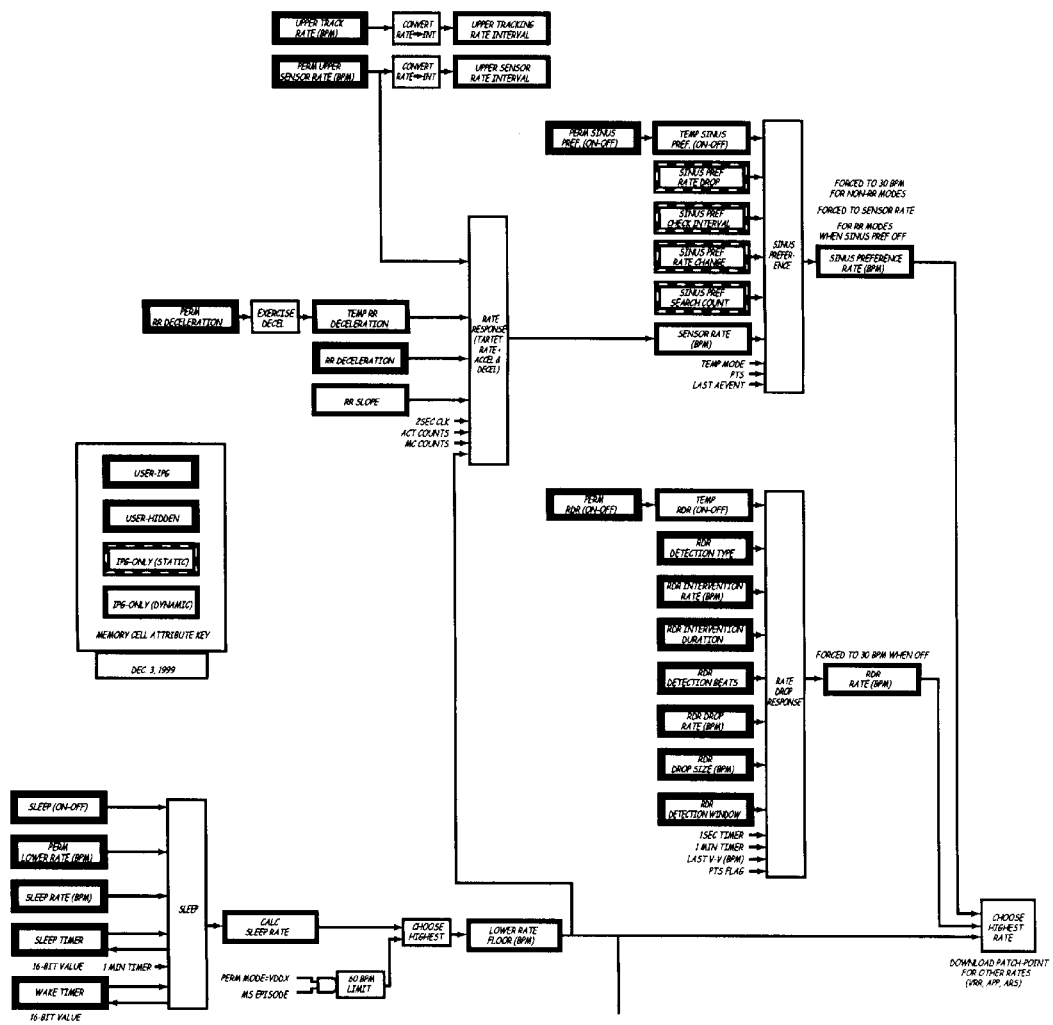
Figure 14B:
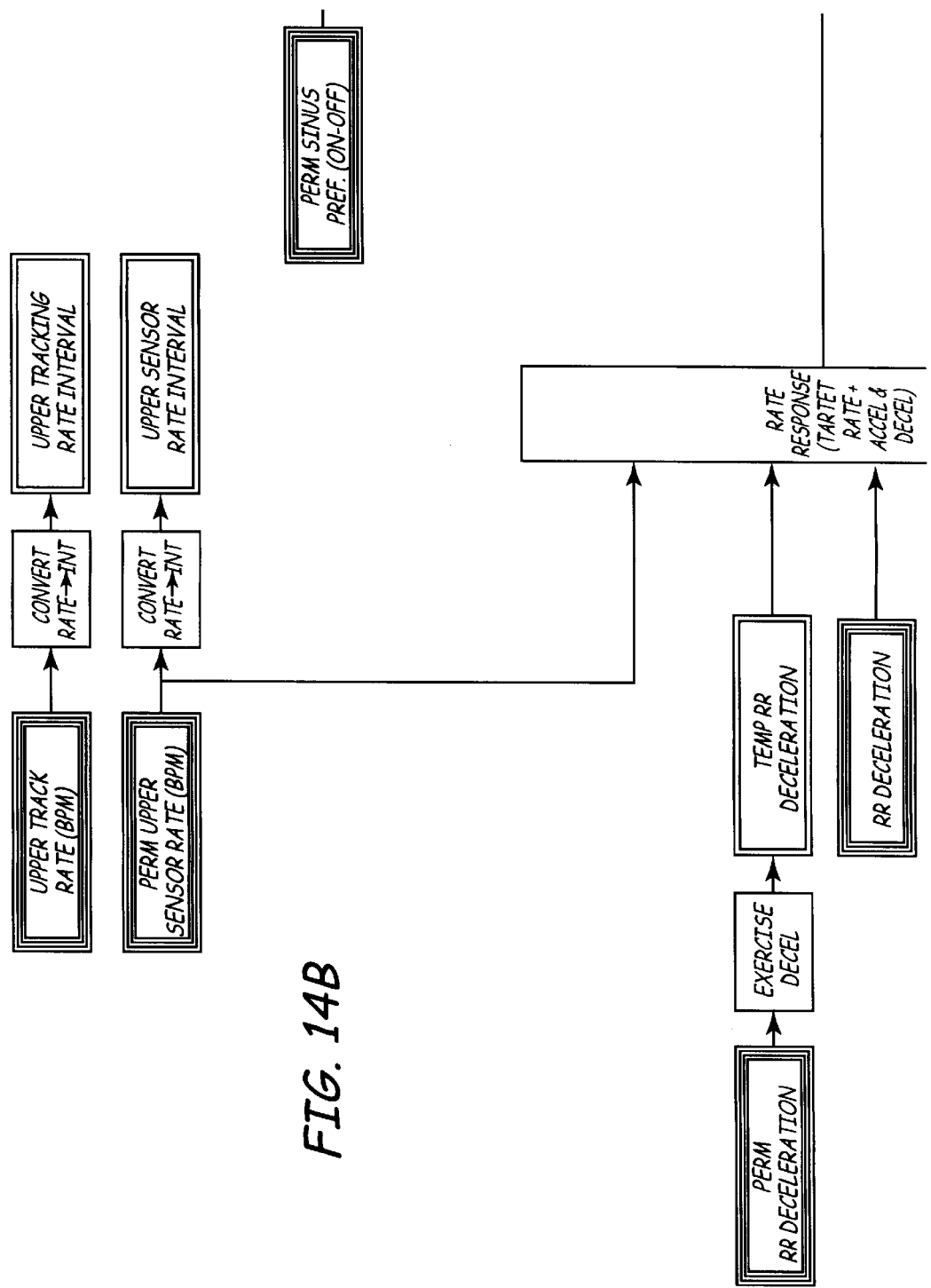
Figure 14E:
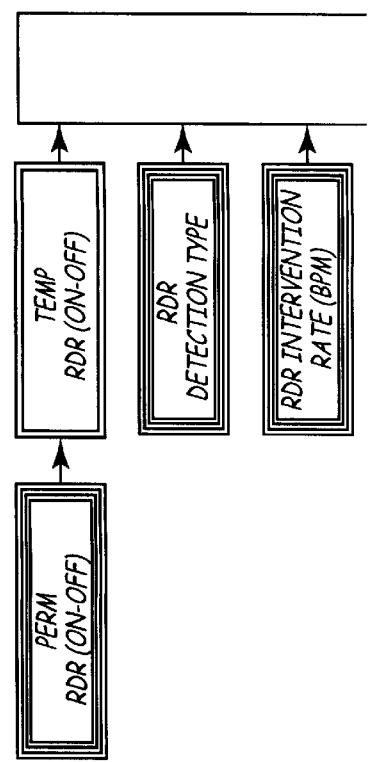
Figure 14F:
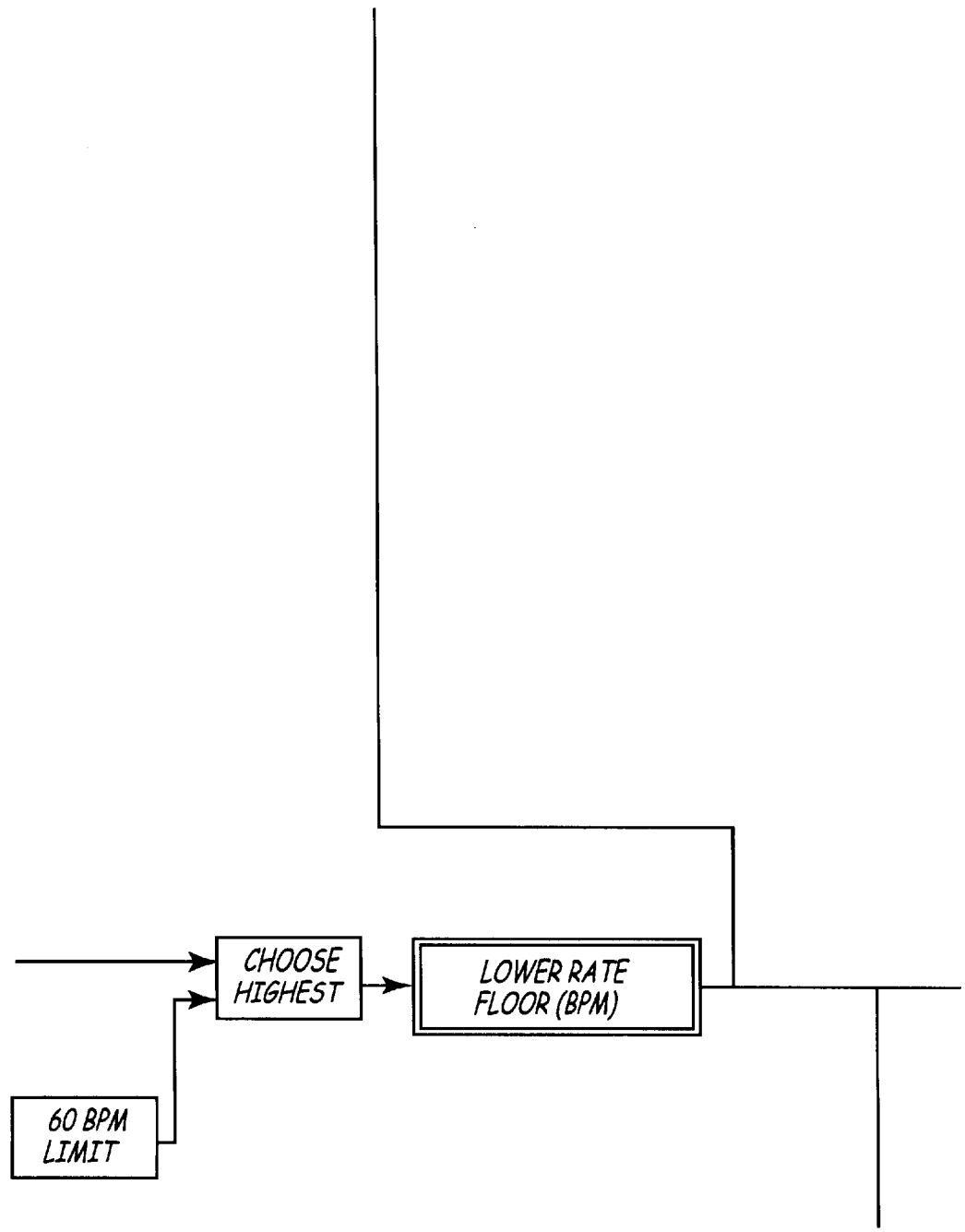
Figure 17A:
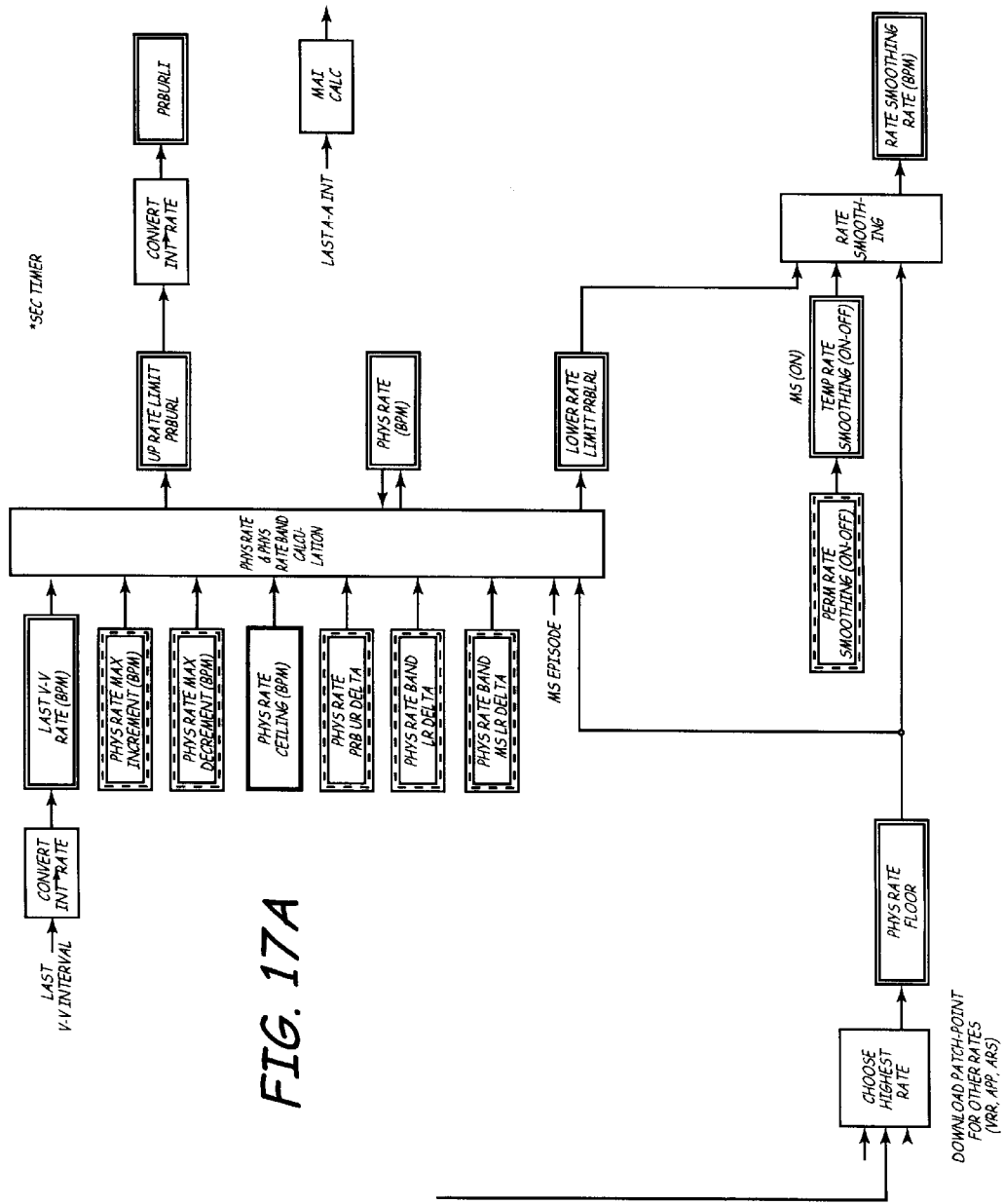
Figure 17B:
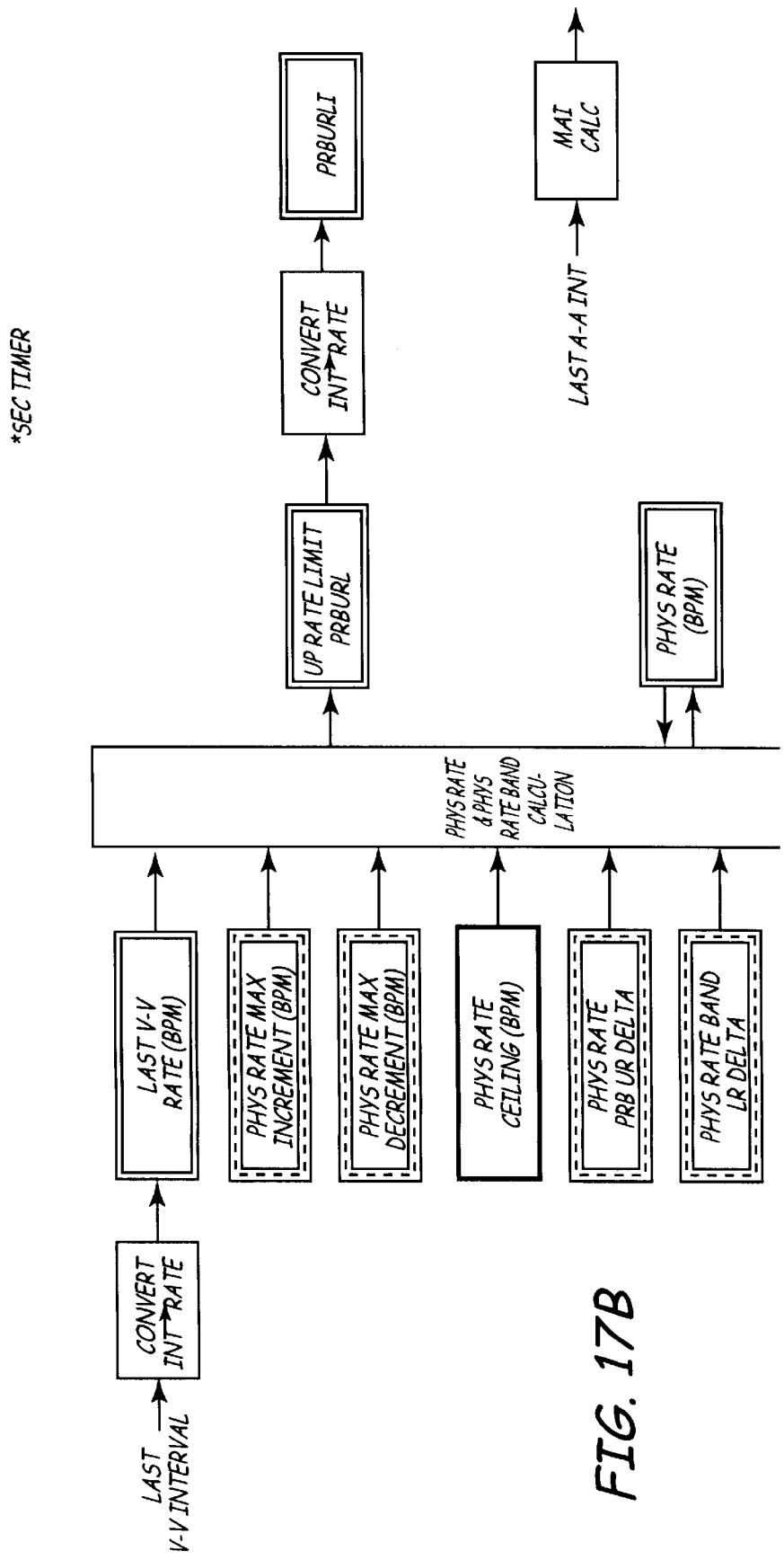
Figure 17C:
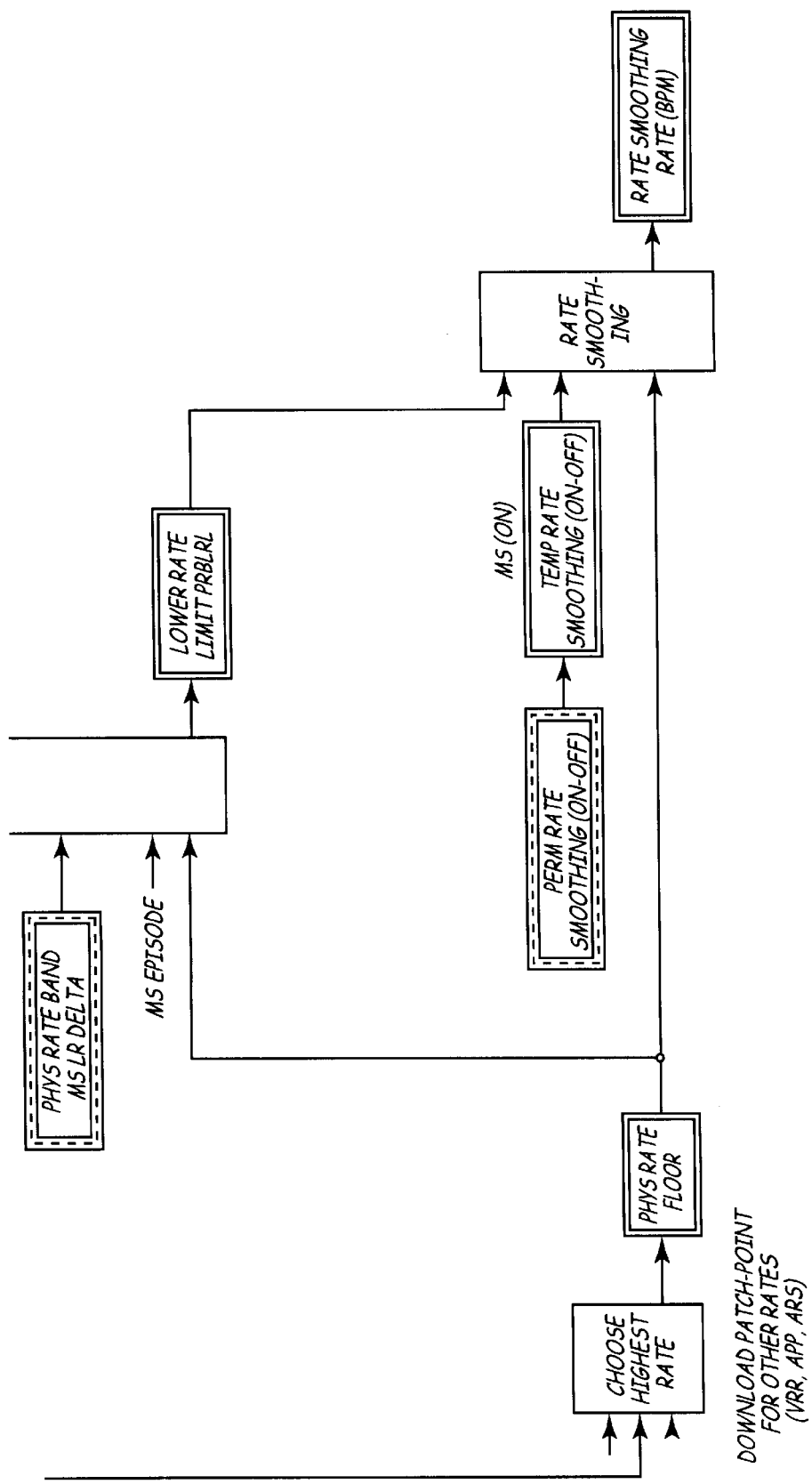
Figure 19:
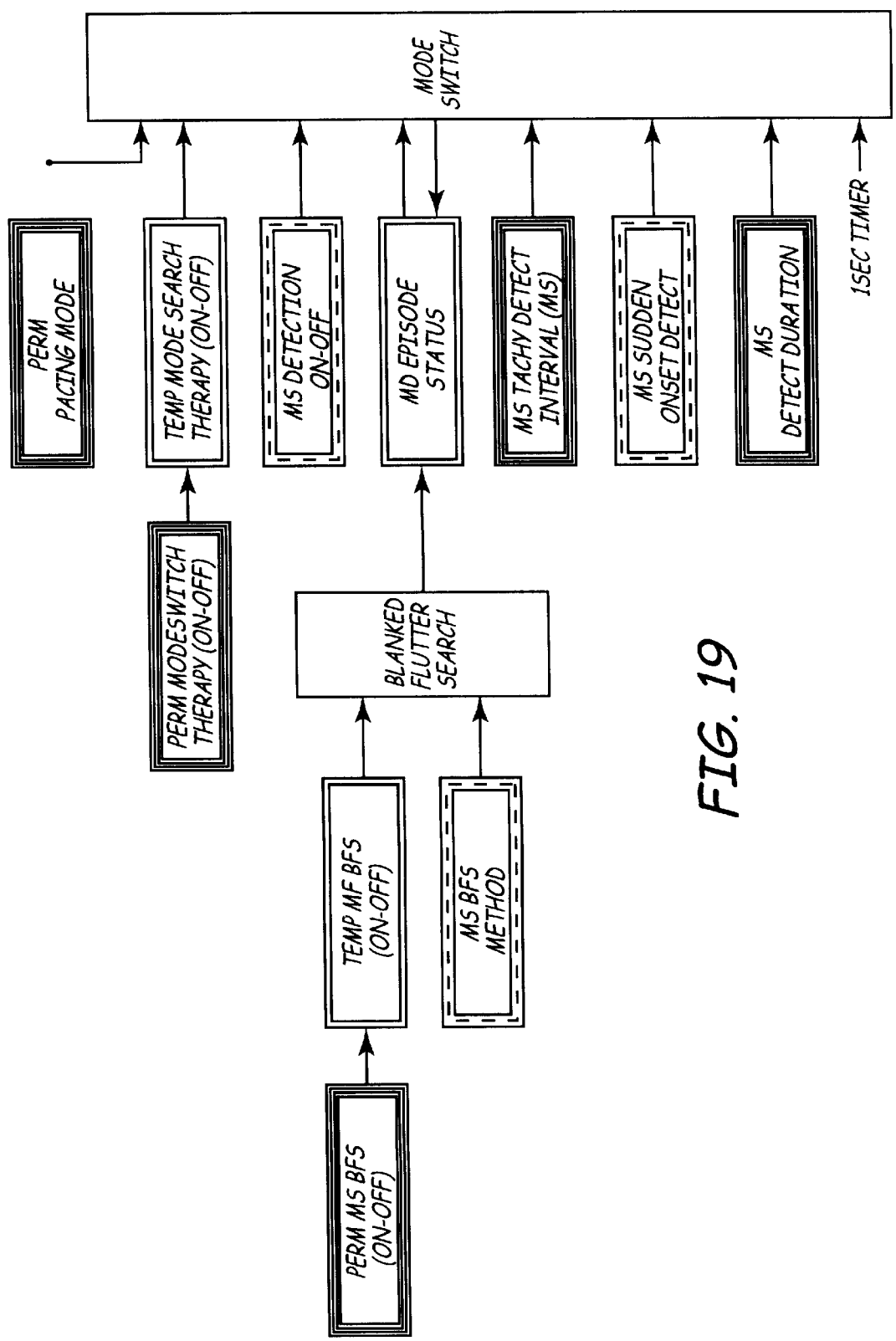
Figure 20:
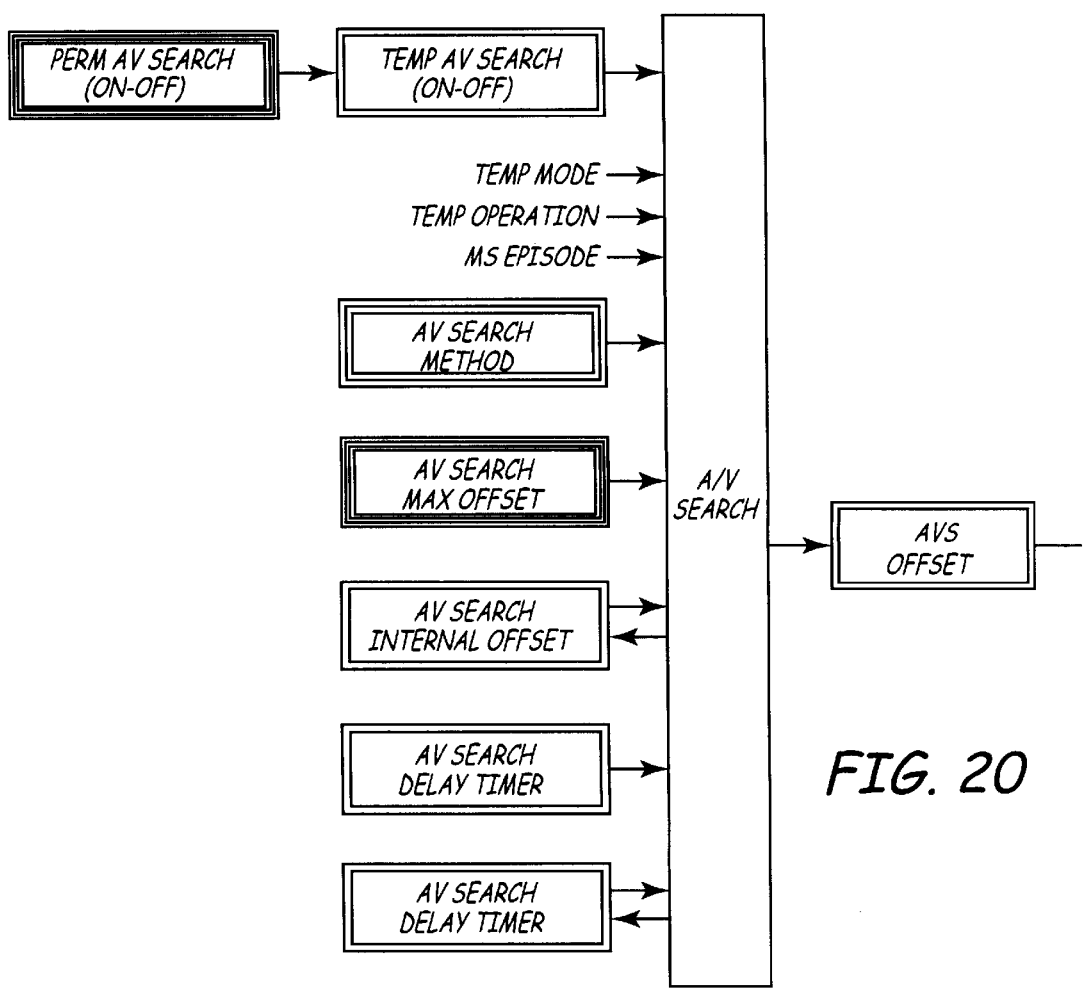
Figure 21A:
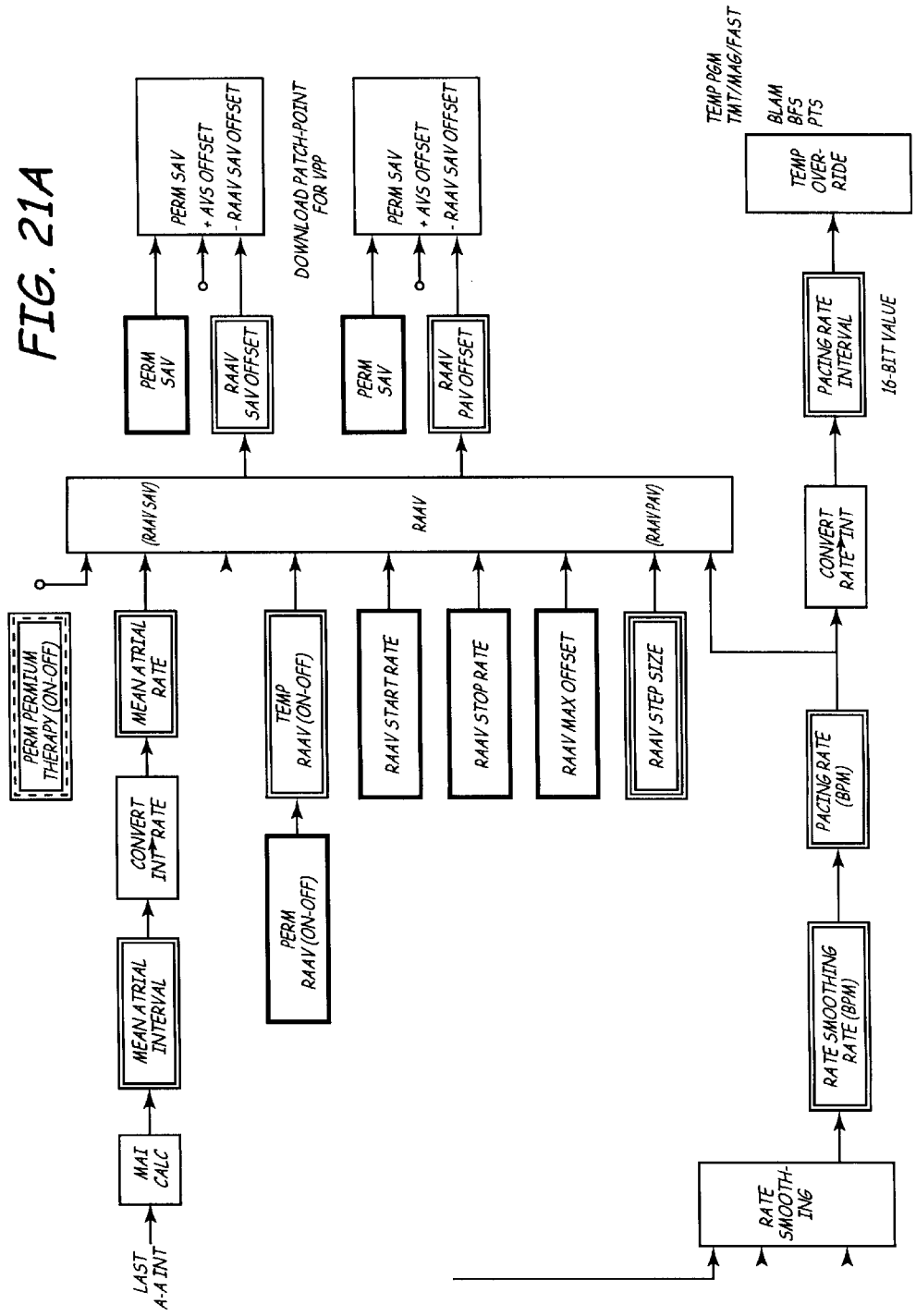
Figure 21B:
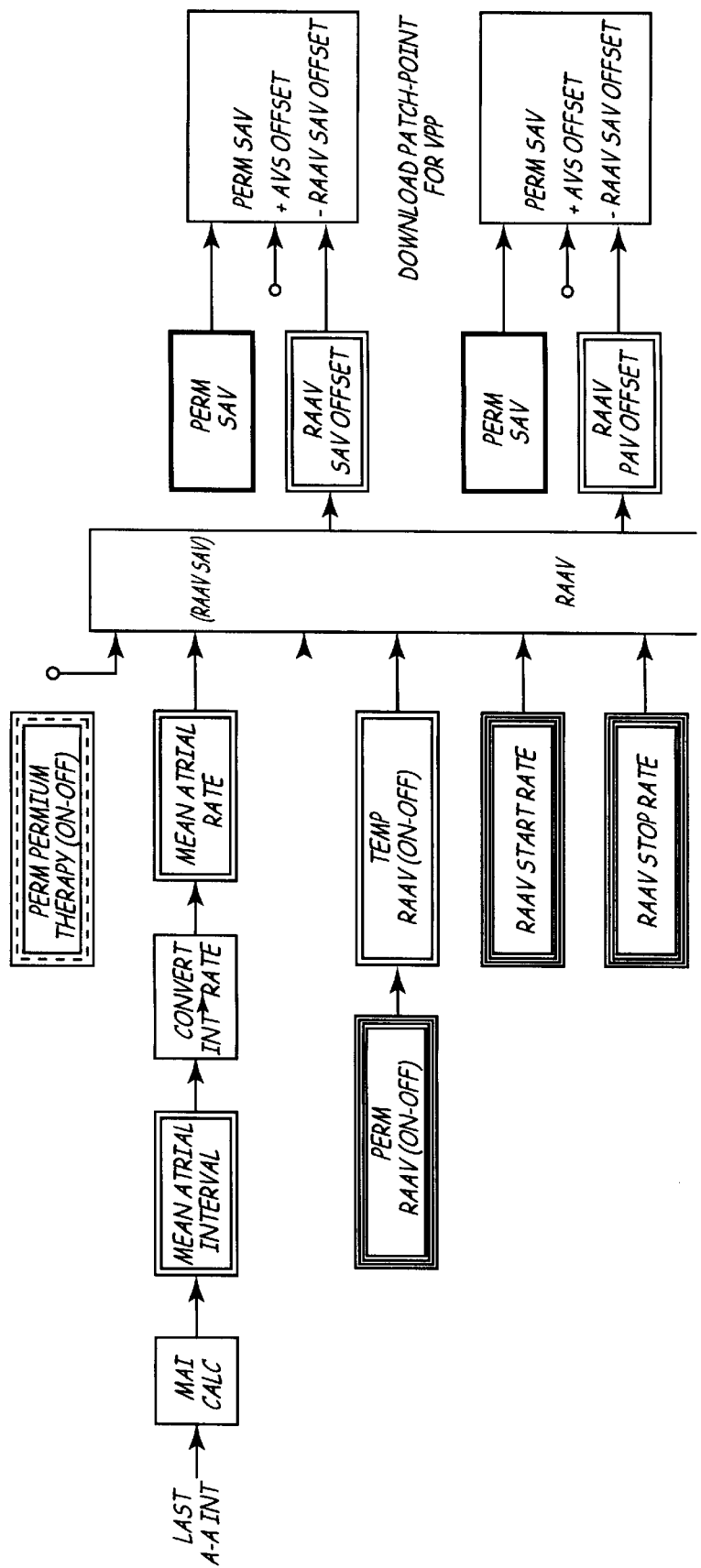
Figure 21C:
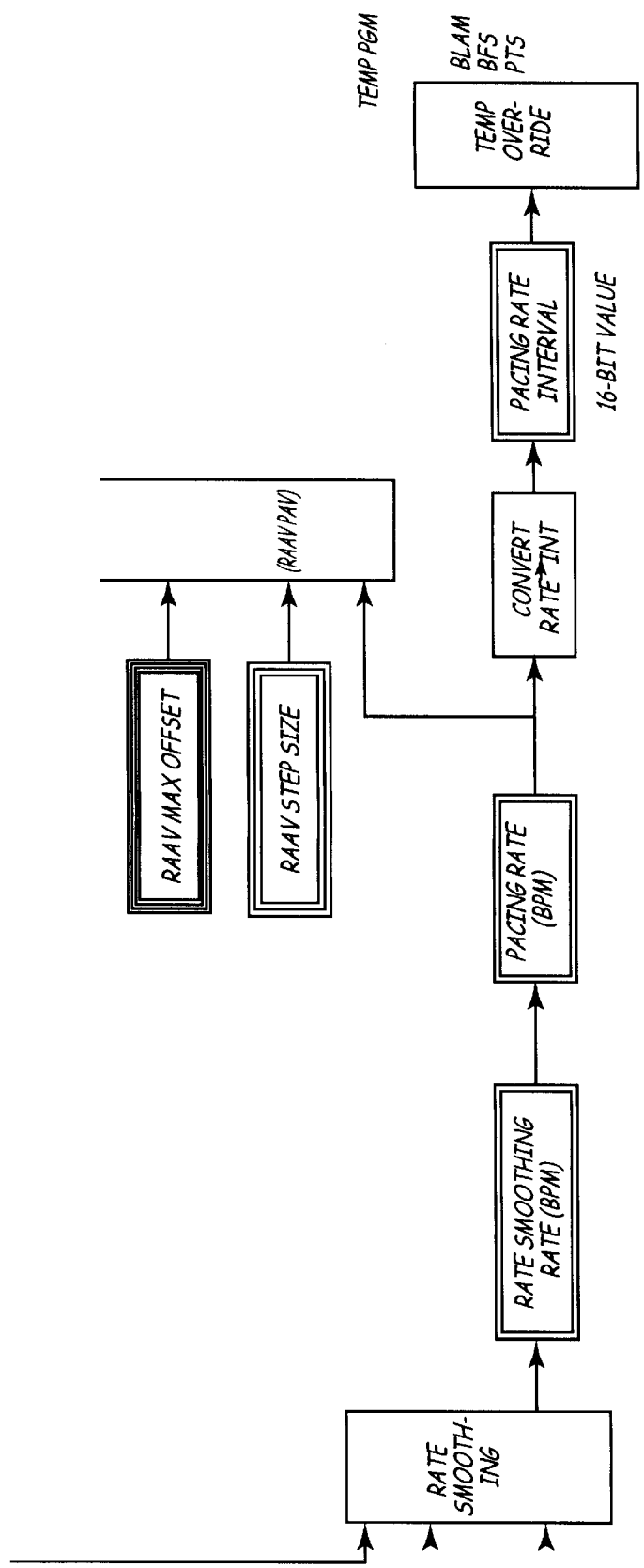
Figure 23A:
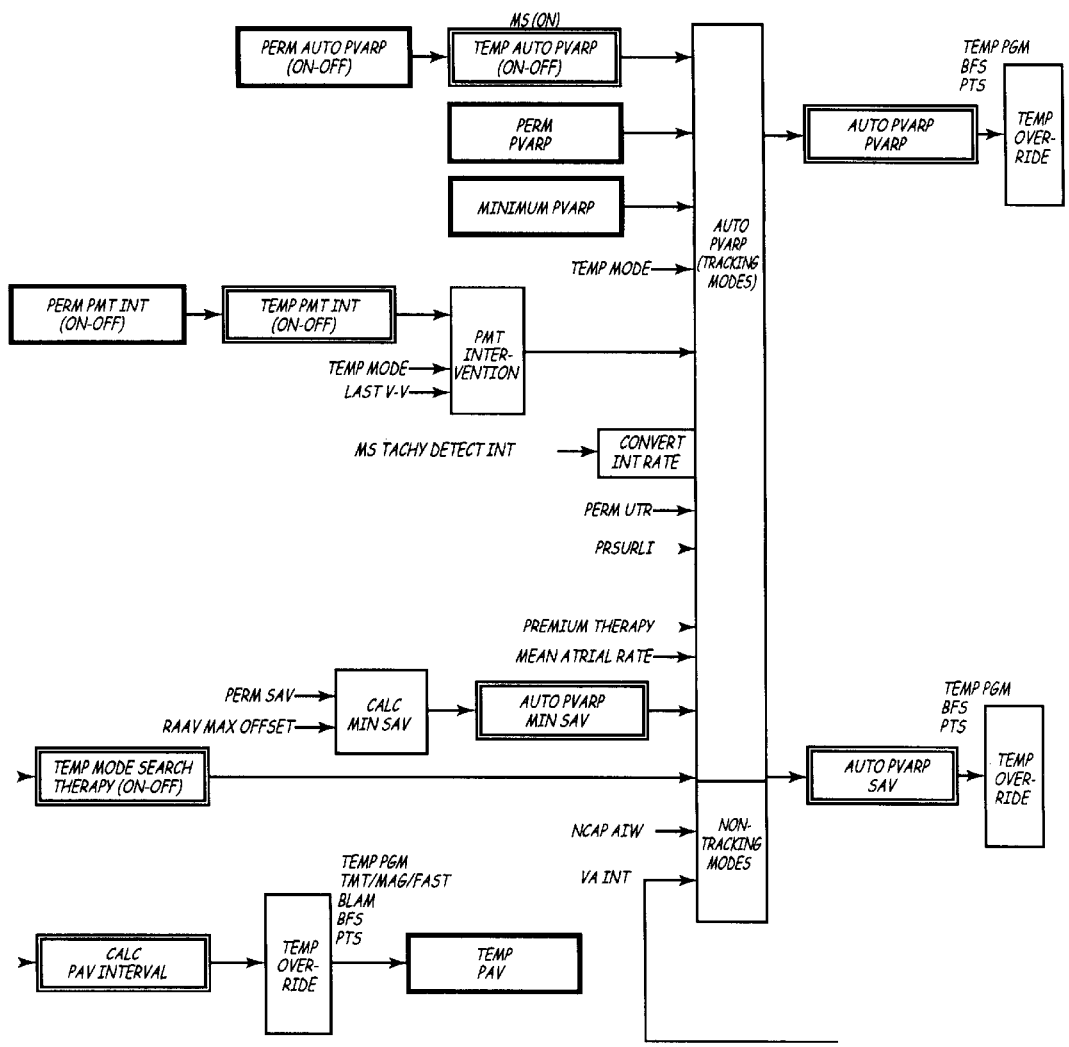
Figure 23B:
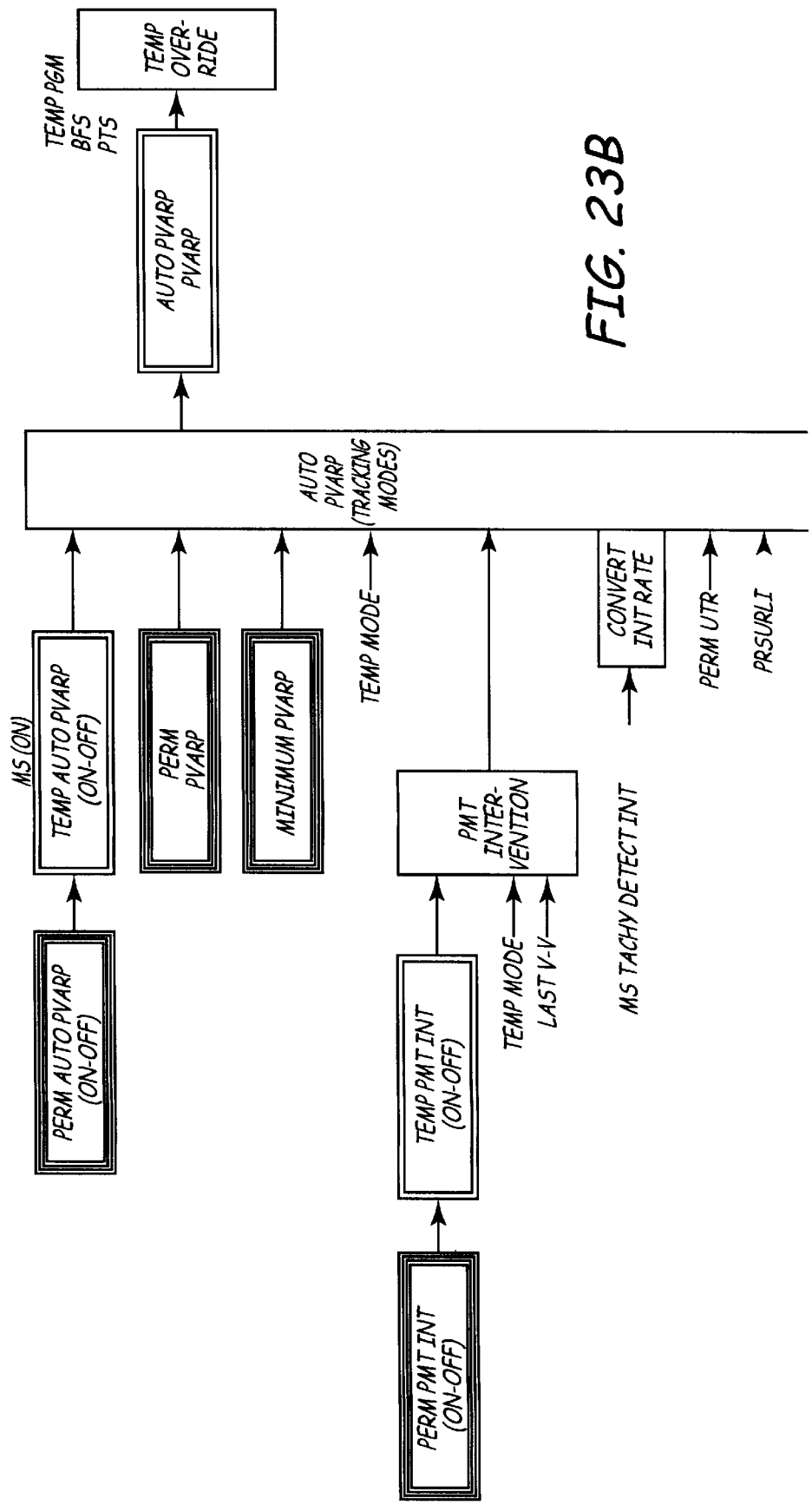
Figure 23C:
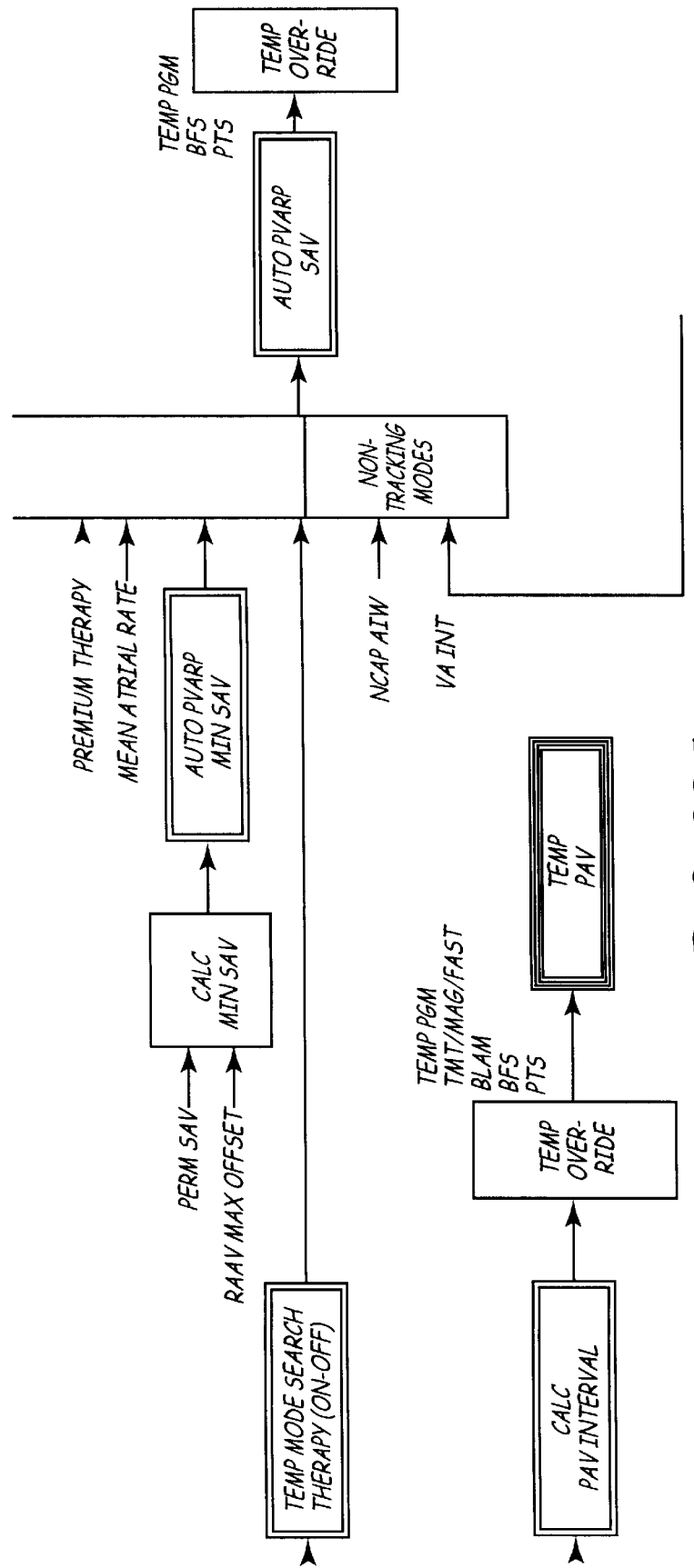

An adaptive (or automatic) post-ventricular atrial refractory period (AUTO PVARP) modular feature 111000 is shown in FIGS. 11, 23 and 24, and (unlabeled) in the phantom box 91100 in FIG. 9. An atrial ventricular interval search (AV SEARCH) modular feature 121000 is shown in FIGS. 12, 20 and 24, and (unlabeled) in phantom box 91200 in FIG. 9. A rate adaptive atrial ventricular (RAAV) modular feature 122000 is shown in FIGS. 12, 21 and 24, and (unlabeled) in the phantom box 91200 in FIG. 9. A mode switch (MODESWITCH) modular feature 131000 is shown in FIGS. 13, 19 and 24, and (unlabeled) in phantom box 91300 in FIG. 9. A physiological rate and physiological rate band calculation (PHYS RATE & PHYS RATE BAND CALCULATION) modular feature 132000 is shown in FIGS. 13, 17 and 24, and (unlabeled) in the phantom box 91300 in FIG. 9.

Figure 15:
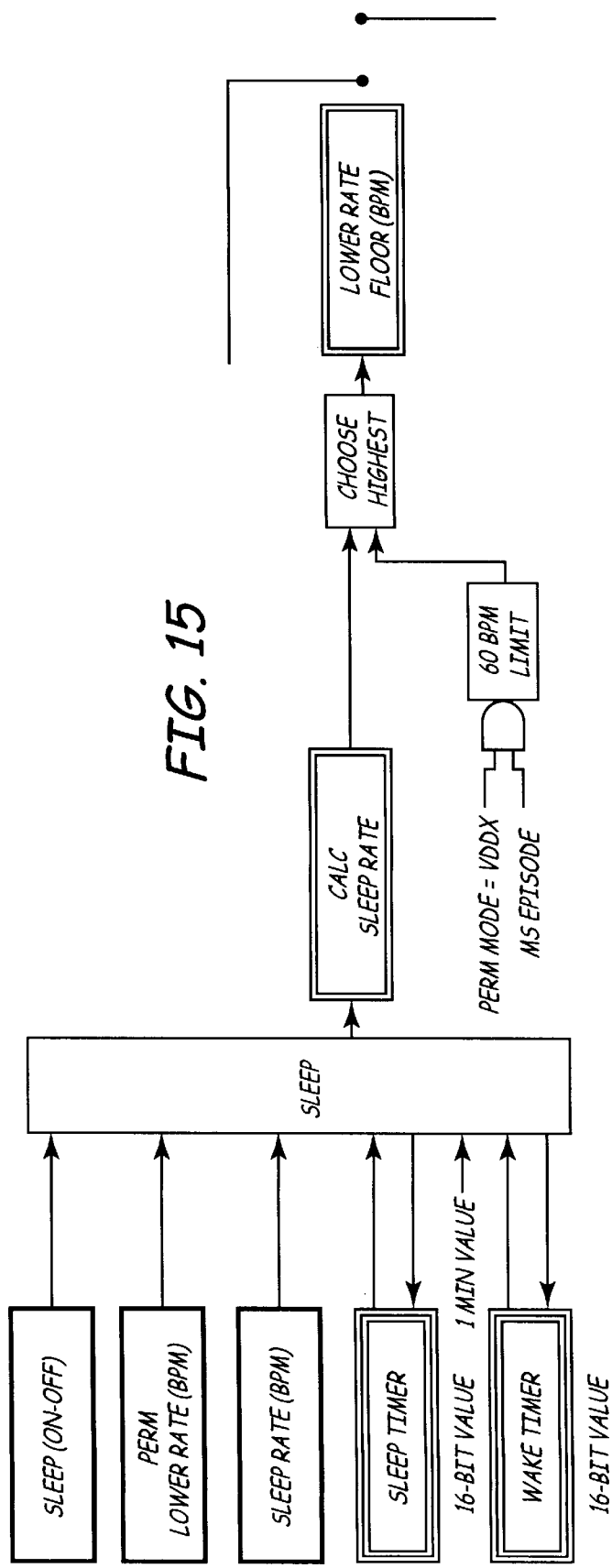
Figure 16:
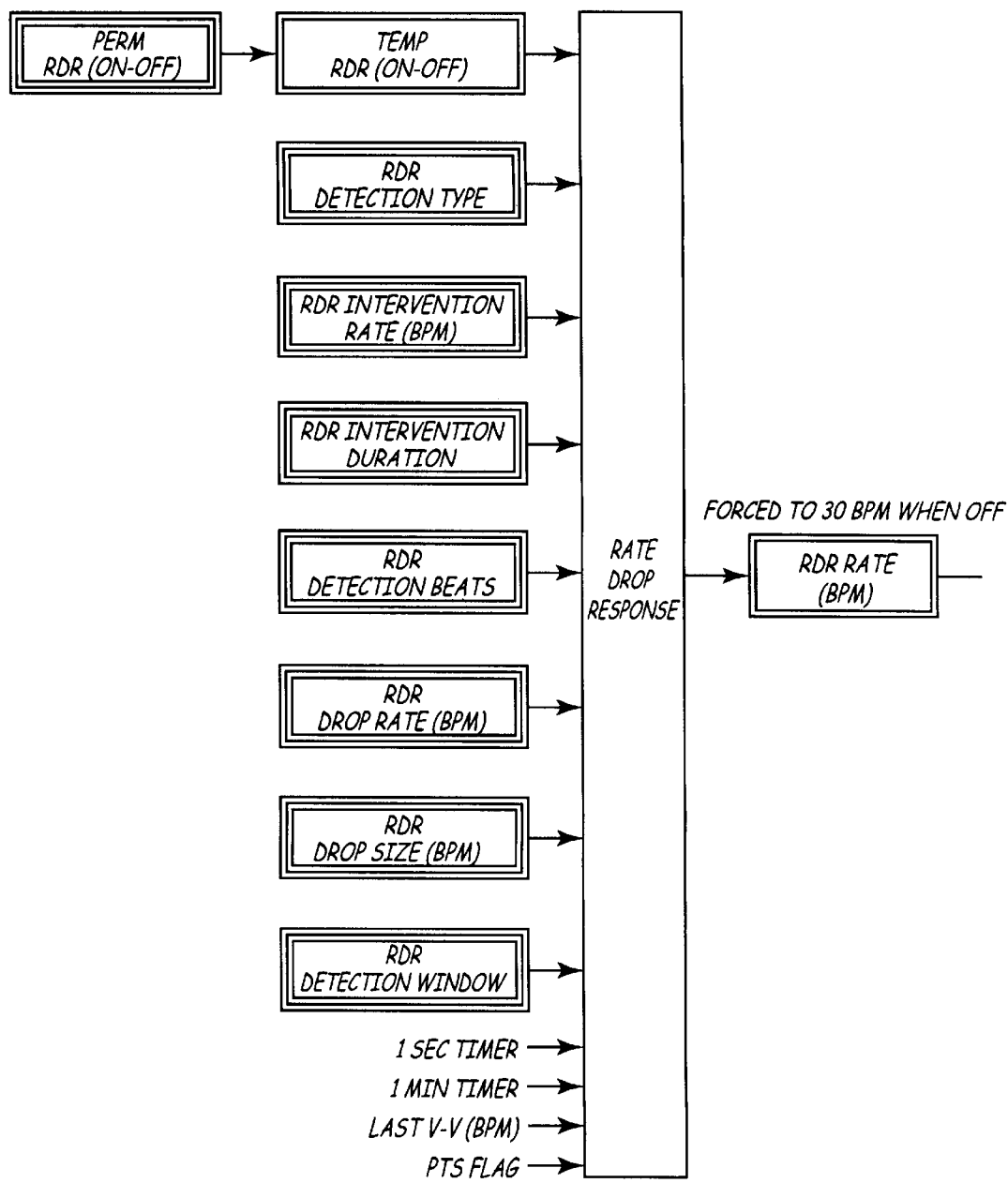
Figure 18A:
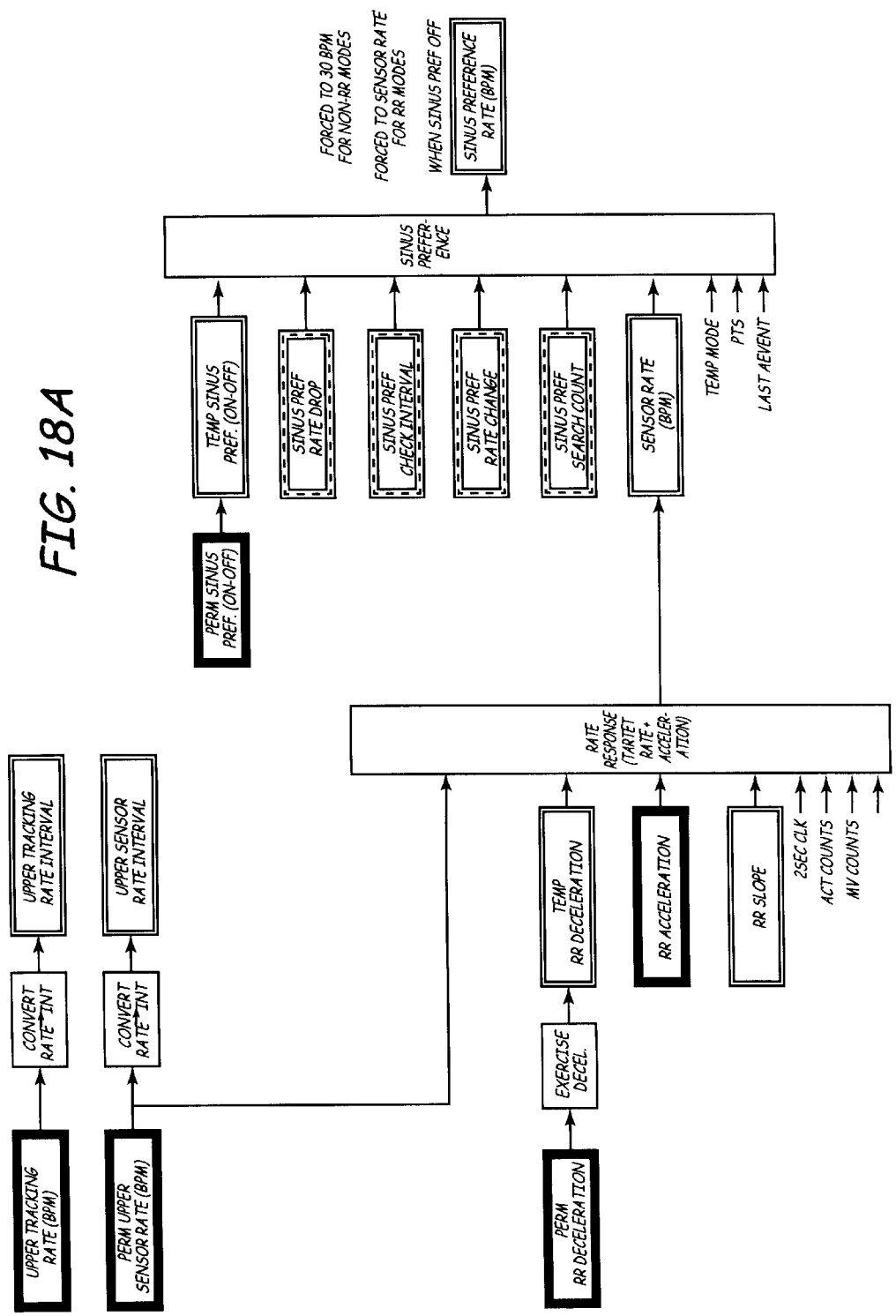
Figure 18B:
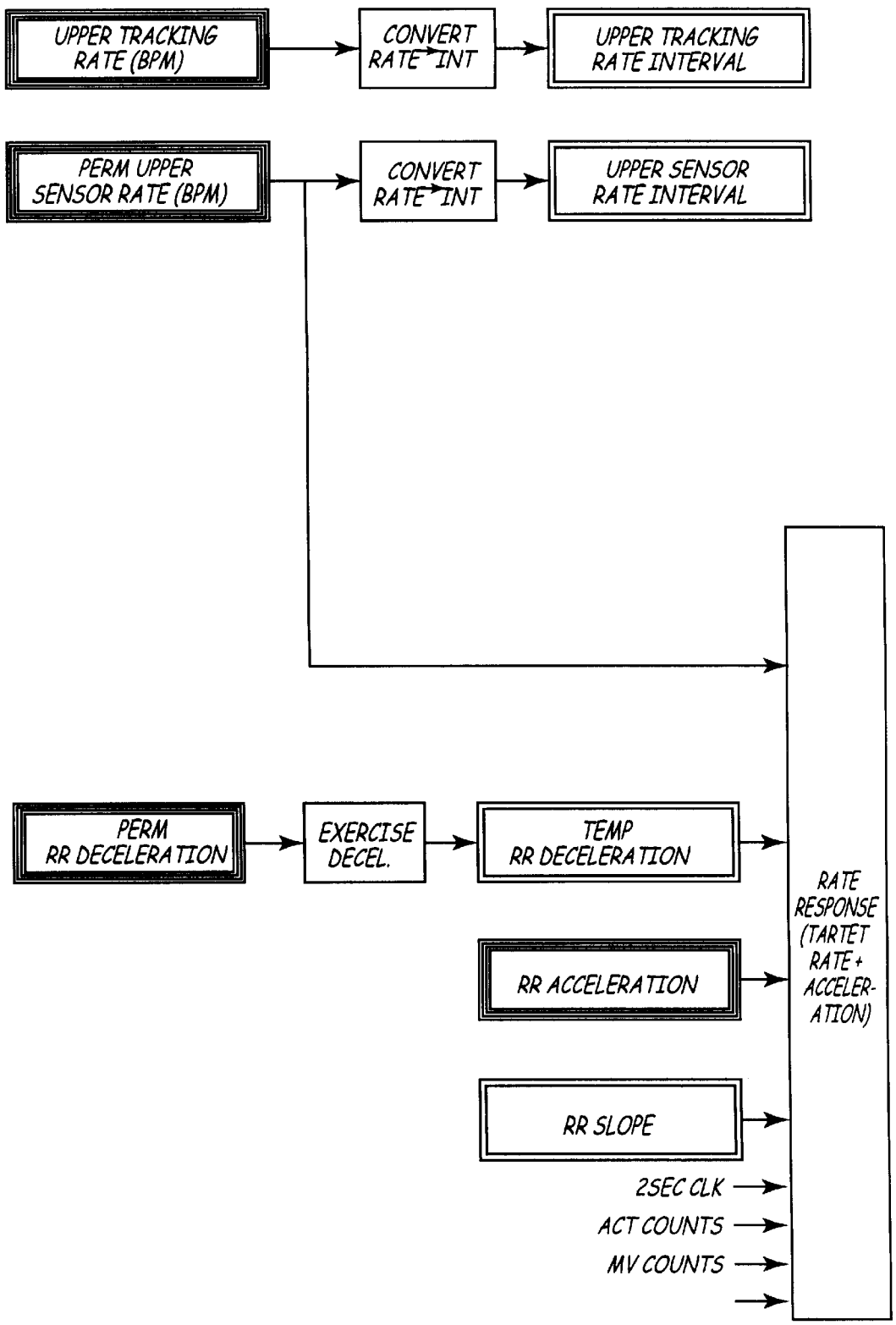
Figure 18C:
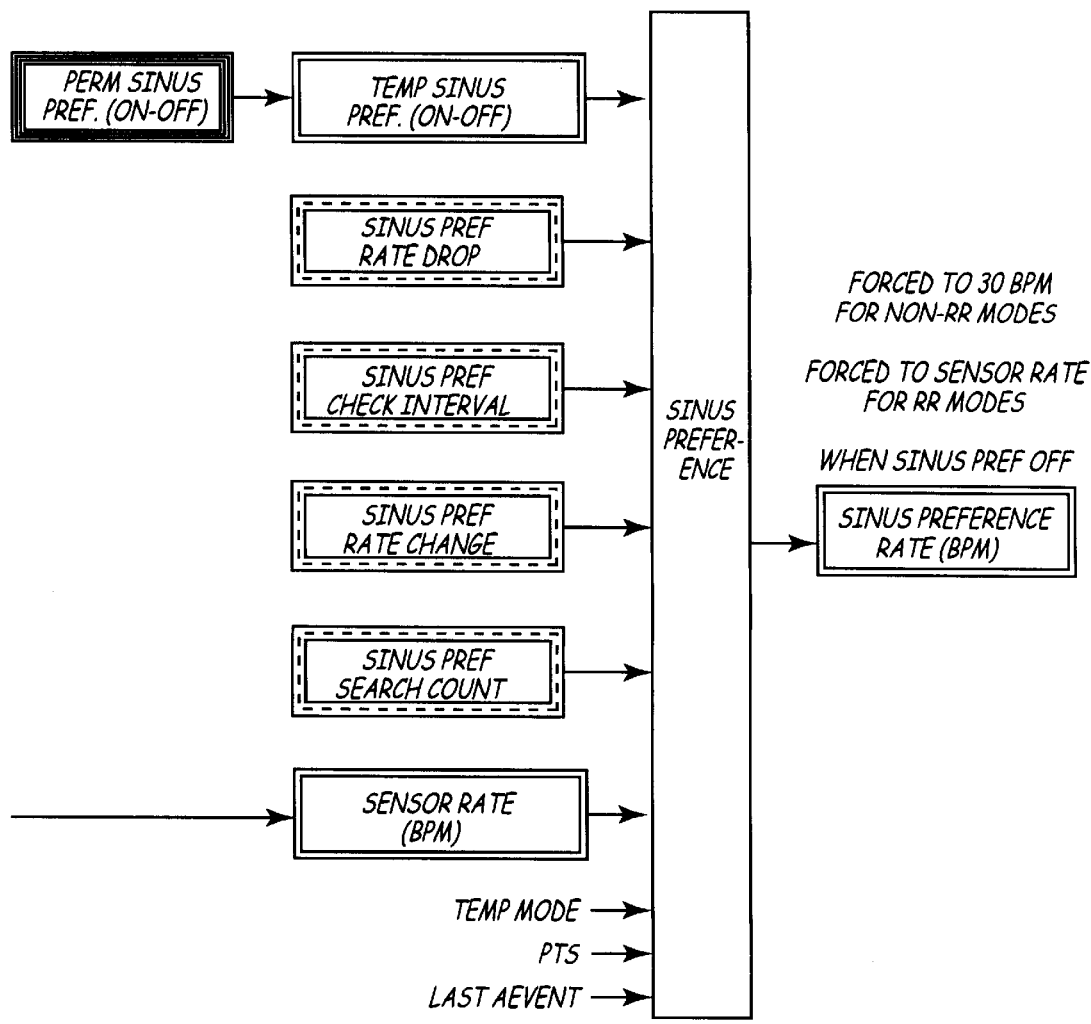

A sinus preference (SINUS PREFERENCE) modular feature 141000 is shown in FIGS. 14, 18 and 24, and (unlabeled) in the phantom box 91400 in FIG. 9. A rate response (RATE RESPONSE) modular feature 142000 is shown in FIGS. 14, 18 and 24, and (unlabeled) in the phantom box 91400 in FIG. 9. A rate drop response (RATE DROP RESPONSE) modular feature 143000 is shown in FIGS. 14, 16 and 24, and (unlabeled) in the phantom box 91400 in FIG. 9. A sleep (SLEEP) modular feature 144000 is shown in FIGS. 14, 15 and 24, and (unlabeled) in the phantom box 91400 in FIG. 9.

As shown in FIGS. 9, 11–13 and 24, the adaptive (or automatic) post-ventricular atrial refractory period (AUTO PVARP) modular feature 111000 receives input from the atrial ventricular interval search (AV SEARCH) modular feature 121000 (via atrial ventricular search offset memory cell 12000 (AVS OFFSET) and along line 112300), the rate adaptive atrial ventricular (RAAV) modular feature 122000 (also along line 112300) and the physiological rate and physiological rate band calculation (PHYS RATE & PHYS RATE BAND CALCULATION) modular feature 132000 (along line 111900). The rate adaptive atrial ventricular (RAAV) modular feature 122000 also receives input from the physiological rate and physiological rate band calculation (PHYS RATE & PHYS RATE BAND CALCULATION) modular feature 132000 (along line 122500, FIG. 21). The rate adaptive atrial ventricular (RAAV) modular feature 122000 also receives input from a last atrial-to-atrial interval input (LAST A—A INT), a mean atrial interval calculation register (MAI CALC), an interval-to-rate converter (CONVERT INT TO RATE) and a mean atrial rate memory cell (MEAN ATRIAL RATE), along line 12400 (FIG. 21).

As shown in FIGS. 9, 14, 18 and 24, the sinus preference (SINUS PREFERENCE) modular feature 141000 receives input from the rate response (RATE RESPONSE) modular feature 142000 (along line 14000). As shown in FIGS. 9, 14, 15 and 24, the rate response (RATE RESPONSE) modular feature 142000 receives input from the sleep (SLEEP) modular feature 144000 (along line 14100).

As shown in FIGS. 11–14 and 25, the pulse generator input register 11005 (PG UR), which inputs the upper rate (UR) pacing interval value to the implantable pulse generator (IPG), receives input from line 11105 from a register write adjuster (RW ADJUST). The register write adjuster (RW ADJUST) receives input from (1) temporary lower rate interval limiter 11205 (TEMP LR_INT LIMIT), for dual chamber modes, (2) either zero for non-WIR or non-zero for WIR, for single chamber modes, and (3) line 11405. The temporary lower rate interval limiter 11205 (TEMP LR_INT LIMIT) receives input from line 11305.

As shown in FIG. 14, the line 11305 connects with upper tracking rate interval memory cell 14105 (UPPER TRACKING RATE INTERVAL). The upper tracking rate interval memory cell 14105 (UPPER TRACKING RATE INTERVAL) receives input from rate-to-interval converter 14205 (CONVERT RATE TO INT). The rate-to-interval converter 14205 (CONVERT RATE TO INT) receives input from upper tracking rate (beats per minute) memory cell 14305 (UPPER TRACKING RATE BPM).

The line 11405 connects with upper sensor rate interval memory cell 14405 (UPPER SENSOR RATE INTERVAL). The upper sensor rate interval memory cell 14405 (UPPER SENSOR RATE INTERVAL) receives input from rate-to-interval converter 14505 (CONVERT RATE TO INT). The rate-to-interval converter 14505 (CONVERT RATE TO INT) receives input from permanent upper sensor rate (beats per minute) memory cell 14605 (PERM SENSOR RATE BPM). The permanent upper sensor rate (beats per minute) memory cell 14605 (PERM SENSOR RATE BPM) also sends an output to the rate response (RATE RESPONSE) modular feature 142000 (FIG. 18). One of ordinary skill in the art, having the benefit of the present disclosure, would recognize that the rate-to-interval conversions may be implemented by separate converters, provided in the lower level firmware 430, and/or, alternatively and equivalently, in the higher level firmware 420.

As shown in FIGS. 11 and 25, the pulse generator input register 11010 (PG EXAR), which inputs the extreme atrial refractory (EXAR) values (for example, 400 ms and 0 ms) to the implantable pulse generator (IPG), receives input from line 11110. The line 11110 receives input from a post-ventricular atrial refractory period greater than 400 ms check register (PVARP>400 CHECK). The post-ventricular atrial refractory period greater than 400 ms check register (PVARP>400 CHECK) receives input from temporary premature ventricular contraction (PVC) response memory cell 11210 (TEMP PVC RESP (ON-OFF)), for the case when the mode switch (MS) is off. The temporary premature ventricular contraction (PVC) response memory cell 11210 (TEMP PVC RESP (ON-OFF)) receives input from permanent premature ventricular contraction (PVC) response memory cell 11310 (PERM PVC RESP (ON-OFF)).

Figure 22:
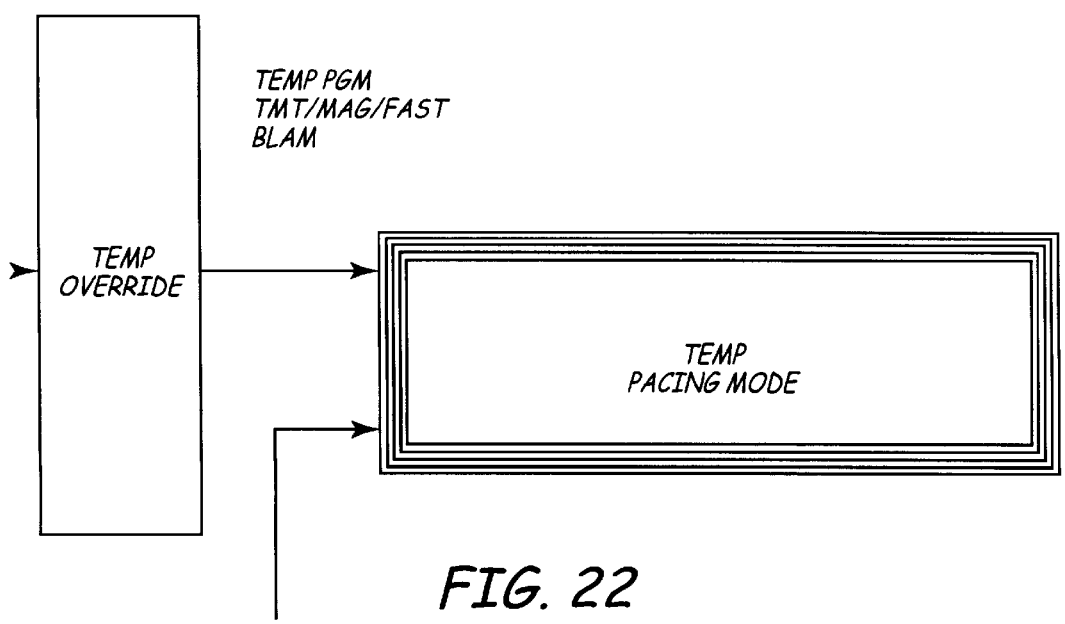

As shown in FIGS. 11 and 25, the pulse generator input register 11015 (PG MODE), which inputs the mode (MODE) value to the implantable pulse generator (IPG), receives input from line 11115. As shown in FIGS. 11, 12, and 22, the line 11115 connects with temporary pacing mode memory cell 12115 (TEMP PACING MODE). The temporary pacing mode memory cell 12115 (TEMP PACING MODE) receives input from temporary override register 12215 (TEMP OVERRIDE). The temporary override register 12215 (TEMP OVERRIDE) receives input from line 12315. The temporary pacing mode memory cell 12115 (TEMP PACING MODE) also receives input from line 12415.

As shown in FIGS. 13 and 19, the line 12315 connects with permanent mode pacing memory cell 131100 (PERM MODE PACING). The permanent mode pacing memory cell 131100 (PERM MODE PACING) also sends an output to mode switch (MS) modular feature 131000 (MODESWITCH). The line 12415 also connects with the mode switch (MS) modular feature 131000 (MODESWITCH). The mode switch (MS) modular feature 131000 (MODESWITCH) receives input from temporary mode switch therapy memory cell (TEMP MODESWITCH THERAPY (ON-OFF)). The temporary mode switch therapy memory cell (TEMP MODESWITCH THERAPY (ON-OFF)) receives input from permanent mode switch therapy memory cell (PERM MODESWITCH THERAPY (ON-OFF)).

The mode switch (MS) modular feature 131000 (MODESWITCH) also receives input from mode switch detection memory cell (MS DETECTION ON-OFF). The mode switch (MS) modular feature 131000 (MODESWITCH) further receives input from mode switch episode status memory cell (MS EPISODE STATUS). The mode switch episode status memory cell (MS EPISODE STATUS) receives input from blanked flutter search register (BLANKED FLUTTER SEARCH). The blanked flutter search register (BLANKED FLUTTER SEARCH) receives input from temporary mode switch blanked flutter search memory cell (TEMP MS BFS (ON-OFF)). The temporary mode switch blanked flutter search memory cell (TEMP MS BFS (ON-OFF)) receives input from permanent mode switch blanked flutter search memory cell (PERM MS BFS (ON-OFF)). The blanked flutter search register (BLANKED FLUTTER SEARCH) also receives input from mode switch blanked flutter search method memory cell (MS BFS METHOD).

The mode switch (MS) modular feature 131000 (MODESWITCH) also receives input from mode switch tachycardia detection interval memory cell (MS TACHY DETECT INTERVAL (MS)). The mode switch (MS) modular feature 131000 (MODESWITCH) further receives input from mode switch sudden onset detect memory cell (MS SUDDEN ONSET DETECT). The mode switch (MS) modular feature 131000 (MODESWITCH) additionally receives input from mode switch detect duration memory cell (MS DETECT DURATION). The mode switch (MS) modular feature 131000 (MODESWITCH) also receives input from a one second timer (1SEC TIMER).

As shown in FIGS. 11 and 25, the pulse generator input register 11020 (PG VSP), which inputs the ventricular safety period (VSP) values (for example, 110 ms and 0 ms) to the implantable pulse generator (IPG), receives input along line 11120 from temporary ventricular safety period (VSP) memory cell 11220 (TEMP VSP (ON-OFF)), for the case when PTS is off. The temporary ventricular safety period (VSP) memory cell 11220 (TEMP VSP (ON-OFF)) receives input from permanent ventricular safety period (VSP) memory cell 11320 (PERM VSP (ON-OFF)).

As shown in FIGS. 11 and 25, the pulse generator input register 11025 (PG RW), which inputs the register write (RW) value (a period of time for loading the pacing engine) to the implantable pulse generator (IPG), receives input along line 11125 from register write (RW) interval memory cell 11225 (RW INTERVAL).

As shown in FIGS. 11–13, 17, 20, 21, 23 and 25, the pulse generator input registers 11030 (PG AR), 11035 (PG VR), 11040 (PG AAB) and 11045 (PG SAV) similarly receive inputs from one or more of the adaptive (or automatic) post-ventricular atrial refractory period (AUTO PVARP) modular feature 111000, the atrial ventricular interval search (AV SEARCH) modular feature 121000, the rate adaptive atrial ventricular (RAAV) modular feature 122000 and the physiological rate and physiological rate band calculation (PHYS RATE & PHYS RATE BAND CALCULATION) modular feature 132000.

Similarly, as shown in FIGS. 11–18, 20, 21, 23 and 25, the pulse generator input registers 11050 (PG PAV), 11055 (PG MPAV), 11060 (PG NCAP), 11065 (PG ESC) and 11070 (PG LR) receive inputs from one or more of the atrial ventricular interval search (AV SEARCH) modular feature 121000, the rate adaptive atrial ventricular (RAAV) modular feature 122000, the physiological rate and physiological rate band calculation (PHYS RATE & PHYS RATE BAND CALCULATION) modular feature 132000, the sinus preference (SINUS PREFERENCE) modular feature 141000, the rate response (RATE RESPONSE) modular feature 142000, the rate drop response (RATE DROP RESPONSE) modular feature 143000 and the sleep (SLEEP) modular feature 144000.

FIGS. 11–14 show enlarged views of the flow diagram 900 shown in FIG. 9 and schematically illustrated in FIG. 24. FIGS. 11–14 correspond with phantom boxes 91100, 91200, 91300 and 91400, respectively, shown in FIG. 9. As described above, the lines 11305 and 11405 extend across the upper portions of FIGS. 11–14. Similarly, the line 11115 extends across FIG. 11 to the temporary pacing mode memory cell 12115 (TEMP PACING MODE) of FIG. 12. The lines 12315 and 12415 extend across FIG. 12 to the permanent mode pacing memory cell 131100 (PERM MODE PACING) and the mode switch (MS) modular feature 131000 (MODESWITCH), respectively, of FIG. 13.

Permanent PMT interval memory cell 111700 (PERM PMT INT (ON-OFF)) is shown in FIGS. 11 and 12. The adaptive (or automatic) post-ventricular atrial refractory period (AUTO PVARP) modular feature 111000 of FIG. 11 receives input from the line 111900, which extends across the middle portion of FIG. 12 to a memory cell associated with an output of the physiological rate and physiological rate band calculation (PHYS RATE & PHYS RATE BAND CALCULATION) modular feature 132000 of FIG. 13. Similarly, the adaptive (or automatic) post-ventricular atrial refractory period (AUTO PVARP) modular feature 111000 of FIG. 11 receives input from line 112000, which connects to a permanent premium therapy memory cell (PERM PREMIUM THERAPY (ON-OFF)) of FIG. 12. The permanent premium therapy memory cell (PERM PREMIUM THERAPY (ON-OFF)) also sends an output to the rate adaptive atrial ventricular (RAAV) modular feature 122000 of FIG. 12.

The adaptive (or automatic) post-ventricular atrial refractory period (AUTO PVARP) modular feature 111000 of FIG. 11 receives input from line 112300, which connects to a calculate sensing atrial ventricular interval memory cell (CALC SAV INTERVAL) associated with an output of the rate adaptive atrial ventricular (RAAV) modular feature 122000 of FIG. 12. Temporary override register 11350 (TEMP OVERRIDE) is shown in FIGS. 11 and 12. Permanent atrial-to-atrial timing memory cell 11565 (PERM A—A TIMING (ON-OFF)) is also shown in FIGS. 11 and 12. Line 11865 in the lower portion of FIG. 11 extends to a (16-bit value) temporary lower rate interval memory cell (TEMP LOWER RATE INTERVAL) of FIG. 12. Line 11570 in the lowest portion of FIG. 11 extends across the lowest portion of FIGS. 12 and 13 to connect with a lower rate floor memory cell (LOWER RATE FLOOR (BPM)) associated with an output of the sleep (SLEEP) modular feature 144000 of FIG. 14.

The line 12400 at the left middle portion of FIG. 12 is input to an interval to rate converter (CONVERT INT TO RATE) that connects to the mean atrial rate memory cell (MEAN ATRIAL RATE), as described above. The line 12400 connects to the mean atrial interval calculation register (MAI CALC) at the right middle portion of FIG. 13. The mean atrial interval calculation register (MAI CALC) receives a signal from the last atrial-to-atrial interval input (LAST A—A INT), as described above. The line 122500 at the left middle portion of FIG. 12 connects to a memory cell associated with an output of the physiological rate and physiological rate band calculation (PHYS RATE & PHYS RATE BAND CALCULATION) modular feature 132000 of FIG. 13. Line 12665 at the lower left portion of FIG. 12 connects to a rate smoothing rate memory cell 13165 (RATE SMOOTHING RATE (BPM)) of the lower right portion of FIG. 13.

A sinus preference rate memory cell 13965 (SINUS PREFERENCE RATE (BPM)) is shown in FIGS. 13 and 14. A rate drop response memory cell 13270 (RDR RATE (BPM)) is also shown in FIGS. 13 and 14. Line 13865 and a choose highest rate register 13765 (CHOOSE HIGHEST RATE) are also shown in FIGS. 13 and 14.

Any of the above-disclosed embodiments of a method and a device according to the present invention enables therapy features to be modular and resolves many feature-to-feature interactions in implantable medical devices. Additionally, any of the above-disclosed embodiments of a method and a device according to the present invention enables features to be easily and quickly added and/or modified and/or deleted in a given design, creates interim values for therapy features, simplifying the development and/or testing of those features. Furthermore, any of the above-disclosed embodiments of a method and a device according to the present invention enables features to operate in the "rate domain" in beats per minute (bpm), makes strategic conversions into the "interval domain" for parameter values that are loaded into hardware timing circuitry, clearly identifies where modular feature algorithms are working in the rate domain and/or in the interval domain and enables efficient use of conversion between the rate domain and the interval domain.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. In particular, every range of values (of the form, "from about a to about b," or, equivalently, "from approximately a to b," or, equivalently, "from approximately a–b") disclosed herein is to be understood as referring to the power set (the set of all subsets) of the respective range of values, in the sense of Georg Cantor. Accordingly, the protection sought herein is as set forth in the claims below.

What is claimed:

1. A method comprising:
  controlling an implantable medical device using a controller having a plurality of modular features, the controller having a firmware architecture allowing modular feature design and implementation;
  coordinating between and among the plurality of modular features to reduce feature-to-feature interactions; and
  identifying at least one first modular feature working in a rate domain and at least one second modular feature working in an interval domain, enabling efficient conversion between the rate domain and the interval domain.

2. The method of claim 1, wherein controlling the implantable medical device using the controller having the plurality of modular features comprises controlling a pulse generator for an implantable pacemaker.

3. The method of claim 2, wherein controlling the pulse generator for the implantable pacemaker comprises controlling the pulse generator for at least one of an implantable anti-brady pacemaker and an implantable anti-tachy pacemaker.

4. The method of claim 3, wherein controlling the implantable medical device using the controller having the plurality of modular features comprises at least one of adding a modular feature to the firmware, modifying a modular feature of the firmware and deleting a modular feature from the firmware.

5. The method of claim 4, wherein coordinating between and among the plurality of modular features to reduce feature-to-feature interactions comprises testing at least one modular feature of the plurality of modular features to debug the at least one modular feature.

6. The method of claim 1, wherein controlling the implantable medical device using the controller having the plurality of modular features comprises at least one of adding a modular feature to the firmware, modifying a modular feature of the firmware and deleting a modular feature from the firmware.

7. The method of claim 6, wherein coordinating between and among the plurality of modular features to reduce feature-to-feature interactions comprises testing at least one modular feature of the plurality of modular features to debug the at least one modular feature.

8. The method of claim 1, wherein coordinating between and among the plurality of modular features to reduce feature-to-feature interactions comprises testing at least one modular feature of the plurality of modular features to debug the at least one modular feature.

9. The method of claim 2, wherein controlling the implantable medical device using the controller having the plurality of modular features comprises at least one of adding a modular feature to the firmware, modifying a modular feature of the firmware and deleting a modular feature from the firmware.

10. The method of claim 7, wherein coordinating between and among the plurality of modular features to reduce feature-to-feature interactions comprises testing at least one modular feature of the plurality of modular features to debug the at least one modular feature.

11. A device comprising:
an implantable medical device; and
a controller controlling the implantable medical device, the controller having a plurality of modular features and having a firmware architecture allowing modular feature design and implementation, the firmware architecture coordinating between and among the plurality of modular features to reduce feature-to-feature interactions, the controller also having a converter enabling efficient conversion between at least one identifiable first modular feature working in a rate domain and at least one identifiable second modular feature working in an interval domain.

12. The device of claim 11, wherein the controller having the plurality of modular features controls a pulse generator for an implantable pacemaker.

13. The device of claim 12, wherein the controller having the plurality of modular features controls the pulse generator for at least one of an implantable anti-brady pacemaker and an implantable anti-tachy pacemaker.

14. The device of claim 13, wherein the firmware architecture allowing modular feature design and implementation allows at least one of adding a modular feature to the firmware, modifying a modular feature of the firmware and deleting a modular feature from the firmware.

15. The device of claim 14, wherein the firmware architecture coordinating between and among the plurality of modular features to reduce feature-to-feature interactions allows testing of at least one modular feature of the plurality of modular features to debug the at least one modular feature.

16. The device of claim 12, wherein the firmware architecture allowing modular feature design and implementation allows at least one of adding a modular feature to the firmware, modifying a modular feature of the firmware and deleting a modular feature from the firmware.

17. The device of claim 16, wherein the firmware architecture coordinating between and among the plurality of modular features to reduce feature-to-feature interactions allows testing of at least one modular feature of the plurality of modular features to debug the at least one modular feature.

18. The device of claim 11, wherein the firmware architecture allowing modular feature design and implementation allows at least one of adding a modular feature to the firmware, modifying a modular feature of the firmware and deleting a modular feature from the firmware.

19. The device of claim 18, wherein the firmware architecture coordinating between and among the plurality of modular features to reduce feature-to-feature interactions allows testing of at least one modular feature of the plurality of modular features to debug the at least one modular feature.

20. The device of claim 11, wherein the firmware architecture coordinating between and among the plurality of modular features to reduce feature-to-feature interactions allows testing of at least one modular feature of the plurality of modular features to debug the at least one modular feature.

21. A device comprising:
means for controlling an implantable medical device using a controller having a plurality of modular features, the controller having a firmware architecture allowing modular feature design and implementation;
means for coordinating between and among the plurality of modular features to reduce feature-to-feature interactions; and
means for identifying at least one first modular feature working in a rate domain and at least one second modular feature working in an interval domain, enabling efficient conversion between the rate domain and the interval domain.

22. The device of claim 21, wherein the means for controlling the implantable medical device using the controller having the plurality of modular features comprises controlling a pulse generator for an implantable pacemaker.

23. The device of claim 22, wherein the means for controlling the pulse generator for the implantable pacemaker comprises controlling the pulse generator for at least one of an implantable anti-brady pacemaker and an implantable anti-tachy pacemaker.

24. The device of claim 23, wherein the means for controlling the implantable medical device using the controller having the plurality of modular features comprises at least one of adding a modular feature to the firmware, modifying a modular feature of the firmware and deleting a modular feature from the firmware.

25. The device of claim 24, wherein the means for coordinating between and among the plurality of modular features to reduce feature-to-feature interactions comprises testing at least one modular feature of the plurality of modular features to debug the at least one modular feature.

26. The device of claim 22, wherein the means for controlling the implantable medical device using the controller having the plurality of modular features comprises at least one of adding a modular feature to the firmware, modifying a modular feature of the firmware and deleting a modular feature from the firmware.

27. The device of claim 26, wherein the means for coordinating between and among the plurality of modular features to reduce feature-to-feature interactions comprises testing at least one modular feature of the plurality of modular features to debug the at least one modular feature.

28. The device of claim 21, wherein the means for controlling the implantable medical device using the controller having the plurality of modular features comprises at least one of adding a modular feature to the firmware, modifying a modular feature of the firmware and deleting a modular feature from the firmware.

29. The device of claim 28, wherein the means for coordinating between and among the plurality of modular features to reduce feature-to-feature interactions comprises testing at least one modular feature of the plurality of modular features to debug the at least one modular feature.

30. The device of claim 21, wherein the means for coordinating between and among the plurality of modular features to reduce feature-to-feature interactions comprises testing at least one modular feature of the plurality of modular features to debug the at least one modular feature.

* * * * *

UNITED STATES PATENT AND TRADEMARK OFFICE
CERTIFICATE OF CORRECTION

PATENT NO. : 6,594,526 B2
DATED : July 15, 2003
INVENTOR(S) : Robert A. Betzold

It is certified that error appears in the above-identified patent and that said Letters Patent is hereby corrected as shown below:

Column 17,
Line 29, delete "claim 7" and insert -- claim 9 --.

Signed and Sealed this

Twenty-third Day of May, 2006

JON W. DUDAS
*Director of the United States Patent and Trademark Office*